(12) United States Patent
Bhakdi

(10) Patent No.: US 10,907,211 B1
(45) Date of Patent: Feb. 2, 2021

(54) METHODS AND COMPOSITIONS FOR DETECTING CANCER BIOMARKERS IN BODILY FLUIDS

(71) Applicant: Quantgene Inc., Berkeley, CA (US)

(72) Inventor: Johannes Bhakdi, Berkeley, CA (US)

(73) Assignee: QUANTGENE INC., Santa Monica, CA (US)

( * ) Notice: Subject to any disclaimer, the term of this patent is extended or adjusted under 35 U.S.C. 154(b) by 315 days.

(21) Appl. No.: 15/434,799

(22) Filed: Feb. 16, 2017

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,952,170 | A | 9/1999 | Stroun et al. |
| 6,329,179 | B1 | 12/2001 | Kopreski et al. |
| 7,163,789 | B2 | 1/2007 | Chen et al. |
| 8,486,626 | B2 | 7/2013 | Umansky et al. |
| RE44,596 | E | 11/2013 | Stroun et al. |
| 8,808,990 | B2 | 8/2014 | Lidgard et al. |
| 9,121,071 | B2 | 9/2015 | Zou et al. |
| 9,163,229 | B2 | 10/2015 | Melkonyan et al. |
| 2012/0004116 | A1 | 1/2012 | Tsao et al. |
| 2012/0165217 | A1 | 6/2012 | Gold et al. |
| 2013/0280727 | A1 | 10/2013 | Shuber et al. |
| 2014/0242581 | A1 | 8/2014 | Johnson |
| 2014/0296081 | A1 | 10/2014 | Diehn et al. |
| 2015/0315657 | A1* | 11/2015 | Rhodes ................ C12Q 1/6886 424/133.1 |
| 2015/0344957 | A1 | 12/2015 | Abdel-Wahab |
| 2016/0010081 | A1 | 1/2016 | Allawi et al. |
| 2016/0032396 | A1 | 2/2016 | Diehn et al. |
| 2016/0251704 | A1 | 9/2016 | Talasaz et al. |
| 2016/0333416 | A1 | 11/2016 | Babiarz et al. |

FOREIGN PATENT DOCUMENTS

WO WO 2015/058176 A1 4/2015

OTHER PUBLICATIONS

Handbook of Chemistry and Physics, 49th Edition, 1968, Weast (ed.), The Chemical Rubber Co., Cleveland, Ohio, p. A-245.*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Benesova, et al., "Mutation-based detection and monitoring of cell-free tumor DNA in peripheral blood of cancer patients." Analytical Biochemistry (Feb. 2013); 433(2): 227-234.
Dawson, et al., "Analysis of Circulating Tumor DNA to Monitor Metastatic Breast Cancer." N Engl J Med. (Mar. 2013); 368(13): 1199-1209.
Forshew, et al., "Noninvasive Identification and Monitoring of Cancer Mutations by Targeted Deep Sequencing of Plasma DNA." Science Translational Medicine (May 2012); 4(136): 136ra168, 13 pages.
Ilie, et al., "Current challenges for detection of circulating tumor cells and cell-free circulating nucleic acids, and their characterization in non-small cell lung carcinoma patients. What is the best blood substrate for personalized medicine?" Annals of Translational Medicine (Nov. 2014); 2(11): 107, pp. 1-10.
Shaw, et al., "Genomic analysis of circulating cell-free DNA infers breast cancer dormancy." Genome Res. (2012); 22(2): 220-231.
Juppner, "Functional Properties of the PTH/PTHrP Receptor," (Bone 1995 vol. 17 No. 2 Supplement 39S-42S) (Year: 1995).

* cited by examiner

*Primary Examiner* — James Martinell
(74) *Attorney, Agent, or Firm* — Cooley LLP

(57) ABSTRACT

The present invention provides methods, compositions, reaction mixtures, and kits for detecting cancer biomarkers in a bodily fluid from a subject. Also provided are methods for selecting cancer biomarkers for use in detecting one or more types of cancer in a subject.

9 Claims, 7 Drawing Sheets
Specification includes a Sequence Listing.

METHODS AND COMPOSITIONS FOR DETECTING CANCER BIOMARKERS IN BODILY FLUIDS

FIELD OF THE INVENTION

The present invention generally relates to early cancer detection. More specifically, the invention provides methods and compositions for detecting the presence of cancer mutations in bodily fluids of a subject, which can be useful for determining the type of cancer as well as the prognosis and evaluation of treatment options.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: QUAT_001_03US_SeqList_ST25.txt, date recorded: Sep. 13, 2017, file size 3 kilobytes).

BACKGROUND OF THE INVENTION

Recent studies have shown that nucleic acids harboring mutations in cancerous tissues, circulating cells, and cell-free (cf) nucleic acids present in bodily fluids can aid in identifying and selecting individuals with cancer or other diseases associated with such genetic alterations. See, e.g., Ilie et al., 2014, Annals of Translational Medicine, 2:1-10, Benesova et al., 2013, Anal Biochem. 433:227-34; Dawson et al., 2013, N Engl J Med. 368:1199-1209; Forshew et al., 2012, Science Translational Medicine, 4:136ra168; Shaw et al., 2012, Genome Res. 22:220-31. While malignant organ tumors are most often detected at later stages through conventional screening methods or clinical symptoms, circulating tumor cells (CTCs) as well as circulating tumor nucleic acids (e.g., circulating tumor DNA (ctDNA)) may be present in bodily fluids from very early stage to late stage cancers. As such, recovery and analysis of CTCs and/or circulating tumor nucleic acids from a sample of bodily fluid from a subject in a so-called 'liquid biopsy" may be a non-invasive, repeatable diagnostic, prognostic and/or theranostic tool for many types of cancers. However, current methods for utilizing nucleic acids extracted from liquid biopsies for detecting and/or monitoring cancer can be limited in sensitivity and specificity. Thus there is a need in the art for a method for detecting mutations in genes associated with cancer from bodily fluids with improved sensitivity and specificity.

SUMMARY OF THE INVENTION

In one aspect, provided herein is a method for detecting one or more types of cancer in a subject, the method comprising: a) pre-amplifying DNA prepared from a liquid biological sample obtained from the subject using a pre-amplification reaction with a first set of primers directed against one or more target genes carrying one or more target gene mutations, wherein the one or more target gene mutations comprise a minimum number of target gene mutations needed to detect the one or more types of cancer; b) amplifying the pre-amplified DNA obtain in step a) in an amplification reaction using a second set of primers directed against the one or more target genes carrying one or more target gene mutations pre-amplified in step a); and c) detecting one or more amplification products from the amplification reaction in step b), wherein detection of the one or more second amplification products indicates presence of the one or more types of cancer in the subject. In some cases, the detection of the one or more amplification products indicates the presence of the one or more target gene mutations in the liquid biological sample with a sensitivity of greater than or equal to 30%. In some cases, the detection of the one or more amplification products indicates the presence of the one or more target gene mutations in the liquid biological sample with a sensitivity of greater than or equal to 40%. In some cases, the detection of the one or more amplification products indicates the presence of the one or more target gene mutations in the liquid biological sample with a specificity of greater than or equal to 60%. In some cases, the detection of the one or more amplification products indicates the presence of the one or more target gene mutations in the liquid biological sample with a specificity of greater than or equal to 80%. In some cases, the detection of the one or more amplification products indicates the presence of the one or more target gene mutations in the liquid biological sample with a specificity of greater than or equal to 90%. In some cases, the detection of the one or more amplification products indicates the presence of the one or more target gene mutations in the liquid biological sample with a sensitivity of greater than or equal to 30%, and a specificity of greater than or equal to 60%. In some cases, the minimum number of target gene mutations is selected comprising the use of an algorithm. In some cases, the minimum number of target gene mutations is about 10 to about 300. In some cases, the one or more types of cancer are colorectal cancer. In some cases, the one or more target gene mutations comprise the mutations listed in Table 1a-1c. In some cases, the one or more types of cancer are pancreatic cancer. In some cases, the one or more target gene mutations comprise the mutations listed in Table 2a-2b. In some cases, the one or more type of cancer is colorectal cancer and pancreatic cancer. In some cases, the one or more target gene mutations comprise the mutations listed in Table 15. In some cases, the one or more types of cancer is adrenocortical cancer. In some cases, the one or more target gene mutations comprise the mutations listed in Table 3a-3b. In some cases, the one or more types of cancer is melanoma. In some cases, the one or more target gene mutations comprise the mutations listed in Table 4a-4b. In some cases, the one or more types of cancer is cutaneous melanoma. In some cases, the one or more target gene mutations comprise the mutations listed in Table 5a-5b. In some cases, the one or more types of cancer is stomach adenocarcinoma. In some cases, the one or more target gene mutations comprise the mutations listed in Table 6a-6b. In some cases, the one or more types of cancer is bladder cancer. In some cases, the one or more target gene mutations comprise the mutations listed in Table 7a-7b. In some cases, the one or more types of cancer is lung adenocarcinoma. In some cases, the one or more target gene mutations comprise the mutations listed in Table 8a-8b. In some cases, the one or more types of cancer is lung squamous cell carcinoma. In some cases, the one or more target gene mutations comprise the mutations listed in Table 9a-9b. In some cases, the one or more types of cancer is cervical cancer. In some cases, the one or more target gene mutations comprise the mutations listed in Table 10a-10b. In some cases, the one or more types of cancer is ovarian cancer. In some cases, the one or more target gene mutations comprise the mutations listed in Table 11. In some cases, the one or more types of cancer is breast cancer. In some cases, the one or more target gene mutations comprise the mutations listed in Table 12a-12b. In some cases, the one or more types of cancer is leukemia. In some cases, the one or more target gene mutations comprise the mutations listed in Table 13. In some cases, the one or more target gene mutations comprise the mutations listed in Table 14a-14b. In some cases, the method further comprises diluting the DNA from the pre-amplification reaction prior to the amplification reaction. In some cases, the pre-amplification reaction is a polymerase chain reaction. In some cases, the PCR is conducted for 10-14 cycles. In some cases, the amplification reaction comprises a digital PCR reaction. In some cases, the digital PCR is droplet digital PCR. In some cases, the liquid biological sample is blood, serum, urine, saliva, sputum, cerebrospinal fluid, lymph, stool, or ejaculate. In some cases, the liquid biological sample is blood. In some cases, the method further comprises fractionating the blood into a buffy coat and a plasma fraction prior to extracting the DNA. In some cases, the DNA is extracted from the buffy coat fraction of the blood. In some cases, the DNA is extracted from the plasma fraction of the blood. In some cases, the liquid biological sample is serum. In some cases, the DNA is genomic DNA (gDNA) or complementary DNA (cDNA). In some cases, the gDNA is circulating tumor DNA (ctDNA). In some cases, the cDNA is reverse transcribed from extracellular RNA. In some cases, the gDNA is derived from circulating tumor cells or microvesicles. In some cases, the extracellular RNA is derived from exosomes. In some cases, the first set of primers and the second set of primers are an identical set of primers. In some cases, the identical set of primers are complementary to target gene sequences in the one or more target genes carrying one or more target gene mutations that do not carry the target gene mutation. In some cases, the detecting comprises using a plurality of labeled probes, wherein each of the plurality of labeled probes specific for a target gene mutation from the minimum number of target gene mutations. In some cases, the plurality of labeled probes is oligonucleotides, wherein each of the plurality of labeled probes comprises sequence complementary to a target gene mutation from the minimum number of target gene mutations. In some cases, the detecting comprises high throughput sequencing.

In another aspect, provided herein is a reaction mixture comprising a set of primers for amplifying DNA prepared from a liquid biological sample obtained from a subject, wherein the set of primers is directed against a plurality of target genes carrying one or more target gene mutations. In some cases, the plurality of target genes are selected from Tables 1a, 1b, 1c, 2a, 2b, 3a, 3b, 4a, 4b, 5a, 5b, 6a, 6b, 7a, 7b, 8a, 8b, 9a, 9b, 10a, 10b, 11, 12a, 12b, 13, 14a, 14b or any combination thereof. In some cases, the plurality of target genes comprises 5 or more target genes. In some cases, the plurality of target gene mutations comprise a minimum number of target gene mutations needed to detect one or more types of cancer in the subject. In some cases, the minimum number of target gene mutations is selected comprising the use of an algorithm. In some cases, the minimum number of target gene mutations is about 10 to about 300. In some cases, the one or more types of cancer are colorectal cancer. In some cases, the one or more target gene mutations comprise the mutations listed in Table 1a-1c. In some cases, the one or more types of cancer are pancreatic cancer. In some cases, the one or more target gene mutations comprise the mutations listed in Table 2a-2b. In some cases, the one or more types of cancer are colorectal cancer and pancreatic cancer. In some cases, the one or more target gene mutations comprise the mutations listed in Table 15. In some cases, the one or more types of cancer is adrenocortical cancer. In some cases, the one or more target gene mutations comprise the mutations listed in Table 3a-3b. In some cases, the one or more types of cancer is melanoma. In some cases, the one or more target gene mutations comprise the mutations listed in Table 4a-4b. In some cases, the one or more types of cancer is cutaneous melanoma. In some cases, the one or more target gene mutations comprise the mutations listed in Table 5a-5b. In some cases, the one or more types of cancer is stomach adenocarcinoma. In some cases, the one or more target gene mutations comprise the mutations listed in Table 6a-6b. In some cases, the one or more types of cancer is bladder cancer. In some cases, the one or more target gene mutations comprise the mutations listed in Table 7a-7b. In some cases, the one or more types of cancer is lung adenocarcinoma. In some cases, the one or more target gene mutations comprise the mutations listed in Table 8a-8b. In some cases, the one or more types of cancer is lung squamous cell carcinoma. In some cases, the one or more target gene mutations comprise the mutations listed in Table 9a-9b. In some cases, the one or more types of cancer is cervical cancer. In some cases, the one or more target gene mutations comprise the mutations listed in Table 10a-10b. In some cases, the one or more types of cancer is ovarian cancer. In some cases, the one or more target gene mutations comprise the mutations listed in Table 11. In some cases, the one or more types of cancer is breast cancer. In some cases, the one or more target gene mutations comprise the mutations listed in Table 12a-12b. In some cases, the one or more types of cancer is leukemia. In some cases, the one or more target gene mutations comprise the mutations listed in Table 13. In some cases, the one or more target gene mutations comprise the mutations listed in Table 14a-14b. In some cases, the liquid biological sample is blood, serum, urine, saliva, sputum, cerebrospinal fluid, lymph, stool, or ejaculate. In some cases, the liquid biological sample is blood. In some cases, the blood is a buffy coat fraction. In some cases, the blood is a plasma fraction. In some cases, the liquid biological sample is serum. In some cases, the DNA is genomic DNA (gDNA) or complementary DNA (cDNA). In some cases, the gDNA is circulating tumor DNA (ctDNA). In some cases, the cDNA is reverse transcribed from extracellular RNA. In some cases, the gDNA is derived from circulating tumor cells or microvesicles. In some cases, the extracellular RNA is derived from exosomes. In some cases, the first set of primers and the second set of primers are an identical set of primers. In some cases, the identical set of primers are complementary to target gene sequences in the one or more target genes carrying one or more target gene mutations that do not carry the target gene mutation. In some cases, the reaction mixture further comprises a plurality of labeled probes, wherein each of the plurality of labeled probes is specific for a target gene mutation from the minimum number of target gene mutations. In some cases, the plurality of labeled probes is oligonucleotides, wherein each of the plurality of labeled probes comprises sequence complementary to a target gene mutation from the minimum number of target gene mutations. In some cases, the reaction mixture further comprises reagents for conducting high throughput sequencing.

In yet another aspect, provided herein is a kit comprising a set of primers for amplifying DNA prepared from a liquid biological sample obtained from a subject, wherein the set of primers is directed against a plurality of target genes carrying one or more target gene mutations. In some cases, the plurality of target genes are selected from Tables 1a, 1b, 1c, 2a, 2b, 3a, 3b, 4a, 4b, 5a, 5b, 6a, 6b, 7a, 7b, 8a, 8b, 9a, 9b, 10a, 10b, 11, 12a, 12b, 13, 14a, 14b or any combination thereof. In some cases, the plurality of target genes comprises 5 or more target genes. In some cases, the one or more target gene mutations comprise a minimum number of target gene mutations needed to detect one or more types of cancer in the subject. In some cases, the minimum number of target gene mutations is selected comprising the use of an algorithm. In some cases, the minimum number of target gene mutations is about 10 to about 300. In some cases, the one or more types of cancer are colorectal cancer. In some cases, the one or more target gene mutations comprise the mutations listed in Table 1a-1c. In some cases, the one or more types of cancer are pancreatic cancer. In some cases, the one or more target gene mutations comprise the mutations listed in Table 2a-2b. In some cases, the one or more types of cancer are colorectal cancer and pancreatic cancer. In some cases, the one or more target gene mutations comprise the mutations listed in Table 15. In some cases, the one or more types of cancer is adrenocortical cancer. In some cases, the one or more target gene mutations comprise the mutations listed in Table 3a-3b. In some cases, the one or more types of cancer is melanoma. In some cases, the one or more target gene mutations comprise the mutations listed in Table 4a-4b. In some cases, the one or more types of cancer is cutaneous melanoma. In some cases, the one or more target gene mutations comprise the mutations listed in Table 5a-5b. In some cases, the one or more types of cancer is stomach adenocarcinoma. In some cases, the one or more target gene mutations comprise the mutations listed in Table 6a-6b. In some cases, the one or more types of cancer is bladder cancer. In some cases, the one or more target gene mutations comprise the mutations listed in Table 7a-7b. In some cases, the one or more types of cancer is lung adenocarcinoma. In some cases, the one or more target gene mutations comprise the mutations listed in Table 8a-8b. In some cases, the one or more types of cancer is lung squamous cell carcinoma. In some cases, the one or more target gene mutations comprise the mutations listed in Table 9a-9b. In some cases, the one or more types of cancer is cervical cancer. In some cases, the one or more target gene mutations comprise the mutations listed in Table 10a-10b. In some cases, the one or more types of cancer is ovarian cancer. In some cases, the one or more target gene mutations comprise the mutations listed in Table 11. In some cases, the one or more types of cancer is breast cancer. In some cases, the one or more target gene mutations comprise the mutations listed in Table 12a-12b. In some cases, the one or more types of cancer is leukemia. In some cases, the one or more target gene mutations comprise the mutations listed in Table 13. In some cases, the one or more target gene mutations comprise the mutations listed in Table 14a-14b. In some cases, the liquid biological sample is blood, serum, urine, saliva, sputum, cerebrospinal fluid, lymph, stool, or ejaculate. In some cases, the liquid biological sample is blood. In some cases, the blood is a buffy coat fraction. In some cases, the blood is a plasma fraction. In some cases, the liquid biological sample is serum. In some cases, the DNA is genomic DNA (gDNA) or complementary DNA (cDNA). In some cases, the gDNA is circulating tumor DNA (ctDNA). In some cases, the cDNA is reverse transcribed from extracellular RNA. In some cases, the gDNA is derived from circulating tumor cells or microvesicles. In some cases, the extracellular RNA is derived from exosomes. In some cases, the first set of primers and the second set of primers are an identical set of primers. In some cases, the identical set of primers are complementary to target gene sequences in the one or more target genes carrying one or more target gene mutations that do not carry the target gene mutation. In some cases, the kit further comprises a plurality of labeled probes, wherein each of the plurality of labeled probes is specific for a target gene mutation. In some cases, the plurality of labeled probes is oligonucleotides, wherein each of the plurality of labeled probes comprises sequence complementary to a target gene mutation. In some cases, the kit further comprises reagents for conducting high throughput sequencing. In some cases, the kit further comprises reagents for extracting the DNA from the liquid biological sample. In some cases, the kit further comprises reagents for conducting PCR. In some cases, the kit further comprises reagents for conducting digital PCR. In some cases, the digital PCR is ddPCR.

In still another aspect, provided herein is a method for detecting a plurality of target gene mutations in one or more target genes in a subject, the method comprising: a.) pre-amplifying DNA extracted from a liquid biological sample obtained from the subject using a pre-amplification reaction with a first set of primers directed against the plurality of target gene mutations in the one or more target genes; b.) amplifying the pre-amplified DNA obtain in step a) in an amplification reaction using a second set of primers directed against the plurality of target gene mutations pre-amplified in step a); and c) detecting one or more amplification products from the amplification reaction in step b). In some cases, the plurality of target gene mutations are selected from Tables 1a, 1b, 1c, 2a, 2b, 3a, 3b, 4a, 4b, 5a, 5b, 6a, 6b, 7a, 7b, 8a, 8b, 9a, 9b, 10a, 10b, 11, 12a, 12b, 13, 14a, 14b or any combination thereof. In some cases, the plurality of target gene mutations comprises 5 or more target gene mutations. In some cases, the plurality of target gene mutations comprise a minimum number of target gene mutations needed to detect one or more types of cancer in the subject. In some cases, the minimum number of target gene mutations is selected comprising the use of an algorithm. In some cases, the minimum number of target gene mutations is about 10 to about 300. In some cases, the one or more types of cancer is colorectal cancer. In some cases, the one or more target gene mutations comprise the mutations listed in Table 1a-c. In some cases, the one or more types of cancer is pancreatic cancer. In some cases, the one or more target gene mutations comprise the mutations listed in Table 2a-2b. In some cases, the one or more types of cancer is colorectal cancer and pancreatic cancer. In some cases, the one or more target gene mutations comprise the mutations listed in Table 15. In some cases, the one or more types of cancer is adrenocortical cancer. In some cases, the one or more target gene mutations comprise the mutations listed in Table 3a-3b. In some cases, the one or more types of cancer is melanoma. In some cases, the one or more target gene mutations comprise the mutations listed in Table 4a-4b. In some cases, the one or more types of cancer is cutaneous melanoma. In some cases, the one or more target gene mutations comprise the mutations listed in Table 5a-5b. In some cases, the one or more types of cancer is stomach adenocarcinoma. In some cases, the one or more target gene mutations comprise the mutations listed in Table 6a-6b. In some cases, the one or more types of cancer is bladder cancer. In some cases, the one or more target gene mutations comprise the mutations listed in Table 7a-7b. In some cases, the one or more types of cancer is lung adenocarcinoma. In some cases, the one or more target gene mutations comprise the mutations listed in Table 8a-8b. In some cases, the one or more types of cancer is lung squamous cell carcinoma. In some cases, the one or more target gene mutations comprise the mutations listed in Table 9a-9b. In some cases, the one or more types of cancer is cervical cancer. In some cases, the one or more target gene mutations comprise the mutations listed in Table 10a-10b. In some cases, the one or more types of cancer is ovarian cancer. In some cases, the one or more target gene mutations comprise the mutations listed in Table 11. In some cases, the one or more types of cancer is breast cancer. In some cases, the one or more target gene mutations comprise the mutations listed in Table 12a-12b. In some cases, the one or more types of cancer is leukemia. In some cases, the one or more target gene mutations comprise the mutations listed in Table 13. In some cases, the one or more types of cancer is liver cancer. In some cases, the one or more target gene mutations comprise the mutations listed in Table 14a-14b. In some cases, the liquid biological sample is blood, serum, urine, saliva, sputum, cerebrospinal fluid, lymph, stool, or ejaculate. In some cases, the liquid biological sample is blood. In some cases, the blood is a buffy coat fraction. In some cases, the blood is a plasma fraction. In some cases, the liquid biological sample is serum. In some cases, the DNA is genomic DNA (gDNA) or complementary DNA (cDNA). In some cases, the gDNA is circulating tumor DNA (ctDNA). In some cases, the cDNA is reverse transcribed from extracellular RNA. In some cases, the gDNA is derived from circulating tumor cells or microvesicles. In some cases, the extracellular RNA is derived from exosomes. In some cases, the first set of primers and the second set of primers are an identical set of primers. In some cases, the identical set of primers are complementary to target gene sequences in the one or more target genes.

BRIEF DESCRIPTION OF THE DRAWINGS

The skilled artisan will understand that the drawings are for illustration purposes only. The drawings are not intended to limit the scope of the present invention in any way. Novel features are set forth with particularity in the appended claims. A better understanding of the features and advantages will be obtained by reference to the following detailed description that sets forth illustrative embodiments, in which the principles are utilized, and the accompanying drawings of which:

FIG. 1A illustrates methods for selecting tumor mutations for inclusion in genomic target matrices for use in the methods provided herein for detecting cancer (i.e., Step 1: genomic target matrices) as well as methods for obtaining biological samples (e.g., blood) from a subject and extracting nucleic acid (e.g., cell-free DNA) therefrom (i.e., Step 2: DNA extraction from blood). FIG. 1B illustrates methods employed from amplifying (i.e., Step 3: DNA amplification) and detecting (i.e., Step 4: DNA analysis across all targets) mutations included in the genomic target matrices from the extracted nucleic acid.

FIGS. 2A-2D illustrate that amplification with wild-type gene specific primers and probes directed against BRAF V600 COSM 476 (c.1799T>A) (FIG. 2A), KRAS 12D (c.35G>A) (FIG. 2B), KRAS 13D (c.38G>A) (FIG. 2C), or APC 450 (FIG. 2D) mutations yielded no amplification products in cfDNA isolated from a blood sample from a healthy individual whether or not excess copies of wildtype sequence were spiked (FIG. 2A) or not spiked (FIGS. 2B-2D) in the detection assay as described in Example 2. In contrast, FIG. 2E illustrates amplification and detection of a specific target gene mutation (i.e., TP53 R175H COSM 10648 (c.524G>A)) with primers directed against said target gene (TP53) and a probe directed against said target gene mutation at a limit of detection of 10 copies/sample in cfDNA isolated from blood of a healthy individual where wildtype forms of said target gene have been spiked in the sample as described in Example 2.

DETAILED DESCRIPTION OF THE INVENTION

I. General Terminology

Figure 1A:
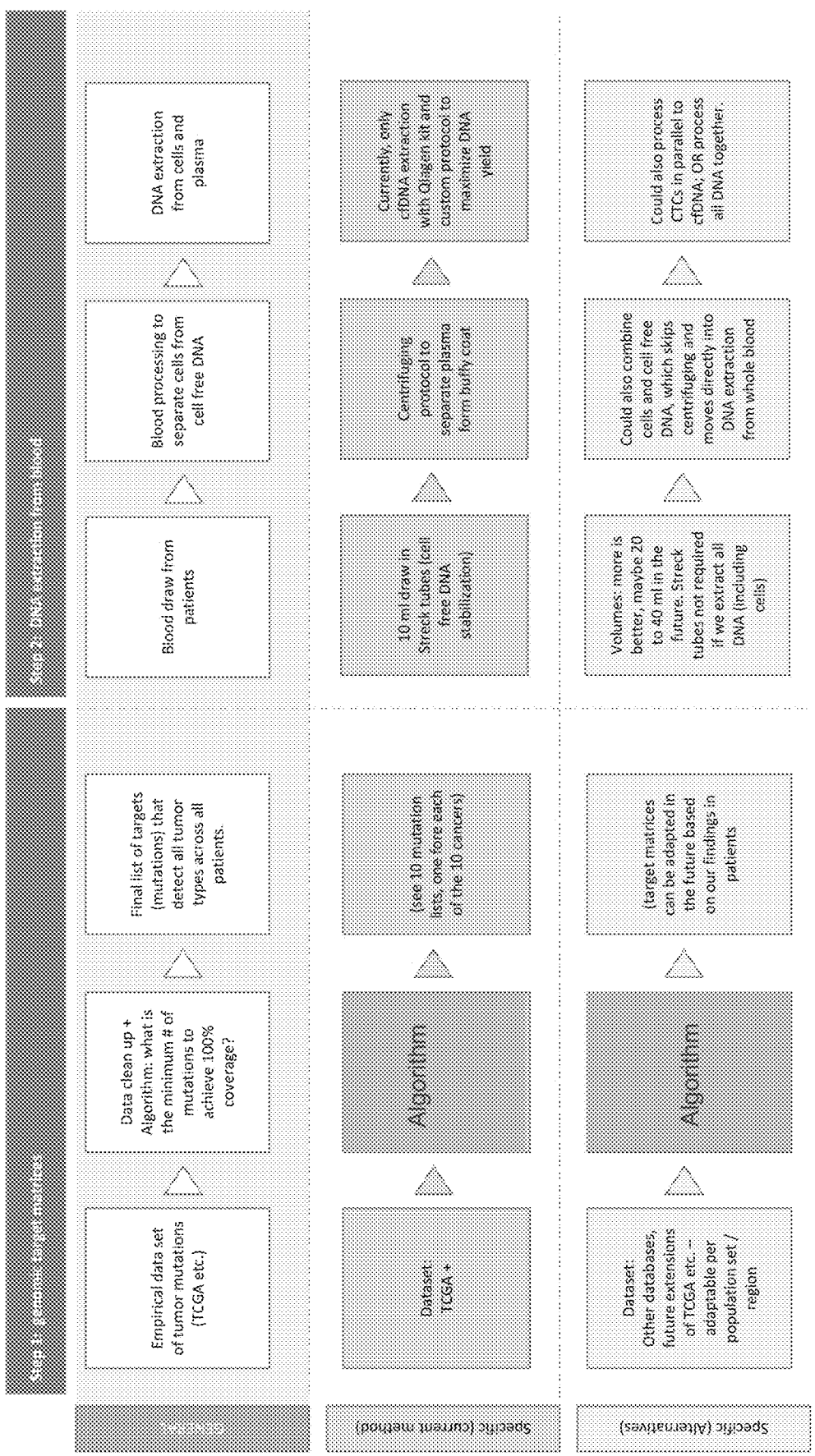
FIG. 1A-B illustrates an overview of process for detecting the presence of one or more mutations in a gene associated with cancer in a sample obtained from a subject.

As used herein, the singular forms "a", "an" and "the" are intended to include the plural forms as well, unless the context clearly indicates otherwise. Additionally, the use of "or" is intended to include "and/or" unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The term "about" as used herein can refer to a range that is 15%, 10%, 8%, 6%, 4%, or 2% plus or minus from a stated numerical value.

As used herein, a "patient" or "subject" can be used interchangeably and can include a mammal. The mammal can be e.g., any mammal, e.g., a human, primate, bird, mouse, rat, fowl, dog, cat, cow, horse, goat, camel, sheep or a pig. In many cases, the mammal is a human being.

As used herein, the term "sample" refers to anything which may contain an analyte for which an analyte assay is desired. An analyte assay can be a detection or diagnostic method as provided herein. In some cases, the analyte is a cell-free or extracellular nucleic acid. In some cases, the analyte is a circulating tumor nucleic acid. The nucleic acid can be such DNA or RNA. In some cases, the nucleic acid is cell-free DNA (cfDNA). The cfDNA can be circulating tumor DNA (ctDNA). The sample can be a biological sample, such as a liquid biological sample or bodily fluid or a biological tissue. Examples of liquid biological samples or bodily fluids for use in the methods provided herein can include urine, blood, plasma, serum, saliva, ejaculate, stool, sputum, cerebrospinal fluid (CSF), tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

The sample can be processed to render it competent for fragmentation, ligation, denaturation, and/or amplification. Exemplary sample processing can include lysing cells of the sample to release nucleic acid, purifying the sample (e.g., to isolate nucleic acid from other sample components, which can inhibit enzymatic reactions), diluting/concentrating the sample, and/or combining the sample with reagents for further nucleic acid processing. In some examples, the sample can be combined with a restriction enzyme, reverse transcriptase, or any other enzyme of nucleic acid processing.

The methods, compositions, reaction mixtures or kits described herein can be used for analyzing or detecting one or more target nucleic acids. The nucleic acids can be polynucleotides. The term polynucleotide or nucleic acid, or grammatical equivalents, can refer to at least two nucleotides covalently linked together. A polynucleotide described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" or LNAs are also included within the definition of nucleic acid analogs. LNAs are a class of nucleic acid analogues in which the ribose ring is "locked" by a methylene bridge connecting the 2'-O atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some cases. The polynucleotides can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. In one embodiment, the primers for use the methods, compositions, kits and reaction mixtures provided herein can comprise one or more LNAs. In one embodiment, the probes for use the methods, compositions, kits and reaction mixtures provided herein can comprise one or more LNAs.

In one embodiment, both the primers and the probes for use the methods, compositions, kits and reaction mixtures provided herein can comprise one or more LNAs.

As used herein, "oligonucleotide" can refer to a polynucleotide chain, typically less than 200 residues long, most typically between 15 and 100 nucleotides long, but also intended to encompass longer polynucleotide chains. Oligonucleotides may be single- or double-stranded. The terms "primer", and "oligonucleotide primer", as used herein, can refer to an oligonucleotide capable of hybridizing to a complementary nucleotide sequence.

As used herein, "hybridization"/"hybridizing" and "annealing" can be used interchangeably and refer to the pairing of complementary nucleic acids or sequences within nucleic acids. "Primer", as used herein, can refer to an oligonucleotide, generally with a free 3' hydroxyl group that is capable of hybridizing with a template (such as a target polynucleotide or target sequence within a polynucleotide, target DNA, target RNA or a primer extension product) and is also capable of promoting polymerization of a polynucleotide complementary to the template. A primer may contain a non-hybridizing sequence that constitutes a tail of the primer. A primer may still be hybridizing to a target even though its sequences are not fully complementary to the target. In some cases, a first and/or second primer used to amplify a nucleic acid or polynucleotide as provided herein further comprise one or more identifier sequences. In some cases, the identifier sequences comprise a non-hybridizable tail on the first and/or second primer. The identifier sequence can be a universal sequence, an adaptor sequence, barcode sequence, a flow cell sequence, and/or an index sequence. In some cases, the index sequence is a Truseq primer sequence compatible with the next generation sequencing (NGS) platform produced by Illumina. In some cases, the first and/or second primer can bind to a solid surface. The solid surface can be a planar surface or a bead. The planar surface can be the surface of a chip, microarray, well, or flow cell. In some cases, the first and/or second primer comprises one or more sequence elements wherein products of the amplification reaction (i.e. amplification products) bind to a solid surface, whereby the one or more sequences elements are complementary to one or more capture probes attached to a solid surface.

The primers described herein can generally be oligonucleotides that are employed in an extension reaction by a polymerase along a template (such as a target polynucleotide or target sequence within a polynucleotide, target DNA, target RNA or a primer extension product), such as in PCR or cDNA synthesis, for example. An oligonucleotide primer can be a synthetic polynucleotide that is single stranded, containing a sequence at its 3'-end that is capable of hybridizing with a sequence of a target polynucleotide. Normally, the 3' region of the primer that hybridizes with the target nucleic acid has at least 80%, 90%, 95%, 100% complementarity to a sequence or primer binding site.

"Complementary", as used herein, can refer to complementarity to all or only to a portion of a sequence. The number of nucleotides in the hybridizable sequence of a specific oligonucleotide primer can be such that stringency conditions used to hybridize the oligonucleotide primer can prevent excessive random non-specific hybridization. In some cases, the number of nucleotides in the hybridizing portion of the oligonucleotide primer can be at least as great as the defined sequence on the target polynucleotide that the oligonucleotide primer hybridizes to, namely, at least 5, at least 6, at least 7, at least 8, at least 9, at least 10, at least 11, at least 12, at least 13, at least 14, at least 15, at least about 20, and generally from about 6 to about 10 or 6 to about 12 of 12 to about 200 nucleotides, usually about 10 to about 50 nucleotides. In general, the target polynucleotide can be larger than the oligonucleotide primer or primers as described previously.

In some cases, the identity of the investigated target polynucleotide sequence is known, and hybridizable primers can be synthesized precisely according to the antisense sequence of the aforesaid target polynucleotide sequence. In other cases, when the target polynucleotide sequence is unknown, the hybridizable sequence of an oligonucleotide primer is a random sequence. Oligonucleotide primers comprising random sequences may be referred to as "random primers", as described below. In yet other cases, an oligonucleotide primer such as a first primer or a second primer comprises a set of primers such as for example a set of first primers or a set of second primers. In some cases, the set of first or second primers may comprise a mixture of primers designed to hybridize to a plurality (e.g. 2, 3, 4, about 6, 8, 10, 20, 40, 80, 100, 125, 150, 200, 250, 300, 400, 500, 600, 800, 1000, 1500, 2000, 2500, 3000, 4000, 5000, 6000, 7000, 8000, 10,000, 20,000, 25,000, 30,000, 40,000, 50,000, 60,000, 70,000, 80,000, 90,000, 100,000 or more) of target sequences. In some cases, the plurality of target sequences may comprise a group of related sequences, random sequences, a whole transcriptome or fraction (e.g. substantial fraction) thereof, or any group of sequences such as mRNA or cfDNA.

"Barcode" can refer to a known polynucleotide sequence that allows some feature of a polynucleotide with which the barcode is associated to be identified. In some cases, the feature of the polynucleotide to be identified is the sample from which the polynucleotide is derived. In some cases, barcodes are at least 3, 4, 5, 6, 7, 8, 9, 10, 11, 12, 13, 14, 15, or more nucleotides in length. In some cases, barcodes are shorter than 10, 9, 8, 7, 6, 5, or 4 nucleotides in length. An oligonucleotide (e.g., primer or adaptor) can comprise about, more than, less than, or at least 1, 2, 3, 4, 5, 6, 7, 8, 9, or 10 different barcodes. In some cases, barcodes associated with some polynucleotides are of different length than barcodes associated with other polynucleotides. Barcodes can be of sufficient length and comprise sequences that can be sufficiently different to allow the identification of samples based on barcodes with which they are associated. In some cases, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some cases, each barcode in a plurality of barcodes differ from every other barcode in the plurality at at least three nucleotide positions, such as at least 3, 4, 5, 6, 7, 8, 9, 10, or more positions. In some cases, an oligonucleotide (e.g., adaptor or primer) comprises at least one of a plurality of barcode sequences. In some cases, barcodes for a second oligonucleotide (e.g., adaptor or primer) are selected independently from barcodes for a first oligonucleotide (e.g., adaptor or primer). In some cases, first oligonucleotides (e.g., adaptor or primer) and second oligonucleotides (e.g., adaptor or primer) having barcodes are paired, such that oligonucleotides (e.g., adaptors or primers) of the pair comprise the same or different one or more barcodes. In some cases, the methods described herein further comprise identifying the sample from which a target polynucleotide is derived based on a barcode sequence to which the target polynucleotide is joined. A barcode can comprise an oligonucleotide sequence that when joined to a target polynucleotide serves as an identifier of the sample from which the target polynucleotide was derived.

RNA-dependent DNA polymerases for use in the methods and compositions provided herein can be capable of effecting extension of a primer according to the methods provided herein. Accordingly, an RNA-dependent DNA polymerase can be one that is capable of extending a nucleic acid primer along a nucleic acid template that is comprised at least predominantly of ribonucleotides. Suitable RNA-dependent DNA polymerases for use in the methods, compositions, and kits provided herein include reverse transcriptases (RTs). RTs are well known in the art. Examples of RTs include, but are not limited to, Moloney murine leukemia virus (M-MLV) reverse transcriptase, human immunodeficiency virus (HIV) reverse transcriptase, rous sarcoma virus (RSV) reverse transcriptase, avian myeloblastosis virus (AMV) reverse transcriptase, rous associated virus (RAV) reverse transcriptase, and myeloblastosis associated virus (MAV) reverse transcriptase or other avian sarcoma-leukosis virus (ASLV) reverse transcriptases, and modified RTs derived therefrom. See e.g. U.S. Pat. No. 7,056,716. Many reverse transcriptases, such as those from avian myeoloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a RT which lacks or has substantially reduced RNase H activity. RTs devoid of RNase H activity are known in the art, including those comprising a mutation of the wild type reverse transcriptase where the mutation eliminates the RNase H activity. Examples of RTs having reduced RNase H activity are described in US20100203597. In these cases, the addition of an RNase H from other sources, such as that isolated from *E. coli*, can be employed for the degradation of the starting RNA sample and the formation of the double stranded cDNA. Combinations of RTs can also contemplated, including combinations of different non-mutant RTs, combinations of different mutant RTs, and combinations of one or more non-mutant RT with one or more mutant RT.

DNA-dependent DNA polymerases for use in the methods and compositions provided herein can be capable of effecting extension of a primer according to the methods provided herein. Accordingly, a DNA-dependent DNA polymerase can be one that is capable of extending a nucleic acid primer along a first strand cDNA in the presence of the RNA template or after selective removal of the RNA template. Exemplary DNA dependent DNA polymerases suitable for the methods provided herein include but are not limited to Klenow polymerase, with or without 3'-exonuclease, Bst DNA polymerase, Bca polymerase, φ29 DNA polymerase, Vent polymerase, Deep Vent polymerase, Taq polymerase, T4 polymerase, and *E. coli* DNA polymerase 1, derivatives thereof, or mixture of polymerases. In some cases, the polymerase does not comprise a 5'-exonuclease activity. In other cases, the polymerase comprises 5' exonuclease activity. In some cases, the primer extension can be performed using a polymerase comprising strong strand displacement activity such as for example Bst polymerase. In other cases, the primer extension can be performed using a polymerase comprising weak or no strand displacement activity. One skilled in the art can recognize the advantages and disadvantages of the use of strand displacement activity during the primer extension step, and which polymerases can be expected to provide strand displacement activity (see e.g., New England Biolabs Polymerases). For example, strand displacement activity can be useful in ensuring whole transcriptome coverage during the random priming and extension step. Strand displacement activity can further be useful in the generation of double stranded amplification products during the priming and extension step. Alternatively, a polymerase which comprises weak or no strand displacement activity can be useful in the generation of single stranded nucleic acid products during primer hybridization and extension that can be hybridized to the target nucleic acid.

II. Overview

The present disclosure includes biomarkers, methods, reagents, and kits for the detection of gene mutations associated with cancer in bodily fluids to aid in the diagnosis, prognosis, and/or theranosis of one or more types of cancer. As such, the present disclosure is based in part on the discovery that gene mutations associated with neoplastic disease (e.g., cancer) and other diseases can be accurately detected from circulating tumor cells (CTCs), microvesicles or exosomes and/or as cell-free DNA (cfDNA) in bodily fluids (e.g., blood). Thus, the present disclosure provides for methods, compositions, mixtures and kits for detecting mutations in nucleic acids that are associated with one or more types of cancer. The methods provided herein can have clinical applications in providing a diagnosis, prognosis or theranosis of one or more types of cancer in a subject with increased sensitivity and specificity.

In some embodiments, a method is provided for detecting the presence of one or more mutations in one or more genes in a bodily fluid obtained from a subject. The one or more mutations in one or more genes can be selected from any of the genes provided herein such as, for example, any of the mutations in Tables 1a-1c, 2a, 2b, 3a, 3b, 4a, 4b, 5a, 5b, 6a, 6b, 7a, 7b, 8a, 8b, 9a, 9b, 10a, 10b, 11, 12a, 12b or 13. The detection of the one or more mutations can indicate that the subject has one or more types of cancer. In some cases, the methods provided herein detect the presence of one or more mutant forms of a gene in a bodily fluid with a specificity of greater than or equal to 55%, 60%, 65%, 70%, 75%, 80%, 85%, 90%, 95%, 99% or 99.9%. In some cases, the methods provided herein detect the presence of one or more mutant forms of a gene in a bodily fluid with a sensitivity of greater than or equal to 20%, 25%, 30%, 35%, 40%, 45%, 50%, 55%, 60%, 65%, 70%, 75%, 80%, 85%, 90%, 95%, 99% or 99.9%. In some cases, the methods provided herein detect the presence of one or more mutant forms of a gene in a bodily fluid in a subject with a sensitivity and/or specificity of greater than any other assay known in the art for detecting nucleic acids in a bodily fluid. In some cases, the methods provided herein detect or diagnose the presence of one or more types of cancer with a specificity of greater than or equal to 50%, 55%, 60%, 65%, 70%, 75%, 80%, 85%, 90%, 95%, 99% or 99.9%. In some cases, the methods provided herein detect or diagnose the presence of one or more types of cancer with a sensitivity of greater than or equal to 20%, 25%, 30%, 35%, 40%, 45%, 50%, 55%, 60%, 65%, 70%, 75%, 80%, 85%, 90%, 95%, 99% or 99.9%. In some cases, the methods provided herein detect or diagnose the presence of one or more types of cancer in a subject with a sensitivity and/or specificity of greater than any other diagnostic cancer assay known in the art.

In one embodiment, the methods, reaction mixtures, kits and compositions provided herein are used to detect the presence of one or more (i.e., a plurality of) mutations in one or more (i.e., a plurality of) target genes in a bodily fluid obtained from a subject that permits the early detection of cancer. In one embodiment, the methods, reaction mixtures, kits and compositions provided herein are used to detect the presence of one or more (i.e., a plurality of) mutations in one or more (i.e., a plurality of) target genes that permits the detection of cancer during any stage of cancer. The cancer can be any type of cancer as provided herein. The one or more mutations in the one or more target genes can be selected from Tables 1a-1c, 2a, 2b, 3a, 3b, 4a, 4b, 5a, 5b, 6a, 6b, 7a, 7b, 8a, 8b, 9a, 9b, 10a, 10b, 11, 12a, 12b, 13, 14a, 14b or any combination thereof. The bodily fluid can be any type of bodily fluid as provided herein. The early detection can be before the onset or detection of one or more symptoms associated with the particular type of cancer. The stage of cancer can be stage I, II, III or IV. The detection of the one or more mutations in the bodily fluid can facilitate a type of therapeutic intervention as provided herein.

In some cases, the method comprises selecting one or more target mutations in one or more target genes, obtaining nucleic acid from a sample of a bodily fluid from a subject, subjecting the nucleic acid to a pre-amplification reaction using primers directed against the one or more target mutations in the one or more target genes, subjecting nucleic acid products obtained from the pre-amplification reaction to a subsequent amplification reaction, and detecting the presence of the one or more target mutations in the one or more target genes within the amplification products from the amplification reaction, whereby the presence of the one or more target mutations within the nucleic amplification products from the amplification reaction is indicative of the subject having the one or more types of cancer. In some cases, the primers used in the pre-amplification reaction are the same or are identical to the primers used in the subsequent amplification reaction. In some cases, the primers used in the pre-amplification reaction comprise a 5'-tail comprising sequence that is non-complementary to the one or more target mutations such that the non-complementary sequence comprises a known or universal sequence. In some cases, the second amplification reaction uses primers directed the known or universal sequence. In some cases, detection of the one or more target gene mutations is performed by using probes directed against the one or more target gene mutations during the amplification reaction. In some cases, detection of the one or more target gene mutations is performed by using primers in the amplification reaction that are directed against the one or more target gene mutations.

In some embodiments, target gene mutations for use in the invention described herein are from target genes selected from Kirsten rat sarcoma viral oncogene homolog (KRAS), tumor protein p53 (TP53), GNAS complex locus (GNAS), Oxysterol binding protein-like 9 (OSBPL9), Teneurin transmembrane protein 2 (TENM2), ATPase secretory pathway Ca2+ transporting 1 (ATP2C1), Hematopoietic cell-specific Lyn substrate 1 (HCLS1), Protocadherin Alpha 7 (PCDHA7), TATA Box Binding Protein (TBP), Interferon Regulatory Factor 5 (IRF5), Transmembrane Protease, Serine 13 (TMPRSS13), Mastermind-Like Transcriptional Coactivator 2 (MAML2), Leucine Rich Repeat Containing 43 (LRRC43), Family With Sequence Similarity 194, Member B (FAM194B), Rho GTPase Activating Protein 5 (ARHGAP5), Mesoderm Posterior BHLH Transcription Factor 2 (MESP2), Tektin 5 (TEKT5), Keratin Associated Protein 4-5 (KRTAP4-5), Arachidonate 12-Lipoxygenase (ALOX12), Solute Carrier Family 5 (Sodium/Sugar Cotransporter), Member 10 (SLC5A10), Histidine Rich Calcium Binding Protein (HRC), Neurofilament, Heavy Polypeptide (NEFH), Opioid Receptor, Delta 1 (OPRD1), Neurotensin Receptor 2

(NTSR2), Zinc Finger Protein 707 (ZNF707), Leucine Rich Adaptor Protein 1-Like (LURAP1L), Mucin 6, Oligomeric Mucus/Gel-Forming (MUC6), Family With Sequence Similarity 194, Member A (FAM194), Protein Phosphatase, Mg2+/Mn2+ Dependent, 1E (PPM1E), Zinc Finger Protein 787 (ZNF787), and/or Collagen, Type XVIII, Alpha 1 (COL18A1), nucleophosmin (NPM1), U2 small nuclear RNA auxiliary factor 1 (U2AF1), neuroblastoma RAS viral oncogene (NRAS), DNA methyltransferase 3 alpha (DNMT3A), ankyrin repeat and BTB domain containing 1 (ABTB1), RB binding protein 4, chromatin remodeling factor (RBBP4), phosphatidylinositol-4,5-bisphosphate 3-kinase catalytic subunit alpha (PIK3CA), RNA, 5.8S ribosomal pseudogene 6 (RNA5-8SP6), RNA binding motif protein, X-linked (RBMX), GATA binding protein 3 (GATA3), PRAME family member 7 (PRAMEF7), TATA-box binding protein associated factor, RNA polymerase I subunit B (TAF1B), chromosome 9 open reading frame 43 (C9orf43), golgin A6 family-like 6 (GOLGA6L6), keratin associated protein 5-1 (KRTAP5-1), cadherin 1 (CDH1), ELAV like RNA binding protein 3 (ELAVL3), FSHD region gene 1 family member B, pseudogene (FRG1BP), SET domain bifurcated 1 (SETDB1), erb-b2 receptor tyrosine kinase 2 (ERBB2), erb-b2 receptor tyrosine kinase 3 (ERBB3), ciliary rootlet coiled-coil, rootletin pseudogene 2 (CROCCP2), chromodomain helicase DNA binding protein 4 (CHD4), parathyroid hormone like hormone (PTHLH), dynamin 1 pseudogene 46 (DNM1P46), patched 2 (PTCH2), olfactory receptor family 2 subfamily T member 35 (OR2T35), tensin 1 (TNS1), UDP-glucuronate decarboxylase 1 (UXS1), mitogen-activated protein kinase 1 (MAPK1), ectonucleoside triphosphate diphosphohydrolase 4 (ENTPD4), E1A binding protein p300 (EP300), neuroblastoma breakpoint family member 1 (NBPF1), YEATS domain containing 2 (YEATS2), zinc finger DHHC-type containing 11 (ZDHHC11), phosphatase and tensin homolog (PTEN), collagen type XI alpha 1 chain (COL11A1), obscurin like 1 (OBSL1), A gene on chromosome 6p21.3 that encodes a subunit of H+-ATPase (ATP6VOE2), chorionic somatomammotropin hormone like 1 (CSHL1), zinc finger BED-type containing 4 (ZBED4), dual specificity phosphatase 10 (DUSP10), tyrosine kinase with immunoglobulin like and EGF like domains 1 (TIE), SEC22 homolog B, vesicle trafficking protein (gene/pseudogene) (SEC22B), histone cluster 2 H2A family member c (HIST2H2AC), vacuolar protein sorting 45 homolog (VPS45), death effector domain containing (DEDD), signal transducing adaptor molecule 2 (STAM2), MAP3K20 antisense RNA 1 (MLK7-AS1), nuclear factor, erythroid 2 like 2 (NFE2L2), aldehyde oxidase 2 pseudogene (AOX2P), glutamate ionotropic receptor delta type subunit 2 (GRID2), protocadherin alpha 13 (PCDHA13), spectrin alpha, non-erythrocytic 1 (SPTAN1), tubulin tyrosine ligase like 5 (TTLL5), formin like 1 (FMNL1), immunoglobulin lambda variable 2-28 (pseudogene) (IGLV2-28), LAS1 like, ribosome biogenesis factor (LAS1L), ubiquitin specific peptidase like 1 (USPL1), complement factor H related 5 (CFHR5), SID1 transmembrane family member 1 (SIDT1), endothelin converting enzyme 2 (ECE2), solute carrier family 4 member 9 (SLC4A9), Fer3 like bHLH transcription factor (FERD3L), zinc finger protein 16 (ZNF16), AKT serine/threonine kinase 1 (AKT1), junction plakoglobin (JUP), methyl-CpG binding domain protein 3 (MBD3), U2 small nuclear RNA auxiliary factor 1 (U2AF1), diacylglycerol kinase delta (DGKD), ankyrin repeat domain 12 (ANKRD12), VENT homeobox pseudogene 7 (VENTXP7), cyclin dependent kinase inhibitor 2A (CDKN2A), notch 2 N-terminal like (NOTCH2NL), olfactory receptor family 2 subfamily T member 2 (OR2T2), nebulin (NEB), transmembrane protease, serine 11F (TMPRSS11F), X-prolyl aminopeptidase 1 (XPNPEP1), killer cell immunoglobulin like receptor, two Ig domains and short cytoplasmic tail 4 (KIR2DS4), DS cell adhesion molecule (DSCAM), MAF bZIP transcription factor A (MAFA), heterogeneous nuclear ribonucleoprotein K pseudogene 3 (HNRNPKP3), zinc finger ZZ-type containing 3 (ZZZ3), potassium calcium-activated channel subfamily N member 3 (KCNN3), pyrin and HIN domain family member 1 (PYHIN1), additional sex combs like 2, transcriptional regulator (ASXL2), coiled-coil domain containing 121 (CCDC121), tetratricopeptide repeat domain 27 (TTC27), ZFP36 ring finger protein like 2 (ZFP36L2), protein tyrosine phosphatase, non-receptor type 18 (PTPN18), chromosome 3 open reading frame 30 (C3orf30), F-box and WD repeat domain containing 7 (FBXW7), hyperpolarization activated cyclic nucleotide gated potassium channel 1 (HCN1), ring finger protein 5 (RNF5), epidermal growth factor receptor (EGFR), family with sequence similarity 135 member B (FAM135B), ST8 alpha-N-acetyl-neuraminide alpha-2,8-sialyltransferase 6 (ST8SIA6), phosphatase and tensin homolog (PTEN), ankyrin repeat domain 20 family member A9, pseudogene (ANKRD20A9P), nuclear receptor coactivator 6 (NCOA6), APC membrane recruitment protein 3 (AMER3), LDL receptor related protein 1B (LRP1B), titin (TTN), fibroblast growth factor receptor 3 (FGFR3), gamma-aminobutyric acid type B receptor subunit 1 (GABBR1), BMS1, ribosome biogenesis factor (BMS1), Ras association domain family member 2 (RASSF2), ankyrin repeat domain 30B pseudogene 2 (ANKRD30BP2), POU class 4 homeobox 2 (POU4F2), B-Raf proto-oncogene, serine/threonine kinase (BRAF), TBC1 domain family member 3 pseudogene 2 (TBC1D3P2), EMG1, N1-specific pseudouridine methyltransferase (EMG1), breakpoint cluster region pseudogene 7 (BCRP7), H3 histone, family 3A, pseudogene 4 (H3F3AP4), FTX transcript, XIST regulator (non-protein coding) (FTX), BMS1, ribosome biogenesis factor pseudogene 20 (BMS1P20), B melanoma antigen family member 2 (BAGE2), Fanconi anemia complementation group D2 (FANCD2), tumor suppressing subtransferable candidate 2 pseudogene (TSSC2), pyridoxal dependent decarboxylase domain containing 2, pseudogene (PDXDC2P), long intergenic non-protein coding RNA 264 (LINC00264), zinc finger protein 733, pseudogene (ZNF733P), ankyrin repeat domain 20 family member A14, pseudogene (ANKRD20A14P), MLLT3, super elongation complex subunit (MLLT3), neuroblastoma breakpoint family member 10 (NBPF10), keratin associated protein 4-11 (KRTAP4-11), (NBPF1), synapsin II (SYN2), RANBP2-like and GRIP domain containing 3 (RGPD3), archaelysin family metallopeptidase 2 pseudogene 1 (AMZ2P1), lysine demethylase 6A (KDM6A), ankyrin repeat domain 20 family member A12, pseudogene (ANKRD20A12P), dynamin 1 pseudogene 47 (DNM1P47), ERCC excision repair 2, TFIIH core complex helicase subunit (ERCC2), immunoglobulin heavy variable 1/OR16-3 (pseudogene) (IGHV1OR16-3), B melanoma antigen family member 2 (BAGE2), gamma-glutamyltransferase 3 pseudogene (GGT3P), transmembrane and coiled-coil domains 2 (TMCO2), splicing factor 3b subunit 1 (SF3B1), glutamate dehydrogenase 1 pseudogene 7 (GLUD1P2), succinate dehydrogenase complex flavoprotein subunit A pseudogene 1 (SDHAP1), PR/SET domain 9 (PRDM9), chaperonin containing TCP1 subunit 6 pseudogene 1 (CCT6P1), PEAK1 related kinase activating pseudokinase 1 (SGK223), retinoid X receptor alpha (RXRA), leucine rich repeat containing 37 member A17, pseudogene (LRRC37A17P), ankyrin repeat domain 30B pseudogene 2 (ANKRD30BP2), tumor suppressing subtransferable candidate 2 pseudogene (TSSC2), family with sequence similarity 47 member C (FAM47C), aryl hydrocarbon receptor (AHR), ring finger protein 43 (RNF43), TSPO associated protein 1 (BZRAP1), proteasome activator subunit 4 (PSME4), KIAA1324 like (KIAA1324L), family with sequence similarity 46 member D (FAM46D), potassium calcium-activated channel subfamily M regulatory beta subunit 2 (KCNMB2), regulating synaptic membrane exocytosis 1 (RIMS1), family with sequence similarity 135 member B (FAM135B), cadherin 11 (CDH11), small nuclear RNA activating complex polypeptide 2 (SNAPC2), spectrin alpha, erythrocytic 1 (SPTA1), microtubule associated tumor suppressor candidate 2 (MTUS2), xylosyltransferase 2 (XYLT2), phosphoglucomutase 5 (PGM5), zinc finger and BTB domain containing 20 (ZBTB20), AT-rich interaction domain 1A (ARID1A), zinc finger protein 43 (ZNF43), formin homology 2 domain containing 3 (FHOD3), lectin, mannose binding 1 (LMAN1), ubiquitin specific peptidase 34 (USP34), ATPase H+ transporting V subunit B 1 (ATP6V1B1), glutamate rich 6B (ERICH6B), APC, WNT signaling pathway regulator (APC), tetrapeptide repeat homeobox 1 (TPRX1), adenosine deaminase domain containing 2 (ADAD2), PHD finger protein 2 (PHF2), AT-rich interaction domain 1B (ARID1B), keratin associated protein 10-2 (KRTAP10-2), zinc finger protein 732 (ZNF732), myomesin 1 (MYOM1), coiled-coil domain containing 185 (CCDC185), solute carrier family 6 member 20 (SLC6A20), collapsin response mediator protein 1 (CRMP1), protocadherin alpha 5 (PCDHA5), HECT domain and ankyrin repeat containing E3 ubiquitin protein ligase 1 (HACE1), teneurin transmembrane protein 4 (TENM4), neuronal differentiation 4 (NEUROD4), DNA polymerase epsilon, catalytic subunit (POLE), dentin sialophosphoprotein (DSPP), zinc finger protein 787 (ZNF787), mucin 4, cell surface associated (MUC4), protocadherin alpha 7 (PCDHA7), beta-1,4-N-acetyl-galactosaminyltransferase 2 (B4GALNT2), glucuronidase, beta pseudogene 1 (GUSBP1), solute carrier family 7 member 2 (SLC7A2), PHD finger protein 2 (PHF2), serine palmitoyltransferase long chain base subunit 3 (SPTLC3), ras-related C3 botulinum toxin substrate 1 (rho family, small GTP binding protein Rac1) (RAC1), KIT proto-oncogene receptor tyrosine kinase (KIT), indolethylamine N-methyltransferase (INMT), BCL2 like 12 (BCL2L12), cyclin dependent kinase inhibitor 2A (CDKN2A), armadillo repeat containing 4 (ARMC4), solute carrier family 27 member 5 (SLC27A5), splicing factor 3b subunit 1 (SF3B1), EPH receptor A6 (EPHA6), roundabout guidance receptor 2 (ROBO2), retinitis pigmentosa GTPase regulator interacting protein 1 (RPGRIP1), sphingomyelin phosphodiesterase 4 (SMPD4), microRNA 3648-1 (MIR3648), nudix hydrolase 11 (NUDT11), olfactory receptor family 4 subfamily X member 2 (OR4X2), TBC1 domain family member 3 pseudogene 2 (TBC1D3P2), ubiquitin protein ligase E3A (UBE3A), dynein axonemal heavy chain 5 (DNAH5), RP1, axonemal microtubule associated (RP1), collagen type V alpha 1 chain (COL5A1), zona pellucida glycoprotein 2 (ZP2), dynein axonemal heavy chain 9 (DNAH9), DNA polymerase delta interacting protein 2 (POLDIP2), G protein subunit alpha 11 (GNA11), potassium voltage-gated channel subfamily H member 5 (KCNH5), zinc finger protein, FOG family member 2 (ZFPM2), zinc finger protein 585B (ZNF585B), C-reactive protein (CRP), solute carrier family 4 member 10 (SLC4A10), keratin 3 (KRT3), isocitrate dehydrogenase (NADP(+)) 1, cytosolic (IDH1), mitogen-activated protein kinase kinase 1 (MAP2K1), kelch domain containing 7A (KLHDC7A), calcium/calmodulin dependent protein kinase IV (CAMK4), thrombospondin type 1 domain containing 7B (THSD7B), regulator of G-protein signaling 7 (RGS7), tumor protein p63 (TP63), olfactory receptor family 2 subfamily A member 5 (OR2A5), G protein subunit alpha 11 (GNA11), G protein subunit alpha q (GNAQ), cysteinyl leukotriene receptor 2 (CYSLTR2), triadin (TRDN), GRB2 associated binding protein 2 (GAB2), E1A binding protein p400 (EP400), zinc finger protein, FOG family member 1 (ZFPM1), ORAI calcium release-activated calcium modulator 1 (ORAI1), cathepsin A (CTSA), ataxin 1 (ATXN1), chromosome 21 open reading frame 58 (C21orf58), nuclear receptor subfamily 1 group H member 2 (NR1H2), ATPase H+ transporting accessory protein 1 (ATP6AP1), potassium calcium-activated channel subfamily N member 2 (KCNN2), Ras and Rab interactor 3 (RIN3), collagen type XVIII alpha 1 chain (COL18A1), family with sequence similarity 46 member A (FAM46A), cysteine rich PAK1 inhibitor (CRIPAK), TGFB induced factor homeobox 1 (TGIF1), family with sequence similarity 120C (FAM120C), telomerase reverse transcriptase (TERT), RP5-857K21.11, catenin beta 1 (CTNNB1), Kruppel like factor 8 (AL353698.1-KLF8), RP1-1151B14.3, mitochondrially encoded NADH:ubiquinone oxidoreductase core subunit 2 pseudogene 28 (MTND2P28), potassium voltage-gated channel subfamily J member 12 (KCNJ12), BEN Domain Containing 6 (BEND6-KIAA1586), Absent In Melanoma 1-Like (AIM1L), RP11-417J8.6, Protein Phosphatase 1 Regulatory Subunit 3A (PPP R3A), Heterogeneous Nuclear Ribonucleoprotein A1 Pseudogene 46 (RP11-463J7.2-HNRNPA1P46), Potassium Voltage-Gated Channel Subfamily H Member 1 (KCNH1), (BMS1P8-ENPP7P13), Lymphoid Enhancer Binding Factor 1 (LEF1), Human DNA sequence from clone RP11-262H14 on chromosome 9(AL512625.1), gamma-aminobutyric acid type A receptor alpha3 subunit (GABRA3), Contactin 5 (CNTN5), *Homo sapiens* chromosome 17, clone hRPK. 394_K_10 (AC006080.1), Thrombospondin Type 1 Domain Containing 7B (THSD7B), Exocyst Complex Component 2 (EXOC2), HLA-DRB1-HLA-DQA1, Filamin C (FLNC), ATP/GTP Binding Protein Like 2 (AGBL2), Thymine-DNA glycosylase (TDG), Exonuclease 3'-5' Domain Containing 1 (EXD1), HIDE1 (C19orf38), RP11-96J15.1, Sterile Alpha Motif Domain Containing 12 (SAMD12), Cytochrome P450 2C9 (RP11-400G3.3-CYP2C9), RNA, U6 Small Nuclear 2 (RNU6-699P-RP11-584P21.2), ribosomal protein S2 pseudogene 25 (RPS2P25-CTD-2036A18.2), Thrombospondin Type 1 Domain Containing 7A (THSD7A), Apolipoprotein H (APOH) or any combination thereof. The mutations of the target genes can be somatic or germline mutations. In some cases, the one or more target gene mutations for use in the methods provided herein are somatic mutations and can include any, a plurality or all mutations listed in Table 1a-1c, 2a, 2b, 3a, 3b, 4a, 4b, 5a, 5b, 6a, 6b, 7a, 7b, 8a, 8b, 9a, 9b, 10a, 10b, 11, 12a, 12b, 13, 14a, 14b or combinations thereof. The plurality of somatic mutations for use in the methods provided herein can be 2, 3, 4, 5, 6, 7, 8, 9, 10, 15, 20, 25, 30, 35, 40, 45, 50, or more somatic mutations from Tables 1a-1c, 2a, 2b, 3a, 3b, 4a, 4b, 5a, 5b, 6a, 6b, 7a, 7b, 8a, 8b, 9a, 9b, 10a, 10b, 11, 12a, 12b, 13, 14a, or 14b.

The one or more target gene mutations can be selected from any database comprising mutations of genes associated with any type of neoplastic disease (i.e., cancer) as provided herein. The databases can be public databases such as for example the Cancer Genome Atlas (TCGA) and/or the International Cancer Genome Consortium (ICGC). Selection of the one or more target gene mutations can be performed by a computer implemented method comprising use of an algorithm applied to one or more datasets retrieved from a database as described herein. The type of cancer can be any type of cancer known in the art and/or provided herein. The empirical data set of gene mutations for the type of cancer can include subtypes of said cancer. The plurality of types of cancer can be about or more than 2, 3, 4, 5, 6, 7, 8, 9, 10, 15, 20 or 25 types of cancer. The plurality of types of cancer can include colorectal cancer, liver cancer, pancreatic cancer, lung cancer (e.g., lung adenocarcinoma, lung squamous cell carcinoma), breast cancer (e.g., invasive ductal carcinoma), stomach cancer, ovarian cancer, leukemia, melanoma, cutaneous melanoma, bladder cancer, cervical cancer, adrenocortical cancer, Hodgkin's lymphoma and non-Hodgkin's lymphoma.

TABLE 1a

Somatic gene mutations associated with colorectal cancer (COAD).

| Chromosome (Chr) | Gene | Mutation | Start | End |
|---|---|---|---|---|
| 3 | HCLS1 | c.1104C > T | 121351315 | 121351315 |
| 5 | PCDHA7 | c.1054C > A | 140215022 | 140215022 |
| 6 | TBP | c.188_189insCAG | 170871012 | 170871012 |
| 6 | TBP | c.216_218delACA | 170871037 | 170871037 |
| 7 | IRF5 | c.572_601del | 128587351 | 128587351 |
| 7 | IRF5 | c.572G > A | 128587374 | 128587374 |
| 9 | PHF2 | c.2962_2963ins | 96439003 | 96439003 |

TABLE 1a-continued

Somatic gene mutations associated with colorectal cancer (COAD).

| Chromosome (Chr) | Gene | Mutation | Start | End |
|---|---|---|---|---|
| 17 | TP53 | c.742C > T | 7577539 | 7577539 |
| 17 | TP53 | c.743G > A | 7577538 | 7577538 |
| 17 | TP53 | c.637C > T | 7578212 | 7578212 |
| 17 | TP53 | c.844C > T | 7577094 | 7577094 |
| 11 | TMPRSS13 | c.248_262del | 117789312 | 117789312 |
| 11 | MAML2 | c.1812_1820del | 95825374 | 95825374 |
| 12 | LRRC43 | c.1552_1553ins | 122685139 | 122685139 |
| 19 | HRC | c.606A > G | 49657889 | 49657889 |
| 17 | SLC5A10 | c.1286_1287ins | 18918509 | 18918509 |
| 22 | NEFH | c.1939_1940ins | 29885566 | 29885566 |
| 22 | NEFH | c.1938 > C | 29885567 | 29885567 |
| 22 | NEFH | c.1965_1988del | 29885580 | 29885580 |
| 22 | NEFH | c.1935A > G | 29885564 | 29885564 |
| 13 | FAM194B | c.413A > G | 46170728 | 46170728 |
| 13 | FAM194B | c.406G > A | 46170735 | 46170735 |
| 13 | FAM194B | c.415T > C | 46170726 | 46170726 |
| 14 | ARHGAP5 | c.1421T > C | 32561296 | 32561296 |
| 15 | MESP2 | c.558G > A | 90320146 | 90320146 |
| 16 | TEKT5 | c.263G > A | 10788468 | 10788468 |
| 17 | KRTAP4-5 | c.245_246ins | 39305774 | 39305774 |
| 17 | ALOX12 | c.123C > G | 6899559 | 6899559 |
| 1 | OPRD1 | c.80G > T | 29138975 | 29138975 |
| 2 | NTSR2 | c.161C > T | 11810095 | 11810095 |
| 8 | ZNF707 | c.525A > G | 144776109 | 144776109 |
| 9 | LURAP1L | c.146_147ins | 12775860 | 12775860 |
| 11 | MUC6 | c.5733G > A | 1017068 | 1017068 |
| 17 | PPM1E | c.99_100ins | 56833456 | 56833456 |
| 19 | ZNF787 | c.1101_1103del | 56599437 | 56599437 |
| 21 | COL18A1 | c.4083_4091del | 46924425 | 46924425 |

TABLE 1b

Somatic gene mutations associated with COAD.

| Chr | Position | Gene | Wildtype | Mutation | dbsnp |
|---|---|---|---|---|---|
| 11 | 117789312 | TMPRSS13 | CGGGCTG GAGATGCCT (SEQ ID NO.: 1) | C | rs201746372 |
| 6 | 170871013 | TBP | A | ACAG | rs201732168 |
| 7 | 140453136 | BRAF | A | T | rs113488022 |
| 12 | 25398284 | KRAS | C | T | rs121913529 |
| 12 | 25398281 | KRAS | C | T | rs112445441 |
| 7 | 128587374 | IRF5 | G | A | rs113806178 |
| 17 | 7577538 | TP53 | C | T | rs11540652 |
| 12 | 25398284 | KRAS | C | A | rs121913529 |
| 13 | 46170728 | ERICH6B | T | C | rs45625342 |
| 22 | 29885567 | NEFH | A | C | rs75808076 |
| 5 | 112175639 | APC | C | T | rs121913332 |
| 11 | 95825374 | MAML2 | TTGCTGCTGC (SEQ ID NO.: 2) | T | rs141671766 |
| 3 | 178936091 | PIK3CA | G | A | rs104886003 |
| 5 | 112116592 | APC | C | T | |
| 17 | 56435160 | RNF43, BZRAP1-AS1 | AC | A | |
| 19 | 48305646 | TPRX1 | G | A | rs112842028 |
| 17 | 56833457 | PPM1E | G | GGAACCC | rs201186780 |
| 16 | 84224967 | ADAD2 | G | A | rs8044695 |
| 9 | 96438998 | PHF2 | T | TACCACCC CTGCCTCC (SEQ ID NO.: 3) | |
| 5 | 112175390 | APC | T | T | rs121913328 |
| 12 | 25398284 | KRAS | C | G | rs121913529 |
| 21 | 45970774 | KRTAP10-2, TSPEAR | G | A | rs76536096 |
| 4 | 265837 | ZNF732 | C | A | |
| 6 | 157527948 | ARID1B | C | T | |
| 18 | 3188882 | MYOM1 | C | T | rs200770047 |
| 5 | 112175480 | APC | G | T | |
| 1 | 52306079 | | T | A | rs62648104 |
| 12 | 25398285 | KRAS | C | T | rs121913530 |
| 5 | 112175423 | APC | C | T | rs121913329 |

TABLE 1b-continued

Somatic gene mutations associated with COAD.

| Chr | Position | Gene | Wildtype | Mutation | dbsnp |
|---|---|---|---|---|---|
| 11 | 95825407 | MAML2 | C | T | rs61901862 |
| 17 | 7577094 | TP53 | G | A | |
| 5 | 112175211 | APC | TAAAAG | T | |
| 1 | 223567909 | CCDC185 | G | A | |
| 3 | 45801358 | SLC6A20 | G | A | |
| 4 | 5838495 | CRMP1 | C | T | |
| 5 | 140203782 | PCDHA5, PCDHA1, PCDHA2, PCDHA3, PCDHA4 | CT | C | |
| 6 | 105198346 | HACE1 | G | A | rs374813736 |
| 11 | 78383150 | TENM4 | G | A | |
| 12 | 55420513 | NEUROD4 | G | A | rs139282092 |
| 12 | 133218935 | POLE | G | A | rs112358554 |
| 1 | 154842199 | KCNN3 | G | GGCTGCTGCTGCTGCT (SEQ ID NO.: 4) | |
| 4 | 88536451 | DSPP | C | T | rs141946550 |
| 22 | 29885564 | NEFH | A | G | rs202065964 |
| 19 | 56599437 | ZNF787 | CTCG | C | rs5828672 |
| 17 | 7578406 | TP53 | C | T | rs28934578 |
| 22 | 29885562 | NEFH | G | A | rs370929798 |
| 3 | 195518112 | MUC4 | T | A | rs75263205 |
| 5 | 140215022 | PCDHA7, PCDHA1, PCDHA2, PCDHA3, PCDHA4, PCDHA5, PCDHA6 | C | A | |
| 4 | 88536448 | DSPP | C | T | rs142168734 |
| 11 | 117789345 | TMPRSS13 | G | C | rs61900347 |
| 13 | 46170737 | ER1CH6B | T | C | rs1117004691 |

TABLE 1c

Somatic gene mutations associated with COAD

| Chr | Position | Gene | Wildtype | Mutation | dbsnp |
|---|---|---|---|---|---|
| 6 | 170871013 | TBP | A | ACAG | rs201732168 |
| 7 | 140453136 | BRAF | A | T | rs113488022 |
| 12 | 25398284 | KRAS | C | T | rs121913529 |
| 12 | 25398284 | KRAS | C | T | rs112445441 |
| 17 | 7577538 | TP53 | C | T | rs11540652 |
| 12 | 25398284 | KRAS | C | A | rs121913529 |
| 13 | 46170728 | ERICH6B | T | C | rs45625342 |
| 22 | 29885567 | NEFH | A | C | rs75808076 |
| 5 | 112175639 | APC | C | T | rs121913332 |
| 3 | 178936091 | PIK3CA | G | A | rs104886003 |
| 5 | 112116592 | APC | C | T | |
| 17 | 56435160 | RNF43, BZRAP1-AS1 | AC | A | |
| 19 | 48305646 | TPRX1 | G | A | rs112842028 |
| 16 | 84224967 | ADAD2 | G | A | rs8044695 |
| 9 | 96438998 | PHF2 | T | TACCACCCCTGCCTCC (SEQ ID NO.: 3) | |
| 5 | 112175390 | APC | C | T | rs121913328 |
| 12 | 25398284 | KRAS | C | G | rs121913529 |
| 4 | 265837 | ZNF732 | C | A | |
| 6 | 157527948 | ARID1B | C | T | |
| 18 | 3188882 | MYOM1 | C | T | rs200770047 |
| 5 | 112175480 | APC | G | T | |
| 1 | 52306079 | | T | A | rs62648104 |
| 12 | 25398285 | KRAS | C | T | rs121913530 |
| 5 | 112175423 | APC | C | T | rs121913329 |
| 11 | 95825407 | MAML2 | C | T | rs61901862 |
| 17 | 7577094 | TP53 | G | A | |
| 4 | 88536451 | DSPP | C | T | rs141946550 |
| 22 | 29885564 | NEFH | A | G | rs202065964 |

TABLE 1c-continued

Somatic gene mutations associated with COAD

| Chr | Position | Gene | Wildtype | Mutation | dbsnp |
|---|---|---|---|---|---|
| 17 | 7578406 | TP53 | C | T | rs28934578 |
| 22 | 29885562 | NEFH | G | A | rs370929798 |
| 3 | 195518112 | MUC4 | T | A | rs75263205 |
| 5 | 140215022 | PCDHA7, PCDHA1, PCDHA2, PCDHA3, PCDHA4, PCDHA5, PCDHA6 | C | A | |
| 4 | 88536448 | DSPP | C | T | rs142168734 |
| 11 | 117789345 | TMPRSS13 | G | C | rs61900347 |
| 13 | 46170737 | ERICH6B | T | C | rs117004691 |

TABLE 2a

Somatic gene mutations associated with pancreatic cancer.

| Chr | Gene | Mutation | Start | End |
|---|---|---|---|---|
| 12 | KRAS | c.35G > A | 25398284 | 25398284 |
| 12 | KRAS | c.35G > T | 25398284 | 25398284 |
| 12 | KRAS | c.34G > C | 25398285 | 25398285 |
| 12 | KRAS | c.183A > C | 25380275 | 25380275 |
| 12 | KRAS | c.183A > T | 25380275 | 25380275 |
| 12 | KRAS | c.34G > T | 25398285 | 25398285 |
| 17 | TP53 | c.817C > T | 7577121 | 7577121 |
| 17 | TP53 | c.743G > A | 7577538 | 7577538 |
| 17 | TP53 | c.524G > A | 7578406 | 7578406 |
| 17 | TP53 | c.844C > T | 7577094 | 7577094 |

TABLE 2a-continued

Somatic gene mutations associated with pancreatic cancer.

| Chr | Gene | Mutation | Start | End |
|---|---|---|---|---|
| 17 | TP53 | c.818G > A | 7577120 | 7577120 |
| 1 | OSBPL9 | c.241 + 5856A > T | 52141040 | 52141040 |
| 20 | GNAS | c.2530C > T | 57484420 | 57484420 |
| 20 | GNAS | c.2531G > A | 57484421 | 57484421 |
| 5 | TENM2 | c.3825 − 22delT | 167638716 | 167638717 |
| 8 | SLC7A2 | c.1315 + 3_1315 + 4delGA | 17412210 | 17412212 |
| 3 | ATP2C1 | c.6 + 44_6 + 46delGTG | 130613662 | 130613665 |
| 16 | RP11-430C1.1-RP11-457D20.1 | n.601769201 > A | 60176920 | 60176920 |
| 5 | GUSBP1 | n.144 + 21543A > G | 21363628 | 21363628 |
| 17 | B4GALNT2 | c.534 − 724A > T | 47229438 | 47229438 |

TABLE 2b

Somatic gene mutations associated with pancreatic cancer

| Chr | Gene | Mutation | Start | End |
|---|---|---|---|---|
| 12 | KRAS | c.35G > A | 25398284 | 25398284 |
| 12 | KRAS | c.35G > T | 25398284 | 25398284 |
| 12 | KRAS | c.34G > C | 25398285 | 25398285 |
| 12 | KRAS | c.183A > C | 25380275 | 25380275 |
| 12 | KRAS | c.183A > T | 25380275 | 25380275 |
| 12 | KRAS | c.34G > T | 25398285 | 25398285 |
| 17 | TP53 | c.817C > T | 7577121 | 7577121 |
| 17 | TP53 | c.743G > A | 7577538 | 7577538 |
| 17 | TP53 | c.524G > A | 7578406 | 7578406 |
| 17 | TP53 | c.844C > T | 7577094 | 7577094 |
| 17 | TP53 | c.818G > A | 7577120 | 7577120 |
| 20 | GNAS | c.2531G > A | 57484421 | 57484421 |
| 5 | TENM2 | c.3825-22delT | 167638716 | 167638717 |
| 8 | SLC7A2 | c.1315 + 3_1315 + 4delGA | 17412210 | 17412212 |

TABLE 3a

Somatic gene mutations associated with Adrenocortical Cancer (ACC)

| Chr | Position | Gene | Wildtype | Mutation | dbsnp |
|---|---|---|---|---|---|
| 16 | 88599696 | ZFPM1 | GAGCCTCTGG (SEQ ID NO.: 5) | G | |
| 12 | 122064773 | ORAI1 | CCCGCCA | C | |
| 20 | 44520237 | CTSA | CCTG | C | rs397839006 |
| 6 | 16327864 | ATXN1 | G | GTGC | |
| 21 | 47721985 | C21orf58 | A | ATGG | rs71318063 |
| 19 | 56599437 | ZNF787 | CTCG | C | rs5828672 |
| 19 | 50881825 | NR1H2 | G | A | rs55817866 |
| 14 | 93154537 | RIN3 | TGGC | T | rs71698059 |
| X | 153657083 | ATP6AP1 | A | G | |
| 5 | 113698631 | KCNN2 | T | TGCC | rs151038013 |
| 21 | 46924425 | COL18A1, SLC19A1 | CGGCCCCCA (SEQ ID NO.: 6) | C | rs149296338 |
| 16 | 88599700 | ZFPM1 | CT | C | rs67322929 |
| 6 | 82461727 | FAM46A | ACCGCCGAAGTCGCCG (SEQ ID NO.: 7) | A | |
| 4 | 1388817 | CRIPAK | C | G | rs200606324 |
| chr18 | 3452222 | TGIF1 | CT | C | rs11571510 |
| chr4 | 1388819 | CRIPAK | T | C | rs144797159 |
| chrX | 54209387 | FAM120C | A | G | |

TABLE 3b

Somatic gene mutations associated with ACC

| Chr | Position | Gene | Wildtype | Mutation | dbsnp |
|---|---|---|---|---|---|
| 16 | 88599696 | ZFPM1 | GAGCCTCTGG (SEQ ID NO.: 5) | G | |
| 12 | 122064773 | ORAI1 | CCCGCCA | C | |
| 20 | 44520237 | CTSA | CCTG | C | rs397839006 |
| 6 | 16327864 | ATXN1 | G | GTGC | |
| 21 | 47721985 | C21orf58 | A | ATGG | rs71318063 |
| 9 | 56599437 | ZNF787 | CTCG | C | rs5828672 |
| 14 | 93154537 | RIN3 | TGGC | T | rs71698059 |
| X | 153657083 | ATP6AP1 | A | G | |
| 16 | 88599700 | ZFPM1 | CT | C | rs67322929 |
| 4 | 1388817 | CRIPAK | C | G | rs200606324 |
| 18 | 3452222 | TGIF1 | CT | C | rs11571510 |
| 4 | 1388819 | CRIPAK | T | C | rs144797159 |
| X | 54209387 | FAM120C | A | G | |

TABLE 4a

Somatic gene mutations associated with Melanoma (UVM)

| Chr | Position | Gene | Wildtype | Mutation | dbsnp |
|---|---|---|---|---|---|
| 19 | 3118942 | GNA11 | A | T | |
| 9 | 80409488 | GNAQ | T | G | |
| 9 | 80409488 | GNAQ | T | A | |
| 13 | 49281339 | CYSLTR2 | T | A | |
| 2 | 198267484 | SF3B1 | G | A | |
| 2 | 198267483 | SF3B1 | C | T | |
| 6 | 123786032 | TRDN | G | GA | |
| 11 | 77937662 | GAB2 | T | G | |
| 12 | 132547087 | EP400 | G | A | rs12366766 |

TABLE 4b

Somatic gene mutations associated with UVM

| Chr | Position | Gene | Wildtype | Mutation | dbsnp |
|---|---|---|---|---|---|
| 19 | 3118942 | GNA11 | A | T | |
| 9 | 80409488 | GNAQ | T | G | |

TABLE 4b-continued

Somatic gene mutations associated with UVM

| Chr | Position | Gene | Wildtype | Mutation | dbsnp |
|---|---|---|---|---|---|
| 9 | 80409488 | GNAQ | T | A | |
| 13 | 49281339 | CYSLTR2 | T | A | |
| 2 | 198267484 | SF3B1 | G | A | |
| 2 | 198267483 | SF3B1 | C | T | |

TABLE 5a

Somatic gene mutations associated with Cutaneous Melanoma (SKCM)

| Chr | Position | Gene | Wildtype | Mutation | dbsnp |
|---|---|---|---|---|---|
| 7 | 140453136 | BRAF | A | T | rs113488022 |
| 1 | 115256529 | NRAS | T | C | rs11554290 |
| 1 | 115256530 | NRAS | G | T | rs121913254 |
| 1 | 115256529 | NRAS | T | A | rs11554290 |
| 20 | 13029765 | SPTLC3 | G | A | rs267605838 |
| 7 | 6426892 | RAC1 | C | T | |
| 4 | 55594221 | KIT | A | G | rs121913512 |
| 7 | 30795310 | INMT, INMT-FAM188B | C | T | |
| 19 | 50169131 | BCL2L12, IRF3 | C | T | rs267605591 |
| 9 | 21971017 | CDKN2A | G | A | rs121913386 |
| 10 | 28284008 | ARMC4 | C | T | |
| 19 | 59010864 | SLC27A5 | G | A | |
| 19 | 20369281 | | G | A | |
| 2 | 198267483 | SF3B1 | C | T | |
| 3 | 96706525 | EPHA6 | C | T | |
| 11 | 118074365 | | G | A | |
| 3 | 77542460 | ROBO2 | C | T | |
| 14 | 21794020 | RPGRIP1 | G | A | |
| 2 | 130930247 | SMPD4 | G | A | |
| 21 | 9825838 | MIR3648-1 | T | TGCG | rs372061766 |
| X | 51239295 | NUDT11 | ATCCTCGAGGCAGCC (SEQ ID NO.: 8) | A | |
| 7 | 140453134 | BRAF | T | C | rs121913364 |
| 11 | 48267238 | OR4X2 | G | A | |
| 17 | 60347259 | TBC1D3P2 | AT | A | |
| 4 | 147560457 | POU4F2 | T | TGGC | |
| 15 | 25601062 | UBE3A, SNHG14 | G | A | |
| 5 | 13769652 | DNAH5 | C | T | |
| 8 | 55539327 | RP1 | G | A | |
| 5 | 13900349 | DNAH5 | C | T | |
| 9 | 137620555 | COL5A1 | G | A | |
| 16 | 21221024 | ZP2 | C | T | rs150656642 |
| 17 | 11835419 | DNAH9 | G | A | |
| 15 | 102293061 | DNM1P47 | TCTC | T | |
| 17 | 26684394 | POLDIP2 | T | TG | rs202089331 |
| 17 | 37213527 | | T | TTTG | rs201590817 |
| 19 | 3118942 | GNA11 | A | T | |
| 14 | 63453898 | KCNH5 | C | T | |
| 8 | 106814408 | ZFPM2 | G | A | |
| 19 | 37677213 | ZNF585B | G | A | rs368332359 |
| 1 | 159683611 | CRP | G | A | |
| 2 | 162751222 | SLC4A10 | C | T | |
| 12 | 53186124 | KRT3 | G | A | |
| 7 | 140453137 | BRAF | C | T | rs121913378 |
| 2 | 209113113 | IDH1 | G | A | rs121913499 |
| 15 | 66729162 | MAP2K1 | C | T | |
| 1 | 18809378 | KLHDC7A | G | A | |
| 19 | 59010865 | SLC27A5 | G | A | |
| 5 | 110710562 | CAMK4 | C | T | rs201866448 |
| 2 | 138414689 | THSD7B | G | A | rs267598902 |
| 1 | 241262011 | RGS7 | G | A | |
| 3 | 189587118 | TP63 | C | T | |
| 7 | 143747706 | OR2A5 | C | T | rs149614119 |

TABLE 5b

Somatic gene mutations associated with SKCM

| Chr | Position | Gene | Wildtype | Mutation | dbsnp |
|---|---|---|---|---|---|
| 7 | 140453136 | BRAF | A | T | rs113488022 |
| 1 | 115256529 | NRAS | T | C | rs11554290 |
| 1 | 115256530 | NRAS | G | T | rs121913254 |
| 1 | 115256529 | NRAS | T | A | rs11554290 |
| 20 | 13029765 | SPTLC3 | G | A | rs267605838 |
| 7 | 6426892 | RAC1 | C | T | |
| 4 | 55594221 | KIT | A | G | rs121913512 |
| 7 | 30795310 | INMT, INMT-FAM188B | C | T | |
| 19 | 50169131 | BCL2L12, IRF3 | C | T | rs267605591 |
| 9 | 21971017 | CDKN2A | G | A | rs121913386 |
| 10 | 28284008 | ARMC4 | C | T | |
| 7 | 140453137 | BRAF | C | T | rs121913378 |
| 2 | 209113113 | IDH1 | G | A | rs121913499 |
| 15 | 66729162 | MAP2K1 | C | T | |
| 1 | 18809378 | KLHDC7A | G | A | |
| 19 | 59010865 | SLC27A5 | G | A | |

TABLE 6a

Somatic gene mutations associated with Stomach Adenocarcinoma (STAD)

| Chr | Position | Gene | Wildtype | Mutation | dbsnp |
|---|---|---|---|---|---|
| 17 | 56435160 | RNF43, BZRAP1-AS1 | AC | A | |
| 17 | 56386384 | BZRAP1 | T | TT | |
| 3 | 178936091 | PIK3CA | G | A | rs104886003 |
| 2 | 54167139 | PSME4 | TG | T | |
| 17 | 7577120 | TP53 | C | T | rs28934576 |
| 17 | 7577094 | TP53 | G | A | |
| 3 | 178921553 | PIK3CA | T | A | rs121913284 |
| 7 | 86542522 | KIAA1324L | TA | T | |
| 17 | 7578406 | TP53 | C | T | rs28934578 |
| 17 | 7577538 | TP53 | C | T | rs11540652 |
| 17 | 7578212 | TP53 | G | A | rs397516436 |
| 17 | 7578403 | TP53 | C | A | |
| X | 79698243 | FAM46D | A | C | |
| 3 | 178952085 | PIK3CA | A | G | rs121913279 |
| 3 | 178936082 | PIK3CA | G | A | rs121913273 |
| 17 | 37868208 | ERBB2 | C | T | |
| 3 | 178560470 | KCNMB2 | T | G | |
| 12 | 25380275 | KRAS | T | G | rs17851045 |
| 16 | 68844172 | CDH1 | G | T | |
| 17 | 7577082 | TP53 | C | T | |
| 12 | 25398284 | KRAS | C | T | rs121913529 |
| 8 | 104898096 | RIMS2 | T | C | |
| 20 | 39832810 | ZHX3 | G | T | rs201454849 |
| 10 | 890938 | LARP4B | GT | G | |
| 19 | 36210763 | KMT2B | AC | A | |
| 3 | 178916876 | PIK3CA | G | A | rs121913287 |
| 1 | 158324361 | CD1E | T | G | |
| 6 | 72678732 | RIMS1 | A | G | |
| 8 | 139164785 | FAM135B | T | G | |
| 12 | 25398285 | KRAS | C | T | rs121913530 |
| 16 | 65016134 | CDH1 | T | G | |
| 19 | 7987518 | SNAPC2 | AC | A | |
| 1 | 158606546 | SPTA1 | T | G | rs370558180 |
| 13 | 29933476 | MTUS2 | C | T | |
| 17 | 48433966 | XYLT2 | AC | A | |
| 9 | 70993145 | PGM5 | A | G | |
| 3 | 114058002 | ZBTB20 | AG | A | |
| 1 | 27105930 | ARID1A | TG | T | |
| 19 | 22002025 | ZNF43 | TA | T | |
| 18 | 34205515 | FHOD3 | AC | A | |
| 18 | 57013284 | LMAN1 | CT | C | |
| 2 | 61577526 | USP34 | TA | T | |
| 2 | 71191572 | ATP6V1B1 | AC | A | |

TABLE 6b

Somatic gene mutations associated with STAD

| Chr | Position | Gene | Wildtype | Mutation | dbsnp |
|---|---|---|---|---|---|
| 17 | 56435160 | RNF43, BZRAP1-AS1 | AC | A | |
| 17 | 56386384 | BZRAP1 | T | TT | |
| 3 | 178936091 | PIK3CA | G | A | rs104886003 |
| 2 | 54167139 | PSME4 | TG | T | |
| 17 | 7577120 | TP53 | C | T | rs28934576 |
| 17 | 7577094 | TP53 | G | A | |
| 3 | 178921553 | PIK3CA | T | A | rs121913284 |
| 7 | 86542522 | KIAA1324L | TA | T | |
| 17 | 7578406 | TP53 | C | T | rs28934578 |
| 17 | 7577538 | TP53 | C | T | rs11540652 |
| 17 | 7578212 | TP53 | G | A | rs397516436 |
| 17 | 7578403 | TP53 | C | A | |
| X | 79698243 | FAM46D | A | C | |
| 3 | 178952085 | PIK3CA | A | G | rs121913279 |
| 3 | 178936082 | PIK3CA | G | A | rs121913273 |
| 17 | 37868208 | ERBB2 | C | T | |
| 12 | 25380275 | KRAS | T | G | rs17851045 |
| 12 | 25398284 | KRAS | C | T | rs121913529 |
| 8 | 104898096 | RIMS2 | T | C | |
| 20 | 39832810 | ZHX3 | G | T | rs201454849 |
| 10 | 890938 | LARP4B | GT | G | |
| 19 | 36210763 | KMT2B | AC | A | |
| 3 | 178916876 | PIK3CA | G | A | rs121913287 |
| 19 | 7987518 | SNAPC2 | AC | A | |
| 1 | 158606546 | SPTA1 | T | G | rs370558180 |
| 13 | 29933476 | MTUS2 | C | T | |
| 17 | 48433966 | XYLT2 | AC | A | |
| 9 | 70993145 | PGM5 | A | G | |
| 3 | 114058002 | ZBTB20 | AG | A | |

TABLE 7a

Somatic gene mutations associated with Bladder Cancer (BLCA)

| Chr | Position | Gene | Wildtype | Mutation | dbsnp |
|---|---|---|---|---|---|
| 10 | 96162370 | TBC1D12 | G | A | |
| 4 | 1803568 | FGFR3 | C | G | rs121913483 |
| 3 | 178936091 | PIK3CA | G | A | rs104886003 |
| 11 | 3427845 | TSSC2 | C | T | |
| 17 | 37868208 | ERBB2 | C | T | |
| 16 | 70065826 | PDXDC2P | T | C | rs3169319 |
| 20 | 33345744 | NCOA6 | C | T | |
| 17 | 7577538 | TP53 | C | T | rs11540652 |
| 3 | 178936082 | PIK3CA | G | A | rs121913273 |
| 10 | 26880266 | LINC00264 | G | A | |
| 7 | 62752443 | ZNF733P | G | C | rs372167638 |
| 14 | 19857036 | | A | G | rs374719458 |
| 1 | 142803543 | ANKRD20A14P | C | T | |
| 9 | 20414343 | MLLT3 | A | G | rs372894655 |
| 1 | 145367739 | NBPF10 | A | G | |
| 22 | 22664141 | BMS1P20 | G | A | rs369590722 |
| 17 | 7577085 | TP53 | C | T | rs112431538 |
| 4 | 1806099 | FGFR3 | A | G | rs121913485 |
| 17 | 39274291 | KRTAP4-11 | T | C | rs200214744 |
| 1 | 16918653 | NBPF1 | C | T | |
| 3 | 12046123 | SYN2 | AAGC | A | rs375843790 |
| 2 | 107049631 | RGPD3 | C | T | |
| 17 | 7577121 | TP53 | G | A | rs121913343 |
| 17 | 62968690 | AMZ2P1 | A | G | |
| X | 44922802 | KDM6A | C | T | |
| 4 | 153247289 | FBXW7 | G | C | |
| 9 | 20414346 | MLLT3 | G | A | |
| 17 | 7577127 | TP53 | C | T | |
| 3 | 178952085 | PIK3CA | A | G | rs121913279 |
| 3 | 197348674 | | A | G | rs376114863 |
| 1 | 142713774 | ANKRD20A12P | A | G | rs201023195 |
| 15 | 102299886 | DNM1P47 | C | CG | rs199996275 |
| 19 | 45867687 | ERCC2 | T | C | |
| 16 | 32070612 | IGHV1OR16-3 | A | C | rs368458790 |
| 21 | 11085863 | BAGE2 | A | AC | |

TABLE 7a-continued

Somatic gene mutations associated with Bladder Cancer (BLCA)

| Chr | Position | Gene | Wildtype | Mutation | dbsnp |
|---|---|---|---|---|---|
| 22 | 18769145 | GGT3P | G | A | rs200209148 |
| 1 | 40713707 | TMCO2 | GTC | G | |
| 2 | 198265453 | SF3B1 | C | T | |
| 10 | 48968566 | GLUD1P2 | A | G | rs201727873 |
| 3 | 195711343 | SDHAP1 | C | CT | rs200252504 |
| 5 | 23527693 | PRDM9 | T | C | |
| 7 | 65222950 | CCT6P1 | CT | C | |
| 8 | 8234868 | SGK223 | C | CGCCGCT | rs150979349 |
| 15 | 102304772 | DNM1P47 | T | C | rs199967915 |
| 9 | 20414340 | MLLT3 | G | A | |
| 9 | 137328351 | RXRA | C | T | |
| 17 | 7577099 | TP53 | C | G | rs121912660 |
| 17 | 45128792 | LRRC37A17P | G | T | |
| 21 | 14414855 | ANKRD30BP2 | A | G | rs201948955 |
| 1 | 142713773 | ANKRD20A12P | C | G | rs199933143 |
| 11 | 3427765 | TSSC2 | G | C | |
| X | 37028425 | FAM47C | A | G | |
| 2 | 107049681 | RGPD3 | T | C | rs369310197 |
| 7 | 17375399 | AHR | G | C | |

TABLE 7b

Somatic gene mutations associated with BLCA

| Chr | Position | Gene | Wildtype | Mutation | dbsnp |
|---|---|---|---|---|---|
| 10 | 96162370 | TBC1D12 | G | A | |
| 4 | 1803568 | FGFR3 | C | G | rs121913483 |
| 3 | 178936091 | PIK3CA | G | A | rs104886003 |
| 11 | 3427845 | TSSC2 | C | T | |
| 17 | 37868208 | ERBB2 | C | T | |
| 16 | 70065826 | PDXDC2P | T | C | rs3169319 |
| 20 | 33345744 | NCOA6 | C | T | |
| 17 | 7577538 | TP53 | C | T | rs11540652 |
| 3 | 178936082 | PIK3CA | G | A | rs121913273 |
| 10 | 26880266 | LINC00264 | G | A | |
| 7 | 62752443 | ZNF733P | G | C | rs372167638 |
| 14 | 19857036 | | A | G | rs374719458 |
| 1 | 142803543 | ANKRD20A14P | C | T | |
| 9 | 20414343 | MLLT3 | A | G | rs372894655 |
| 1 | 145367739 | NBPF10 | A | G | |
| 22 | 22664141 | BMS1P20 | G | A | rs369590722 |
| 17 | 7577085 | TP53 | C | T | rs112431538 |
| 4 | 1806099 | FGFR3 | A | G | rs121913485 |
| 17 | 39274291 | KRTAP4-11 | T | C | rs200214744 |
| 1 | 16918653 | NBPF1 | C | T | |
| 3 | 12046123 | SYN2 | AAGC | A | rs375843790 |
| 2 | 107049631 | RGPD3 | C | T | |
| 17 | 7577121 | TP53 | G | A | rs121913343 |
| 17 | 62968690 | AMZ2P1 | A | G | |
| X | 44922802 | KDM6A | C | T | |
| 4 | 153247289 | FBXW7 | G | C | |
| 9 | 20414346 | MLLT3 | G | A | |
| 17 | 7577127 | TP53 | C | T | |
| 3 | 178952085 | PIK3CA | A | G | rs121913279 |
| 3 | 197348674 | | A | G | rs376114863 |
| 1 | 142713774 | ANKRD20A12P | A | G | rs201023195 |
| 15 | 102299886 | DNM1P47 | C | CG | rs199996275 |
| 19 | 45867687 | ERCC2 | T | C | |
| 9 | 20414340 | MLLT3 | G | A | |
| 9 | 137328351 | RXRA | C | T | |
| 17 | 7577099 | TP53 | C | G | rs121912660 |
| 17 | 45128792 | LRRC37A17P | G | T | |

TABLE 8a

Somatic gene mutations associated with Lung Adenocarcinoma (LUAD)

| Chr | Position | Gene | Wildtype | Mutation | dbsnp |
|---|---|---|---|---|---|
| 12 | 25398285 | KRAS | C | A | rs121913530 |
| 12 | 25398284 | KRAS | C | A | rs121913529 |
| 3 | 10088406 | FANCD2 | TAGTA | T | rs369823368 |
| 12 | 25398284 | KRAS | C | T | rs121913529 |
| 12 | 25398284 | KRAS | C | G | rs121913529 |
| 7 | 140453136 | BRAF | A | T | rs113488022 |
| 21 | 11085863 | BAGE2 | A | AC | |
| 22 | 22664606 | BMS1P20 | A | G | rs187344612 |
| 7 | 140453193 | BRAF | T | C | rs121913370 |
| X | 73506653 | FTX | T | TA | |
| 2 | 175585078 | H3F3AP4 | CA | C | |
| 12 | 25398282 | KRAS | C | A | rs121913535 |
| 21 | 44524456 | U2AF1 | G | A | rs371769427 |
| 1 | 121137802 | | GCCA | G | |
| 22 | 18844763 | BCRP7 | T | C | rs199734135 |
| 7 | 19184711 | FERD3L | G | T | rs202202177 |
| 1 | 238090281 | | G | T | |
| 2 | 65738862 | | TG | T | rs377731020 |
| 7 | 140481402 | BRAF | C | A | rs121913355 |
| 12 | 7080212 | EMG1 | T | TC | rs11428482 |
| 12 | 25398285 | KRAS | C | T | rs121913530 |
| 17 | 60347259 | TBC1D3P2 | AT | A | |
| 5 | 6337065 | | TAC | T | rs371668571 |
| 20 | 26113542 | | TA | T | rs375245697 |
| 7 | 140481411 | BRAF | C | A | rs121913351 |
| 4 | 147560457 | POU4F2 | T | TGGC | |
| 21 | 14414855 | ANKRD30BP2 | A | G | rs201948955 |
| 1 | 16946407 | CROCCP2 | T | G | rs10796418 |
| 20 | 4770300 | RASSF2 | C | A | |
| 16 | 64770704 | | G | GCCAGTGATGGTCACCT (SEQ ID NO.: 9) | rs140029302 |
| 22 | 18842472 | | TG | T | rs66480106 |
| 19 | 54843564 | | T | TC | rs5828583 |
| 10 | 43292056 | BMS1 | G | T | |
| 17 | 7578212 | TP53 | G | A | rs397516436 |
| 2 | 178098944 | NFE2L2 | C | T | |
| 13 | 19420046 | ANKRD20A9P | CTTCGTAT | C | rs377510750 |
| 20 | 33345744 | NCOA6 | C | T | |
| 2 | 131520797 | AMER3 | C | T | rs200882863 |
| 2 | 141232707 | LRP1B | C | A | rs77794732 |
| 2 | 179396364 | TTN,TTN-AS1 | G | A | rs368945564 |
| 4 | 1803568 | FGFR3 | C | G | rs121913483 |
| 5 | 45262556 | HCN1 | C | A | |
| 6 | 29574954 | GABBR1 | G | A | |

TABLE 8b

Somatic gene mutations associated with LUAD

| Chr | Position | Gene | Wildtype | Mutation | dbsnp |
|---|---|---|---|---|---|
| 12 | 25398285 | KRAS | C | A | rs121913530 |
| 12 | 25398284 | KRAS | C | A | rs121913529 |
| 3 | 10088406 | FANCD2 | TAGTA | T | rs369823368 |
| 12 | 25398284 | KRAS | C | T | rs121913529 |
| 12 | 25398284 | KRAS | C | G | rs121913529 |
| 7 | 140453136 | BRAF | A | T | rs113488022 |
| 21 | 11085863 | BAGE2 | A | AC | |
| 22 | 22664606 | BMS1P20 | A | G | rs187344612 |
| 7 | 140453193 | BRAF | T | C | rs121913370 |
| X | 73506653 | FTX | T | TA | |
| 2 | 175585078 | H3F3AP4 | CA | C | |
| 12 | 25398282 | KRAS | C | A | rs121913535 |
| 21 | 44524456 | U2AF1 | G | A | rs371769427 |
| 1 | 121137802 | | GCCA | G | |
| 22 | 18844763 | BCRP7 | T | C | rs199734135 |
| 7 | 19184711 | FERD3L | G | T | rs202202177 |
| 1 | 238090281 | | G | T | |
| 2 | 65738862 | | TG | T | rs377731020 |
| 7 | 140481402 | BRAF | C | A | rs121913355 |
| 12 | 7080212 | EMG1 | T | TC | rs11428482 |
| 12 | 25398285 | KRAS | C | T | rs121913530 |
| 17 | 60347259 | TBC1D3P2 | AT | A | |
| 5 | 6337065 | | TAC | T | rs371668571 |
| 20 | 26113542 | | TA | T | rs375245697 |
| 7 | 140481411 | BRAF | C | A | rs121913351 |
| 4 | 147560457 | POU4F2 | T | TGGC | |
| 20 | 4770300 | RASSF2 | C | A | |
| 22 | 18842472 | | TG | T | rs66480106 |
| 17 | 7578212 | TP53 | G | A | rs397516436 |
| 2 | 178098944 | NFE2L2 | C | T | |
| 13 | 19420046 | ANKRD20A9P | CTTCGTAT | C | rs377510750 |
| 20 | 33345744 | NCOA6 | C | T | |

TABLE 9a

Somatic gene mutations associated with Lung Squamous Cell Carcinoma (LUSC)

| Chr | Position | Gene | Wildtype | Mutation | dbsnp |
|---|---|---|---|---|---|
| 3 | 178936091 | PIK3CA | G | A | rs104886003 |
| 17 | 7578457 | TP53 | C | A | |
| 1 | 243251422 | | CA | C | rs200578702 |
| 2 | 178098810 | NFE2L2 | C | G | |
| 17 | 7577120 | TP53 | C | A | |
| 3 | 21447901 | VENTXP7 | A | ACC | rs112237068 |
| 3 | 178936082 | PIK3CA | G | A | rs121913273 |
| 9 | 21971036 | CDKN2A | C | A | rs121913381 |
| 17 | 7577556 | TP53 | C | A | |
| 17 | 7578407 | TP53 | G | C | rs138729528 |
| 17 | 7579312 | TP53 | C | A | rs55863639 |
| 1 | 145281550 | NOTCH2NL | C | T | |
| 1 | 248616135 | OR2T2 | T | G | |
| 2 | 152410492 | NEB | G | A | rs113068669 |
| 3 | 178952085 | PIK3CA | A | G | rs121913279 |
| 4 | 68930597 | TMPRSS11F, UBA6-AS1 | C | T | rs377605520 |
| 10 | 111630550 | XPNPEP1 | G | A | rs143796899 |
| 17 | 7577547 | TP53 | C | A | |
| 17 | 7577580 | TP53 | T | C | |
| 17 | 7578190 | TP53 | T | C | |
| 19 | 55354367 | KIR2DS4,KIR3DL1 | A | G | rs202149687 |
| 21 | 41385159 | DSCAM | C | T | |
| 8 | 144511953 | MAFA | ATGG | A | rs141816879 |
| 11 | 43283605 | HNRNPKP3 | TA | T | |
| 17 | 7577046 | TP53 | C | A | rs201744589 |
| 17 | 7578442 | TP53 | T | C | rs148924904 |
| 17 | 7578461 | TP53 | C | A | rs121912654 |
| 1 | 78098555 | ZZZ3 | C | T | |
| 1 | 154842199 | KCNN3 | G | GGCTGCT | |
| 1 | 158908901 | PYHIN1 | G | C | |
| 2 | 25965964 | ASXL2 | G | A | |
| 2 | 27849963 | CCDC121,ZNF512 | C | A | |
| 2 | 32855589 | TTC27 | G | T | |
| 2 | 43452225 | ZFP36L2,THADA | C | T | |
| 2 | 131129928 | PTPN18 | AGACGGG | A | rs112040677 |
| 2 | 178098804 | NFE2L2 | C | T | |
| 2 | 178098960 | NFE2L2 | C | G | |
| 3 | 118865717 | C3orf30 | C | A | |
| 4 | 153247289 | FBXW7 | G | C | |
| 5 | 45461983 | HCN1 | G | T | |
| 6 | 32147865 | RNF5 | C | T | |
| 7 | 55259524 | EGFR | T | A | rs121913444 |
| 8 | 139207519 | FAM135B | C | A | |
| 10 | 17432598 | ST8SIA6, ST8SIA6-AS1 | C | A | |
| 10 | 89717708 | PTEN | C | T | |
| 11 | 115080343 | CADM1 | G | T | |
| 12 | 31237922 | DDX11 | G | C | |
| 12 | 46321720 | SCAF11 | G | T | |
| 14 | 19377713 | OR11H12 | C | A | |
| 17 | 7578212 | TP53 | G | A | rs397516436 |
| 2 | 178098944 | NFE2L2 | C | T | |
| 13 | 19420046 | ANKRD20A9P | CTTCGTAT | C | rs377510750 |
| 20 | 33345744 | NCOA6 | C | T | |

TABLE 9b

Somatic gene mutations associated with LUSC

| Chr | Position | Gene | Wildtype | Mutation | dbsnp |
|---|---|---|---|---|---|
| 3 | 178936091 | PIK3CA | G | A | rs104886003 |
| 17 | 7578457 | TP53 | C | A | |
| 1 | 243251422 | | CA | C | rs200578702 |
| 2 | 178098810 | NFE2L2 | C | G | |
| 17 | 7577120 | TP53 | C | A | |
| 3 | 21447901 | VENTXP7 | A | ACC | rs112237068 |
| 3 | 178936082 | PIK3CA | G | A | rs121913273 |
| 9 | 21971036 | CDKN2A | C | A | rs121913381 |
| 17 | 7577556 | TP53 | C | A | |
| 17 | 7578407 | TP53 | G | C | rs138729528 |

TABLE 9b-continued

Somatic gene mutations associated with LUSC

| Chr | Position | Gene | Wildtype | Mutation | dbsnp |
|---|---|---|---|---|---|
| 17 | 7579312 | TP53 | C | A | rs55863639 |
| 1 | 145281550 | NOTCH2NL | C | T | |
| 1 | 248616135 | OR2T2 | T | G | |
| 2 | 152410492 | NEB | G | A | rs113068669 |
| 3 | 178952085 | PIK3CA | A | G | rs121913279 |
| 4 | 68930597 | TMPRSS11F, UBA6-AS1 | C | T | rs377605520 |
| 10 | 111630550 | XPNPEP1 | G | A | rs143796899 |
| 17 | 7577547 | TP53 | C | A | |
| 17 | 7577580 | TP53 | T | C | |
| 17 | 7578190 | TP53 | T | C | |
| 19 | 55354367 | KIR2DS4, KIR3DL1 | A | G | rs202149687 |
| 21 | 41385159 | DSCAM | C | T | |
| 8 | 144511953 | MAFA | ATGG | A | rs141816879 |
| 11 | 43283605 | HNRNPKP3 | TA | T | |
| 17 | 7577046 | TP53 | C | A | rs201744589 |
| 17 | 7578442 | TP53 | T | C | rs148924904 |
| 17 | 7578461 | TP53 | C | A | rs121912654 |
| 17 | 7578212 | TP53 | G | A | rs397516436 |
| 2 | 178098944 | NFE2L2 | C | T | |
| 13 | 19420046 | ANKRD20A9P | CTTCGTAT | C | rs377510750 |
| 20 | 33345744 | NCOA6 | C | T | |

TABLE 10a

Somatic gene mutations associated with Cervical Cancer (CESC)

| Chr | Position | Gene | Wildtype | Mutation | dbsnp |
|---|---|---|---|---|---|
| 3 | 178936091 | PIK3CA | G | A | rs104886003 |
| 3 | 178936082 | PIK3CA | G | A | rs121913273 |
| 22 | 22127164 | MAPK1 | C | T | |
| 12 | 25398284 | KRAS | C | T | rs121913529 |
| 8 | 23292044 | ENTPD4 | GCA | G | rs139348326 |
| 22 | 41565529 | EP300 | G | A | |
| 1 | 16889985 | NBPF1 | T | C | rs6603880 |
| 12 | 56478854 | ERBB3 | G | A | |
| 3 | 183520323 | YEATS2 | G | GTA | rs11276625 |
| 5 | 710914 | ZDHHC11, ZDHHC11B | T | A | rs374638240 |
| 10 | 89692905 | PTEN | G | A | rs121909229 |
| 1 | 103474021 | COL11A1 | G | A | rs377107722 |
| 2 | 220418361 | OBSL1 | C | T | |
| 7 | 149571220 | ATP6V0E2, ATP6V0E2-AS1 | C | T | |
| 17 | 61987643 | CSHL1 | C | T | rs144051040 |
| 22 | 50278464 | ZBED4 | C | T | |
| 17 | 37868208 | ERBB2 | C | T | |
| 1 | 16956993 | CROCCP2 | A | G | |
| 1 | 221875156 | DUSP10 | GA | G | |
| 1 | 43779724 | TIE1 | TTG | T | rs138876276 |
| 1 | 145116147 | SEC22B | T | TA | rs56026824 |
| 1 | 149581234 | | A | AT | |
| 1 | 149858613 | HIST2H2AC | G | C | |
| 1 | 150082513 | VPS45 | CA | C | |
| 1 | 161091814 | DEDD, NIT1 | T | TA | rs397804763 |
| 2 | 153004816 | STAM2 | T | TA | |
| 2 | 174086208 | MLK7-AS1 | G | A | |
| 2 | 178098960 | NFE2L2 | C | G | |
| 2 | 201619757 | AOX2P | TTG | T | |
| 4 | 93225752 | GRID2 | G | GA | |
| 5 | 140263677 | PCDHA13, PCDHA1, PCDHA2, PCDHA3, PCDHA4, PCDHA5, PCDHA6, PCDHA7, PCDHA8, PCDHA9, PCDHA10, PCDHA11, PCDHA12 | G | A | |
| 9 | 131386727 | SPTAN1 | C | T | |
| 14 | 76420881 | TTLL5, IF143 | A | AT | rs368697896 |
| 17 | 43322670 | FMNL1 | G | C | |
| 22 | 23006961 | IGLV2-28 | C | T | rs200228350 |
| X | 64741096 | LAS1L | G | C | |
| 13 | 31205523 | USPL1 | G | A | |
| 1 | 196971786 | CFHR5 | G | A | |
| 3 | 113345005 | SIDT1 | C | T | |
| 3 | 183995182 | ECE2, EIF2B5 | G | A | |
| 5 | 139745485 | SLC4A9 | C | T | |

TABLE 10a-continued

Somatic gene mutations associated with Cervical Cancer (CESC)

| Chr | Position | Gene | Wildtype | Mutation | dbsnp |
|---|---|---|---|---|---|
| 7 | 19184752 | FERD3L | C | T | rs73079402 |
| 8 | 146156819 | ZNF16 | G | A | |
| 14 | 105246551 | AKT1 | C | T | rs121434592 |
| 17 | 39913930 | JUP | G | A | |
| 19 | 1581162 | MBD3 | C | T | |
| 21 | 44524456 | U2AF1 | G | A | rs371769427 |
| 2 | 234294805 | DGKD | CT | C | |
| 3 | 178938934 | PIK3CA | G | A | |
| 9 | 66466650 | | G | C | rs1133399 |
| 9 | 68400475 | | T | G | rs75317582 |
| 18 | 9255426 | ANKRD12 | G | C | |

TABLE 10b

Somatic gene mutations associated with CESC

| Chr | Position | Gene | Wildtype | Mutation | dbsnp |
|---|---|---|---|---|---|
| 3 | 178936091 | PIK3CA | G | A | rs104886003 |
| 3 | 178936082 | PIK3CA | G | A | rs121913273 |
| 22 | 22127164 | MAPK1 | C | T | |
| 12 | 25398284 | KRAS | C | T | rs121913529 |
| 8 | 23292044 | ENTPD4 | GCA | G | rs139348326 |
| 22 | 41565529 | EP300 | G | A | |
| 1 | 16889985 | NBPF1 | T | C | rs6603880 |
| 12 | 56478854 | ERBB3 | G | A | |
| 3 | 183520323 | YEATS2 | G | GTA | rs11276625 |
| 5 | 710914 | ZDHHC11, ZDHHC11B | T | A | rs374638240 |
| 10 | 89692905 | PTEN | G | A | rs121909229 |
| 1 | 103474021 | COL11A1 | G | A | rs377107722 |
| 2 | 220418361 | OBSL1 | C | T | |
| 7 | 149571220 | ATP6V0E2, ATP6V0E2-AS1 | C | T | |
| 17 | 61987643 | CSHL1 | C | T | rs144051040 |
| 22 | 50278464 | ZBED4 | C | T | |
| 17 | 37868208 | ERBB2 | C | T | |
| 1 | 16956993 | CROCCP2 | A | G | |
| 1 | 221875156 | DUSP10 | GA | G | |
| 1 | 43779724 | TIE1 | TTG | T | rs138876276 |
| 1 | 145116147 | SEC22B | T | TA | rs56026824 |
| 1 | 149581234 | | A | AT | |
| 1 | 149858613 | HIST2H2AC | G | C | |
| 1 | 150082513 | VPS45 | CA | C | |
| 1 | 161091814 | DEDD, NIT1 | T | TA | rs397804763 |
| 2 | 153004816 | STAM2 | T | TA | |
| 2 | 174086208 | MLK7-AS1 | G | A | |
| 2 | 178098960 | NFE2L2 | C | G | |
| 2 | 201619757 | AOX2P | TTG | T | |
| 4 | 93225752 | GRID2 | G | GA | |
| 5 | 140263677 | PCDHA13, PCDHA1, PCDHA2, PCDHA3, PCDHA4, PCDHA5, PCDHA6, PCDHA7, PCDHA8, PCDHA9, PCDHA10, PCDHA11, PCDHA12 | G | A | |
| 9 | 131386727 | SPTAN1 | C | T | |
| 14 | 76420881 | TTLL5, IFT43 | A | AT | rs368697896 |
| 17 | 43322670 | FMNL1 | G | C | |
| 22 | 23006961 | IGLV2-28 | C | T | rs200228350 |
| X | 64741096 | LAS1L | G | C | |
| 13 | 31205523 | USPL1 | G | A | |
| 2 | 234294805 | DGKD | CT | C | |
| 3 | 178938934 | PIK3CA | G | A | |
| 9 | 66466650 | | G | C | rsl133399 |
| 9 | 68400475 | | T | G | rs75317582 |
| 18 | 9255426 | ANKRD12 | G | C | |

TABLE 11

Somatic gene mutations associated with Ovarian Cancer (OV)

| Chr | Position | Gene | Wildtype | Mutation | dbsnp |
|---|---|---|---|---|---|
| 17 | 7577538 | TP53 | C | T | rs11540652 |
| 17 | 7578406 | TP53 | C | T | rs28934578 |
| 17 | 7578190 | TP53 | T | C | |
| 17 | 7577121 | TP53 | G | A | rs121913343 |
| 17 | 7577539 | TP53 | G | A | rs121912651 |
| 17 | 7577559 | TP53 | G | A | rs28934573 |
| 17 | 7577124 | TP53 | C | T | |
| 17 | 7578263 | TP53 | G | A | rs397516435 |
| 17 | 7578265 | TP53 | A | G | |
| 1 | 115256529 | NRAS | T | C | rs11554290 |
| 17 | 7577141 | TP53 | C | A | |
| 17 | 7578370 | TP53 | C | A | |
| 17 | 7578394 | TP53 | T | C | |
| 17 | 7578442 | TP53 | T | C | rs148924904 |
| 2 | 106761805 | UXS1 | C | G | |
| 17 | 7578239 | TP53 | C | A | |

TABLE 12a

Somatic gene mutations associated with Breast Cancer (Invasive Ductal Carcinoma)

| Chr | Position | Gene | Wildtype | Mutation | dbsnp |
|---|---|---|---|---|---|
| 3 | 178952085 | PIK3CA | A | G | rs121913279 |
| 3 | 178936091 | PIK3CA | G | A | rs104886003 |
| 3 | 178936082 | PIK3CA | G | A | rs121913273 |
| 3 | 178921553 | PIK3CA | T | A | rs121913284 |
| 9 | 141107536 | FAM157B | G | GGCA | |
| 17 | 7578406 | TP53 | C | T | rs28934578 |
| 10 | 8111432 | GATA3 | TCA | T | |
| 3 | 178952085 | PIK3CA | A | T | rs121913279 |
| 17 | 7577120 | TP53 | C | T | rs28934576 |
| 17 | 7578263 | TP53 | G | A | rs397516435 |
| 17 | 7574003 | TP53 | G | A | |
| 17 | 7578212 | TP53 | G | A | rs397516436 |
| Y | 10037843 | RNA5-8SP6 | C | T | |
| X | 135960146 | RBMX, CEP290 | G | GAA | |
| 10 | 8111513 | GATA3 | T | TG | |
| 17 | 4875737 | CAMTA2 | A | AG | |
| 17 | 7578265 | TP53 | A | G | |
| 10 | 8115874 | GATA3 | C | CG | |
| 1 | 12980232 | PRAMEF7 | G | A | rs201674075 |
| 2 | 9989570 | TAF1B | TA | T | |
| 3 | 178936095 | PIK3CA | A | G | rs397517201 |
| 9 | 116187645 | C9orf43 | GGCA | G | rs371 732185 |
| 15 | 20740458 | GOLGA6L6 | TTCG | T | |
| 17 | 7577557 | TP53 | AG | A | |
| 11 | 1606146 | KRTAP5-1, KRTAP5-AS1 | A | AGCC | |
| 17 | 7578190 | TP53 | T | C | |
| 17 | 7578271 | TP53 | T | C | |
| 16 | 68772218 | CDH1 | C | T | |
| 19 | 11577604 | ELAVL3 | G | GC | |
| 20 | 29614296 | FRG1BP | G | GAGA | rs376619640 |
| 1 | 150917623 | SETDB1 | T | TG | |
| 17 | 7578403 | TP53 | C | A | |
| 17 | 37880220 | ERBB2 | T | C | rs121913470 |
| 1 | 16950261 | CROCCP2 | G | C | rs11260845 |
| 12 | 6702280 | CHD4 | G | A | |
| 12 | 28114897 | PTHLH | CT | C | rs3770 1 4358 |
| 15 | 100340122 | DNM1P46 | GAGA | G | rs368425453 |
| 17 | 7578203 | TP53 | C | T | |
| 17 | 7577539 | TP53 | G | A | rsl 21912651 |
| 3 | 178928079 | PIK3CA | G | A | |
| 1 | 16950687 | CROCCP2 | G | T | rs1762940 |
| 17 | 56056604 | VEZF1 | T | TTGC | |
| 1 | 16946407 | CROCCP2 | T | G | rs10796418 |
| 1 | 45288193 | PTCH2 | A | AG | |
| 1 | 248801953 | OR2T35 | A | AT | |
| 2 | 218712886 | TNS1 | GGCT | G | rs375721540 |

TABLE 12b

Somatic gene mutations associated with Breast Cancer (Invasive Ductal Carcinoma)

| Chr | Position | Gene | Wildtype | Mutation | dbsnp |
|---|---|---|---|---|---|
| 3 | 178952085 | PIK3CA | A | G | rs121913279 |
| 3 | 178936091 | PIK3CA | G | A | rs104886003 |
| 3 | 178936082 | PIK3CA | G | A | rs121913273 |
| 3 | 178921553 | PIK3CA | T | A | rs121913284 |
| 9 | 141107536 | FAM157B | G | GGCA | |
| 17 | 7578406 | TP53 | C | T | rs28934578 |
| 10 | 8111432 | GATA3 | TCA | T | |
| 3 | 178952085 | PIK3CA | A | T | rs121913279 |
| 17 | 7577120 | TP53 | C | T | rs28934576 |
| 17 | 7578263 | TP53 | G | A | rs3975 16435 |
| 17 | 7574003 | TP53 | G | A | |
| 17 | 7578212 | TP53 | G | A | rs397516436 |
| Y | 10037843 | RNA5-8SP6 | C | T | |
| X | 135960146 | RBMX, CEP290 | G | GAA | |
| 10 | 8111513 | GATA3 | T | TG | |
| 17 | 4875737 | CAMTA2 | A | AG | |
| 17 | 7578265 | TP53 | A | G | |
| 10 | 8115874 | GATA3 | C | CG | |
| 1 | 12980232 | PRAMEF7 | G | A | rs201674075 |
| 2 | 9989570 | TAF1B | TA | T | |
| 3 | 178936095 | PIK3CA | A | G | rs397517201 |
| 9 | 116187645 | C9orf43 | GGCA | G | rs371732185 |
| 15 | 20740458 | GOLGA6L6 | TTCG | T | |
| 17 | 7577557 | TP53 | AG | A | |
| 11 | 1606146 | KRTAP5-1, KRTAP5-AS1 | A | AGCC | |
| 17 | 7578190 | TP53 | T | C | |
| 17 | 7578271 | TP53 | T | C | |
| 16 | 68772218 | CDH1 | C | T | |
| 19 | 11577604 | ELAVL3 | G | GC | |
| 20 | 29614296 | FRG1BP | G | GAGA | rs376619640 |
| 1 | 150917623 | SETDB1 | T | TG | |
| 17 | 7578403 | TP53 | C | A | |
| 17 | 37880220 | ERBB2 | T | C | rs121913470 |
| 1 | 16950261 | CROCCP2 | G | C | rs11260845 |
| 12 | 6702280 | CHD4 | G | A | |
| 12 | 28114897 | PTHLH | CT | C | rs377014358 |
| 15 | 100340122 | DNM1P46 | GAGA | G | rs368425453 |
| 17 | 7578203 | TP53 | C | T | |
| 17 | 7577539 | TP53 | G | A | rs121912651 |
| 3 | 178928079 | PIK3CA | G | A | |
| 1 | 16950687 | CROCCP2 | G | T | rs1762940 |
| 17 | 56056604 | VEZF1 | T | TTGC | |

TABLE 13

Somatic gene mutations associated with Leukemia(LAML)

| Chr | Position | Gene | Wildtype | Mutation | dbsnp |
|---|---|---|---|---|---|
| 5 | 170837543 | NPM1 | C | CTCTG | |
| 21 | 44524456 | U2AF1 | G | A | rs371769427 |
| 1 | 115258744 | NRAS | C | T | rs121434596 |
| 1 | 115258747 | NRAS | C | T | rs121913237 |
| 2 | 25463286 | DNMT3A | C | T | rs139293773 |
| 3 | 127396114 | ABTB1 | G | GC | |
| 12 | 25398284 | KRAS | C | T | rs121913529 |
| 1 | 33138072 | RBBP4 | G | A | |
| 21 | 44524456 | U2AF1 | G | T | |

TABLE 14a

Somatic gene mutations associated with Liver Cancer

| Chr | Gene | Mutation | Position | Ref | Alt |
|---|---|---|---|---|---|
| 5 | TERT | c.-124C > T | 1295228 | G | A |
| 1 | RP5-857K21.11 | n.-264T > C | 569492 | T | C |
| 3 | CTNNB1 | c.121A > G | 41266124 | A | G |
| X | AL353698.1-KLF8 | n.562093401 > C | 56209340 | T | C |
| 18 | RP11-1151B14.3 | n.*2949_*2951delAAG | 56119804 | AAAG | A |
| 3 | CTNNB1 | c.1331 > C | 41266136 | T | C |
| 1 | MTND2P28 | n.*3811C > T | 569874 | C | T |
| 3 | CTNNB1 | c.107A > C | 41266110 | A | C |
| 17 | TP53 | c.747G > T | 7577534 | C | A |

TABLE 14a-continued

Somatic gene mutations associated with Liver Cancer

| Chr | Gene | Mutation | Position | Ref | Alt |
|---|---|---|---|---|---|
| 5 | TERT | c.-146C > T | 1295250 | G | A |
| 1 | RP5-857K21.11 | n.-147A > C | 569609 | A | C |
| 17 | KCNJ12 | c.-14135_-14111delGACCAAGGAAGGGCATCCCGACTGT (SEQ ID NO.: 10) | 21304519 | GGACCAAGGAAGGGCATCCGACTGT (SEQ ID NO.: 11) | G |
| 3 | CTNNB1 | c.95A > G | 41266098 | A | G |
| 6 | BEND6-KIAA1586 | n.56898488_56898547delTGTTGTCCTGTTTTTATTTCTCTGTGTTGTTTTTTCTTATTTCTTAGAGGAGCAAAAAG (SEQ ID NO.: 12) | 56898487 | TTGTTGTCCTGTTTTTATTTCTCTGTGTTGTTTTTCTTATTTCTTAGAGGAGCAAAAAG | T |
| 1 | A1M1L | c.-1099T > C | 26671625 | A | G |
| 1 | RP11-417J8.6 | n.-369C > A | 142730336 | G | T |
| 3 | CTNNB1 | c.134C > T | 41266137 | C | T |
| 3 | CTNNB1 | c.1004A > T | 41268766 | A | T |
| 7 | PPP1R3A | c.-182 + 8522_-182 + 8523delAT | 113707157 | CAT | C |
| 1 | RP11-463J7.2-HNRNPA1P46 | n.190881448T > C | 190881448 | T | C |
| 1 | KCNH1 | c.1463-19804_1463-19803delCA | 210997310 | TTG | T |
| 16 | BMS1P8-ENPP7P13 | n.33552402T > C | 33552402 | T | C |
| 3 | CTNNB1 | c.95A > T | 41266098 | A | T |
| 3 | CTNNB1 | c.98C > G | 41266101 | C | G |
| 3 | CTNNB1 | c.101G > T | 41266104 | G | T |
| 3 | CTNNB1 | c.110C > T | 41266113 | C | T |
| 4 | LEF1 | c.1009-1464_1009-1460delTCAAC | 108993385 | GGTTGA | G |
| 9 | AL512625.1 | n.*3948A > G | 66477621 | A | G |
| X | GABRA3 | c.330 + 9198T > A | 151443942 | A | T |
| 1 | KCNN3 | c.1448 + 16056C > T | 154728395 | G | A |
| 11 | CNTN5 | c.577 + 17157_577 + 17162delCTA-TAA | 99733145 | ATATAAC | A |
| 17 | AC006080.1 | n.-2712-2711delTG | 63419488 | TCA | T |
| 2 | THSD7B | c.139 + 1271 > A | 137640014 | T | A |
| 3 | CTNNB1 | c.97T > C | 41266100 | T | C |
| 6 | EXOC2 | c.2682-169C > G | 486933 | G | C |
| 6 | HLA-DRB1-HLA-DQA1 | n.32573345_32573348delTTTG | 32573344 | ATTTG | A |
| 7 | FLNC | c.7780 + 70C > T | 128497460 | C | T |
| 11 | AGBL2 | n.-613C > T | 47732477 | G | A |
| 12 | TDG | c.-53C > T | 104359763 | C | T |
| 15 | EXD1 | c.448-201C > A | 41501986 | G | T |
| 19 | C19orf38 | c.434-63C > A | 10968929 | C | A |
| 3 | PIK3CA | c.3140A > G | 178952085 | A | G |
| 5 | TERT | c.-57A > C | 1295161 | T | G |
| 9 | RP11-96J15.1 | n.-1572A > G | 46757507 | T | C |
| 3 | CTNNB1 | c.133T > C | 41266136 | T | C |
| 1 | MTND2P28 | n.*3815C > G | 569878 | C | G |
| 8 | SAMD12 | c.192 + 45331T > C | 119547623 | A | G |
| 10 | RP11-400G3.3-CYP2C9 | n.96652829G > T | 96652829 | G | T |
| 10 | RP11-400G3.3-CYP2C9 | n.966528271 > C | 96652827 | T | C |
| 4 | RNU6-699P-RP11-584P21.2 | n.68264211C > T | 68264211 | C | T |
| 5 | RPS2P25-CTD-2036A18.2 | n.85091859C > G | 85091859 | C | G |
| 8 | SAMD12 | c.192 + 30453271 > C | 119547623 | A | G |
| 7 | THSD7A | c.4411 + 9260A > G | 11432162 | T | C |
| 17 | APOH | c.*218022182delCAA | 64206068 | TTTG | T |

TABLE 14b

Somatic gene mutations associated with Liver Cancer

| Chr | Gene | Mutation | Position | Ref | Alt |
|---|---|---|---|---|---|
| 5 | TERT | c.-124C > T | 1295228 | G | A |
| 1 | RP5-857K21.11 | n.-2641 > C | 569492 | T | C |
| 3 | CTNNB1 | c.121A > G | 41266124 | A | G |
| X | AL353698.1-KLF8 | n.562093401 > C | 56209340 | T | C |
| 18 | RP11-1151B14.3 | n.*2949_*2951delAAG | 56119804 | AAAG | A |
| 3 | CTNNB1 | c.133T > C | 41266136 | T | C |
| 1 | MTND2P28 | n.*3811C > T | 569874 | C | T |
| 3 | CTNNB1 | c.107A > C | 41266110 | A | C |
| 17 | TP53 | c.747G > T | 7577534 | C | A |
| 5 | TERT | c.-146C > T | 1295250 | G | A |
| 1 | RP5-857K21.11 | n.-147A > C | 569609 | A | C |
| 17 | KCNJ12 | c.-14135_-14111delGACCAAGGAAGGGCATCCCGACTGT (SEQ ID NO.: 10) | 21304519 | GGACCAAGGAAGGGCATCCCGACTGT (SEQ ID NO.: 11) | G |
| 3 | CTNNB1 | c.95A > G | 41266098 | A | G |
| 6 | BEND6-KIAA1586 | n.56898488_56898547delTGTTGTCCTGTTTTTATTTCTCTGTGTTGTTTTTCTTATTTCTTAGAGGAGCAAAAAG (SEQ ID NO.: 12) | 56898487 | TTGTTGTCCTGTTTTTATTTCTCTGTGTTGTTTTTTTCTTATTTCTTAGAGGAGCAAAAAG (SEQ ID NO.: 13) | T |
| 1 | AIM1L | c.-1099T > C | 26671625 | A | G |
| 1 | RP11-417J8.6 | n.-369C > A | 142730336 | G | T |
| 3 | CTNNB1 | c.134C > T | 41266137 | C | T |
| 3 | CTNNB1 | c.1004A > T | 41268766 | A | T |
| 7 | PPP1R3A | c.-182 + 8522_-182 + 8523delAT | 113707157 | CAT | C |
| 1 | RP11-463J7.2-HNRNPA1P46 | n.190881448T > C | 190881448 | T | C |
| 1 | KCNH1 | c.1463-19804_1463-19803delCA | 210997310 | TTG | T |
| 16 | BMS1P8-ENPP7P13 | n.335524021 > C | 33552402 | T | C |
| 3 | CTNNB1 | c.95A > T | 41266098 | A | T |
| 3 | CTNNB1 | c.98C > G | 41266101 | C | G |
| 3 | CTNNB1 | c.101G > T | 41266104 | G | T |
| 3 | CTNNB1 | c.110C > T | 41266113 | C | T |
| 4 | LEF1 | c.1009-1464_1009-1460delTCAAC | 108993385 | GGTTGA | G |
| 9 | AL512625.1 | n.*3948A > G | 66477621 | A | G |
| X | GABRA3 | c.330 + 9198T > A | 151443942 | A | T |
| 3 | CTNNB1 | c.97T > C | 41266100 | T | C |
| 6 | EXOC2 | c.2682-169C > G | 486933 | G | C |
| 6 | HLA-DRB1-HLA-DQA1 | n.32573345_3257334 8delTTTG | 32573344 | ATTTG | A |
| 7 | FLNC | c.7780 + 70C > T | 128497460 | C | T |
| 12 | TDG | c.-53C > T | 104359763 | C | T |
| 15 | EXD1 | c.448-201C > A | 41501986 | G | T |
| 3 | PIK3CA | c.3140A > G | 178952085 | A | G |
| 5 | TERT | c.-57A > C | 1295161 | T | G |
| 9 | RP11-96J15.1 | n.-1572A > G | 46757507 | T | C |
| 3 | CTNNB1 | c.133T > C | 41266136 | T | C |
| 1 | MTND2P28 | n.*3815C > G | 569878 | C | G |
| 8 | SAMD12 | c.192 + 45331T > C | 119547623 | A | G |
| 10 | RP11-400G3.3-CYP2C9 | n.96652829G > T | 96652829 | G | T |
| 10 | RP11-400G3.3-CYP2C9 | n.96652827T > C | 96652827 | T | C |

The bodily fluid for use with the compositions, reaction mixtures and kits provided herein as well as in the methods provided herein can be blood, serum, urine, saliva, sputum, cerebrospinal fluid (CSF), lymph, stool, or ejaculate. In some cases, the bodily fluid is blood. As provided herein, the nucleic acid can be DNA or RNA. In cases wherein the nucleic acid is RNA, the RNA can be converted to cDNA by using reverse transcription prior to pre-amplification. The bodily fluid can be fractionated into a cellular fraction and a non-cellular fraction. The nucleic acid can be extracted from the cellular or non-cellular fraction. Extraction can be performed using any method provided herein. Extraction can be performed using any method known in the art.

The pre-amplification and/or amplification reactions can be performed on the extracted nucleic acid using any nucleic acid amplification techniques and their variations known in the art that amplifies nucleic acid (e.g., DNA) to achieve the objectives specified above. The nucleic acid amplification technique employed in the methods provided herein can be, but is not limited to, polymerase chain reaction (PCR), ligase chain reaction, branched DNA signal amplification, isothermal nucleic acid sequence based amplification (NASBA), other self-sustained sequence replication assays, transcription-based amplification, boomerang DNA amplification, strand-displacement activation, cycling probe technology, and combinations of such amplification methods.

Moreover, the pre-amplification or amplification assays and methods provided herein can be performed qualitatively, whereby the amount of the nucleic acid product produced is at least sufficient for efficient detection of the product, or quantitatively, whereby the amount of the nucleic acid product produced can be measured with reference to a standard useful in determining the significance of the amount of produced nucleic acid (for example, wherein the amount of nucleic acid product is related to a disease state or risk of developing a disease state). An example of qualitative amplification assay for use in the invention herein can be digital PCR. The form of digital PCR employed can be droplet digital PCR (ddPCR). An example of quantitative amplification assay for use in the invention herein can be quantitative PCR (qPCR).

Detection of the one or more amplification products from the amplification reaction can be performed using any technique for detecting nucleic acids known in the art. In some cases, detection of amplification products is performed by utilizing probes in the amplification reaction. In this embodiment, the probes are used in combination with primers during the amplification reaction. The probes can comprise a label as well as sequence specific to one or more target mutations in one or more target genes as provided herein, wherein the label produces a detectable signal only when the target mutation to which the probes is directed is amplified. The label can be any quencher known in the art. The signal can be a colorimetric or fluorescent signal. The signal can be detected by any system known in the art capable of detecting the signal. In some cases, detection of the one or more target mutations is performed by sequencing the amplification products from the pre-amplification reaction as described herein. In some cases, detection of the one or more target mutations is performed by sequencing the amplification products from the amplification reaction following the pre-amplification reaction as described herein. The sequencing can be performed using next-generation sequencing (NGS).

The one or more types of cancer that can be detected by the methods, compositions, kits and reactions provided herein can be any malignant hematological and/or non-hematological malignancy or cancer. Non-limiting examples of cancer that can be detected using the methods provided herein include, but are not limited to, adrenal cortical cancer, anal cancer, bile duct cancer, bladder cancer, bone cancer, brain or a nervous system cancer, breast cancer, cervical cancer, colon cancer, rectal cancer, colorectal cancer, endometrial cancer, esophageal cancer, Ewing family of tumor, eye cancer, gall-bladder cancer, gastrointestinal carcinoid cancer, gastrointestinal stromal cancer, Hodgkin Disease, intestinal cancer, Kaposi Sarcoma, kidney cancer, large intestine cancer, laryngeal cancer, hypopharyngeal cancer, laryngeal and hypopharyngeal cancer, leukemia, hairy cell leukemia (HCL), acute lymphocytic leukemia (ALL), acute myeloid leukemia (AML), chronic lymphocytic leukemia (CLL), chronic myeloid leukemia (CML), chronic myelomonocytic leukemia (CMML), non-HCL lymphoid malignancy (hairy cell variant, splenic marginal zone lymphoma (SMZL), splenic diffuse red pulp small B-cell lymphoma (SDRPSBCL), chronic lymphocytic leukemia (CLL), prolymphocytic leukemia, low grade lymphoma, systemic mastocytosis, or splenic lymphoma/leukemia unclassifiable (SLLU)), liver cancer, lung cancer, non-small cell lung cancer, small cell lung cancer, lung carcinoid tumor, lymphoma, lymphoma of the skin, malignant mesothelioma, multiple myeloma, nasal cavity cancer, paranasal sinus cancer, nasal cavity and paranasal sinus cancer, nasopharyngeal cancer, neuroblastoma, non-Hodgkin lymphoma, oral cavity cancer, oropharyngeal cancer, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma, adult soft tissue sarcoma, skin cancer, basal cell skin cancer, squamous cell skin cancer, basal and squamous cell skin cancer, melanoma, stomach cancer, small intestine cancer, testicular cancer, thymus cancer, thyroid cancer, uterine sarcoma, uterine cancer, vaginal cancer, vulvar cancer, Waldenstrom Macroglobulinemia, and Wilms Tumor.

III. Biomarker Selection

As shown in step 1 of FIG. 1A, a first step in the methods provided herein can entail generation of a target matrix. At a general level, generation of a target matrix can entail selection of one or more biomarkers that can be detected and/or analyzed. The biomarkers selected can have a measurable and statistically significant difference in a disease population (e.g., population of subjects suffering from a type of cancer) compared to a control population. Further, the biomarkers can include small molecules, peptides, proteins, and nucleic acids. The biomarkers can be associated with one or more types of cancers. In a preferred embodiment, the biomarkers for use in the invention are mutations in the nucleic acid of a gene. In this case, selection of gene mutation biomarkers results in the generation of a genomic target matrix as shown in step 1 of FIG. 1A. Biomarker selection for use in the methods provided herein can entail identifying and selecting one or more biomarkers from a database. The database can be a public or subscription-based database comprising empirical datasets for a specific type of cancer. The empirical datasets can comprise all known mutations associated with all known malignancies for a specific type and sub-types of a cancer as derived from subjects suffering from said type or subtypes of said cancer. In some cases, the databases are public databases such as the Cancer Genome Atlas (TCGA) and/or the International Cancer Genome Consortium (ICGC). Identification and selection of said one or more biomarkers can be manually performed by an individual or individuals or can be performed with a computer assisted method. The computer assisted method can employ an algorithm. The algorithm can be publically available or custom designed.

In one embodiment, the biomarkers for use in the invention are nucleic acid, wherein the nucleic acid biomarkers are gene mutations. In this case, generation of a genomic target matrix can entail selecting one or more gene mutations from cancer type/subtype specific datasets retrieved from the TCGA, ICGC databases and/or other such database(s). In some cases, selection of the one or more gene mutations is facilitated in silico. The minimum number of somatic mutations for detecting known malignancies or tumor variations/types across all patients for anyone type of cancer at the percentages provided herein can be 10, 15, 20, 25, 30, 35, 40, 45, 50, 55, 60, 65, 70, 75, 80, 85, 90, 95, or 100. The minimum number of somatic mutations for detecting known malignancies or tumor variations/types across all patients for anyone type of cancer at the percentages provided herein can be from about 10 to about 25, about 10 to about 50, about 10 to about 75, or about 10 to about 100. The minimum number of somatic mutations for detecting known malignancies or tumor variations/types across all patients for anyone type of cancer at the percentages provided herein can be from 10 to 25, 10 to 50, 10 to 75, or 10 to 100.

In some cases, a genomic target matrix containing a minimum number of somatic mutations for detecting more than 50%, 55%, 60%, 65%, 70%, 75%, 80%, 85%, 90%, 95% or 99% of known malignancies associated with more than one type of cancer in bodily fluid is generated. This type of genomic target matrix is generated by combining the genomic target matrices for the more than one type of cancer and removing any overlapping mutations. The set of somatic mutations on a genomic target matrix can represent a minimum number of somatic mutations for detecting about 100% of known malignancies associated with 2, 3, 4, 5, 6, 7, 8, 9, 10, 15, 20, or 25 types of cancer. The minimum number of somatic mutations for detecting known malignancies or tumor variations/types across all patients for 2 or more types of cancer (e.g., any type of cancer provided herein) at the percentages provided herein can be 5, 10, 15, 20, 25, 30, 35, 40, 45, 50, 55, 60, 65, 70, 75, 80, 85, 90, 95, 100, 125, 150, 175, 200, 225, 250, 275, 300, 350, 400, 450, 500, 550, 600, 650, 700, 750 or more. The minimum number of somatic mutations for detecting known malignancies or tumor variations/types across all patients for 2 or more types of cancer (e.g., any type of cancer provided herein) at the percentages provided herein can be from about 10 to about 25, about 10 to about 50, about 10 to about 75, about 10 to about 100, about 10 to about 125, about 10 to about 150, about 10 to about 175, about 10 to about 200, about 10 to about 225, about 10 to about 250, about 10 to about 275, about 10 to about 300, about 10 to about 325, about 10 to about 350, about 10 to about 375, about 10 to about 400, about 10 to about 425, about 10 to about 450, about 10 to about 475, about 10 to about 500, about 10 to about 550, about 10 to about 600, about 10 to about 650, about 10 to about 700 or about 10 to about 750. The minimum number of somatic mutations for detecting known malignancies or tumor variations/types across all patients for 2 or more types of cancer (e.g., any type of cancer provided herein) at the percentages provided herein can be from 10 to 25, 10 to 50, 10 to 75, 10 to 100, 10 to 125, 10 to 150, 10 to 175, 10 to 200, 10 to 225, 10 to 250, 10 to 275, 10 to 300, 10 to 325, 10 to 350, 10 to 375, 10 to 400, 10 to 425, 10 to 450, 10 to 475, 10 to 500, 10 to 550, 10 to 600, 10 to 650, 10 to 700 or 10 to 750. In some cases, provided herein for use in any of the methods provided herein are target gene matrices comprising, consisting essentially of, or consisting of non-duplicative target gene mutations from any combination of Tables 1a-c, 2a-b, 3a-b, 4a-b, 5a-b, 6a-b, 7a-b, 8a-b, 9a-b, 10a-b, 11, 12a-b, 13 and 14a-b. An example of a genomic target matrix covering nucleic acid biomarkers for colorectal and pancreatic cancer is shown in Table 15. A genomic target matrix covering nucleic acid biomarkers for lung adenocarcinoma and squamous cell carcinoma can be a matrix with a combination of a plurality of markers from Tables 8a-b and 9a-b. A genomic target matrix covering nucleic acid biomarkers for bladder, stomach and liver cancer can be a matrix with a combination of a plurality of markers from Tables 6a-b, 7a-b and 14a-b. A genomic target matrix covering nucleic acid biomarkers for melanoma and cutaneous melanoma can be a matrix with a combination of a plurality of markers from Tables 4a-b and 5a-b. A genomic target matrix covering nucleic acid biomarkers for pancreatic and adrenocortical cancer can be a matrix with a combination of a plurality of markers from Tables 2a-b and 3a-b. A genomic target matrix covering nucleic acid biomarkers for breast, cervical and ovarian cancer can be a matrix with a combination of a plurality of markers from Tables 10a-b, 11 and 12a-b. In some cases, a genomic target matrix is a combination of a plurality of markers listed in Tables 1a-c, 2a-b, 3a-b, 4a-b, 5a-b, 6a-b, 7a-b, 8a-b, 9a-b, 10a-b, 11,12a-b, 13 and 14a-b with the removal of any duplicates in order to detect the cancer types for each of said Tables. The plurality of markers can be 5, 10, 15, 20, 25, 30, 35, 40, 45, 50 or more. Thus, in some embodiments, the matrices contain the minimum number of biomarkers required to detect the one or more type of cancer, being detected. One of skill in the art will recognize that any or all of the matrices may be combined in any manner. By way of example only, a combined matrix of breast, cervical and ovarian cancer biomarkers may be constructed by combining the minimum number of biomarkers required from Tables 10a-10b, 11 and 12a-12b, such that the desired sensitivity/specificity is met for detection of those particular cancers.

TABLE 15

Genomic target matrix for colorectal and pancreatic cancer

| Chr | Gene | Mutation | Start | End |
|---|---|---|---|---|
| 3 | HCLS1 | c.1104C > T | 121351315 | 121351315 |
| 5 | PCDHA7 | c.1054C > A | 140215022 | 140215022 |
| 6 | TBP | c.188_189insCAG | 170871012 | 170871012 |
| 6 | TBP | c.216_218delACA | 170871037 | 170871037 |
| 7 | IRF5 | c.572_601del | 128587351 | 128587351 |
| 7 | IRF5 | c.572G > A | 128587374 | 128587374 |
| 9 | PHF2 | c.2962_2963ins | 96439003 | 96439003 |
| 17 | TP53 | c.524G > A | 7578406 | 7578406 |
| 17 | TP53 | c.637C > T | 7578212 | 7578212 |
| 17 | TP53 | c.742C > T | 7577539 | 7577539 |
| 17 | TP53 | c.743G > A | 7577538 | 7577538 |
| 17 | TP53 | c.817C > T | 7577121 | 7577121 |
| 17 | TP53 | c.818G > A | 7577120 | 7577120 |
| 17 | TP53 | c.844C > T | 7577094 | 7577094 |
| 11 | TMPRSS13 | c.248_262del | 117789312 | 117789312 |
| 11 | MAML2 | c.1812_1820del | 95825374 | 95825374 |
| 12 | LRRC43 | c.1552_1553ins | 122685139 | 122685139 |
| 19 | HRC | c.606A > G | 49657889 | 49657889 |
| 17 | SLC5A10 | c.1286_1287ins | 18918509 | 18918509 |
| 22 | NEFH | c.1939_1940ins | 29885566 | 29885566 |
| 22 | NEFH | c.1938A > C | 29885567 | 29885567 |
| 22 | NEFH | c.1965_1988del | 29885580 | 29885580 |
| 22 | NEFH | c.1935A > G | 29885564 | 29885564 |
| 13 | FAM194B | c.413A > G | 46170728 | 46170728 |
| 13 | FAM194B | c.406G > A | 46170735 | 46170735 |
| 13 | FAM194B | c.415T > C | 46170726 | 46170726 |
| 14 | ARHGAP5 | c.1421T > C | 32561296 | 32561296 |
| 15 | MESP2 | c.558G > A | 90320146 | 90320146 |
| 16 | TEKT5 | c.263G > A | 10788468 | 10788468 |
| 17 | KRTAP4-5 | c.245_246ins | 39305774 | 39305774 |
| 17 | ALOX12 | c.123C > G | 6899559 | 6899559 |
| 1 | OPRD1 | c.80G > T | 29138975 | 29138975 |
| 2 | NTSR2 | c.161C > T | 11810095 | 11810095 |
| 8 | ZNF707 | c.525A > G | 144776109 | 144776109 |
| 9 | LURAP1L | c.146_147ins | 12775860 | 12775860 |
| 11 | MUC6 | c.5733G > A | 1017068 | 1017068 |
| 17 | PPM1E | c.99_100ins | 56833456 | 56833456 |
| 19 | ZNF787 | c.1101_1103del | 56599437 | 56599437 |
| 21 | COL18A1 | c.4083_4091del | 46924425 | 46924425 |
| 12 | KRAS | c.35G > A | 25398284 | 25398284 |
| 12 | KRAS | c.35G > T | 25398284 | 25398284 |
| 12 | KRAS | c.34G > C | 25398285 | 25398285 |
| 12 | KRAS | c.183A > C | 25380275 | 25380275 |
| 12 | KRAS | c.183A > T | 25380275 | 25380275 |
| 12 | KRAS | c.34G > T | 25398285 | 25398285 |

TABLE 15-continued

Genomic target matrix for colorectal and pancreatic cancer

| Chr | Gene | Mutation | Start | End |
|---|---|---|---|---|
| 12 | KRAS | c.183A > C | 25380275 | 25380275 |
| 1 | OSBPL9 | c.241 + 5856A > T | 52141040 | 52141040 |
| 20 | GNAS | c.2530C > T | 57484420 | 57484420 |
| 5 | TENM2 | c.3825-22delT | 167638716 | 167638717 |
| 8 | SLC7A2 | c.1315 + 31315 + 4delGA | 17412210 | 17412212 |
| 3 | ATP2C1 | c.6 + 44_6 + 46delGTG | 130613662 | 130613665 |

IV. Sample Collection and Preparation

As shown in step 2 of FIG. 1A, nucleic acid to be analyzed in the invention can be extracted or isolated from a bodily fluid. In some cases, the nucleic acid is extracellular. In some cases, the nucleic acid is present in microvesicles or exosomes. In some cases, the nucleic acid is released from one or more cells circulating within the bodily fluid (e.g., circulating tumor cells). The bodily fluid (also referred to as liquid biological sample) can be blood (including whole blood, leukocytes, peripheral blood mononuclear cells, buffy coat, plasma, and serum), sputum, tears, mucus, nasal washes, nasal aspirate, breath, urine, semen, ejaculate, saliva, meningeal fluid, amniotic fluid, glandular fluid, lymph fluid, nipple aspirate, bronchial aspirate, synovial fluid, joint aspirate, ascites, cells, a cellular extract, and cerebrospinal fluid. In some cases, the bodily fluid is blood.

The blood can be drawn by standard methods into a collection tube. The collection tube can comprising siliconized glass, either without anticoagulant for preparation of serum, or with EDTA, sodium citrate, heparin, or similar anticoagulants, most preferably EDTA, for preparation of plasma. In some cases, the collection tube is configured for stabilizing extracellular or cell-free nucleic acid (e.g., cfDNA). The collection tube can comprise a formaldehyde-free preservative for stabilizing nucleated blood cells. The stabilization of nucleated blood cells can serve to prevent the release of gDNA from the nucleated cells within the blood sample. The collection tube can be a Streck cell-free DNA BCT collection tube.

In some cases, nucleic acid is extracted from blood without fractionation. In a particular embodiment, nucleic acid is extracted from plasma or serum that has been fractionated from whole blood. The use of a non-cellular fraction of blood (i.e., plasma or serum) can serve to reduce the presence of extraneous intracellular DNA being extracted from non-malignant cells which can reduce the sensitivity of the amplification assay or interfere with the amplification assay through release of inhibitors such as porphyrins and hematin. Further, the use of a non-cellular fraction of blood (i.e., plasma or serum) can prevent confounding variables introduced by intracellular DNA derived from circulating cancer cells, for example on interpretation of any quantitative amplification studies performed using the methods provided herein. Plasma or serum may be fractionated from whole blood by centrifugation, preferably gentle centrifugation at 300-800×g for 5-10 minutes, or fractionated by other standard methods. However, high-speed centrifugation can be avoided, as subjecting blood to such treatment may deplete the plasma or serum fraction of extracellular DNA. Since heparin may interfere with PCR, use of heparinized blood may require pretreatment with heparinase. Thus, EDTA is the preferred anticoagulant for blood specimens in which PCR amplification is planned.

Either freshly-collected blood plasma or serum, or frozen (stored) and subsequently thawed plasma or serum can be used in the methods of the invention. Stored plasma or serum should be kept at −20° C. to −70° C., and freshly-collected plasma or serum kept refrigerated or maintained on ice until use.

In some cases, the nucleic acid to be analyzed is cell-free DNA (cfDNA) and the cfDNA is extracted from the bodily fluid. The cfDNA can be extracted using a commercially available kit known in the art. The commercially available kit can be the QIAamp Circulating Nucleic Acid Kit from Qiagen. The cfDNA can be extracted using the gelatin extraction method, the glass bead, silica particle, or diatom extraction method or the acid guanidinium thiocyanate-phenol-chloroform extraction method. The cfDNA can be genomic DNA (gDNA).

In one embodiment, DNA is co-precipitated from plasma or serum with gelatin by a gelatin extraction method modified from that of Fournie et al. (1986, Anal. Biochem. 158: 250-256). A stock 5% (w/v) gelatin solution is prepared by mixing 1 gram gelatin (G8-500, Fisher, Pittsburgh, Pa.) with 20 mLs sterile, double-distilled water, autoclaving for 30 minutes, and filtering through a 0.2 micron filter. The resultant solution is sequentially frozen in a dry ice/ethanol bath and thawed at room temperature for a total of five cycles. A working 0.3% gelatin solution is prepared by heating the stock solution to 60° C. and mixing 600 uL of 5% gelatin with 25 uL of 1 M Tris-HCl (pH 8.0) and 9.4 mLs of sterile, double-distilled water. Plasma or serum (160 uL) is mixed with 12.8 uL of 0.5 M EDTA and 467 uL of sterile, double-distilled water, then emulsified for 3 minutes with 320 uL of phenol or phenol:chloroform:isoamyl alcohol (25:24:1 ratio). The solution is centrifuged at 14,000×g for 10 minutes, and 570 uL of the aqueous layer is removed to a clean tube. DNA is precipitated by addition of 142 uL of the 0.3% gelatin working solution and of 500 uL of cold absolute ethanol, followed by incubation at −20° C. for 1-2 hours. Extracellular DNA may be precipitated within less than 1 h of incubation at −20° C., and a very short incubation may be preferable in some circumstances. Alternatively, longer incubation at −20° C. for 1-2 hours insures the precipitation of most DNA. The sample is centrifuged at 14,000×g at 4-6° C. for 15 minutes, washed once with cold 70% ethanol, and dried in a 60° C. heat block for 10 minutes. DNA is then recovered by the addition of 35 to 70 uL of sterile, double-distilled water preheated to 60° C. Thirty-five uL of the resuspended DNA is used in either step two or step three.

As an alternative rapid method of extracting extracellular DNA or cfDNA from plasma or serum, glass beads, silica particles, or diatoms may be used, as in the method or adaptation of Boom et al. (Boom et al., 1991, J. Clin. Microbial. 29: 1804-1811; Boom et al., 1989, J. Clin. Microbial. 28: 495-503). Size fractionated silica particles are prepared by suspending 60 grams of silicon dioxide (SiO.sub.2, Sigma Chemical Co., St. Louis, Mo.) in 500 mLs of demineralized sterile double-distilled water. The suspension is then settled for 24 hours at room temperature. Four-hundred thirty (430) mLs of supernatant is removed by suction and the particles are resuspended in demineralized, sterile, double-distilled water added to a final volume of 500 mLs. After an additional 5 hours of settlement, 440 mLs of the supernatant is removed by suction, and 600 uL of HCl (32% wt/vol) is added to adjust the suspension to a pH2. The suspension is aliquoted and stored in the dark. Lysis buffer is, prepared by dissolving 120 grams of guanidine thiocyanate (GuSCN, Fluka Chemical, Buchs, Switzerland) into 100 mLs of 0.1 M Tris hydrochloride (Tris-HCl) (pH 6.4), and 22 mLs of 0.2 M EDTA, adjusted to pH 8.0 with NaOH, and 2.6 grams of Triton X-100 (Packard Instrument Co., Downers Grove, Ill.). The solution is then homogenized. Washing buffer is prepared by dissolving 120 grams of guanidine thiocyanate (GuSCN) into 100 mLs of 0.1 M Tris-HCl (pH 6.4). Fifty uL of plasma or serum are mixed with 40 uL of silica suspension prepared as above, and with 900 uL of lysis buffer, prepared as above, using an Eppendorf 5432 mixer over 10 minutes at room temperature. The mixture is then centrifuged at 12,000×g for one minute and the supernatant aspirated and discarded. The silica-DNA pellet is then washed twice with 450 uL of washing buffer, prepared as above. The pellet is then washed twice with one mL of 70% (vol/vol) ethanol. The pellet is then given a final wash with one mL of acetone and dried on a heat block at 56 degrees centigrade for ten minutes. The sample is eluted for ten minutes at 56 degrees centigrade with a TE buffer consisting of 10 mM Tris-HC, one mM EDTA (pH 8.0) with or without Proteinase K (100 ng/ml) as described by Boom et al. Following elution, the sample is then centrifuged at 12,000×g for three minutes, and the DNA-containing supernatant recovered. The DNA extract can now be used in an amplification described herein. (Boom et al., 1991, ibid; Boom et al., 1989, ibid; Cheung et al., 1994, J. Clin. Microbiol. 32: 2593-2597).

As an alternative method, extracellular DNA or cfDNA can be extracted from plasma or serum using variations of the acid guanidinium thiocyanate-phenol-chloroform extraction method. For example, extracellular DNA or cfDNA may be extracted from plasma or serum using TRI reagent, a monophase guanidine-thiocyanate-phenol solution, as described by Chomczynski (1993, Biotechniques 15: 532-534). One mL of plasma or serum is processed using 5-10 mLs of TRI Reagent™ (TRI Reagent, Molecular Research Center, Cincinnati, Ohio, Trisolv™, BioTecx Laboratories, Houston, Tex., TRIzol™, GIBCO BRL/Life Technologies, Gaithersburg, Md., ISOGEN™, Nippon Gene, Toyama, Japan, RNA Stat™ 60, Tel-test, Friendsword, Tex.) according to manufacturer's directions. DNA is precipitated from the interphase with ethanol.

Alternate means of purification which may be used to obtain cfDNA from serum or plasma, including selective retention on a size exclusion column or similar matrix, salting-out method, and other guanidinium thiocyanate extraction methods known in the art.

In some cases, the nucleic acid to be analyzed is present in extracellular vesicles such as microvesicles or exosomes. The nucleic acid can be RNA. In some cases, RNAse inhibitors and RNA stabilizing agents can be added to maintain integrity of the RNA before and during collection. RNAse inhibitors can include proteins, antibodies and chemicals that can inhibit the activity of one or more ribonucleases that may be present in the culture medium or introduced during sample collection and processing. RNAse inhibitor proteins include the mammalian ribonuclease inhibitor protein, which can be isolated in its natural form or produced as a recombinant protein with or without modifications. Antibodies that inhibit RNAse activity have been identified and are commercially available. Chemicals that inhibit RNAse activity include nucleosides, detergents and oxidizing agents. RNA stabilizing agents include commercial products such as RNALater (Qiagen), RNA Stabilizer (Wako) and DNA/RNA Shield (Zymo Research). The extracellular vesicles or exosomes can be isolated through a variety of techniques including differential centrifugation, sucrose gradient centrifugation, microfiltration, antibody-mediated isolation techniques that employ magnetic beads or microfluidic devices to facilitate antibody-ligand binding, washing and vesicle isolation (see Momem-Heravi (12) Biol Chem 10: 1253-62, incorporated by reference herein). In cases in which cells or extracellular vesicles are collected, agents can be added to stabilize the cells or vesicles.

In some cases, the nucleic acid to be analyzed is extracted from a cell circulating in the bodily fluid (e.g., CTC). In these cases, cells can be lysed to release nucleic acid (i.e., DNA and RNA).

In some cases, a solution devoid of nucleases and/or extraneous nucleic acids, that does not stress the cells, and that facilitates handling of a sample, can be used. In some cases, the solution is phosphate-buffered saline containing about 5 mg/ml of molecular biology grade bovine serum albumin. A sample can be washed by transferring the sample to one or more drops of wash solution under oil using a pipette with an inner diameter close to the size of the biopsy sample (e.g., in the 1-5 micron range) and drawing the sample in and out of the pipet several times. Other means of exposing the sample to wash solution can be used.

In some cases, cells can be lysed in a hypotonic solution containing a weak detergent, one or more RNAse inhibitors as mentioned above and a sufficiently large volume to dilute cellular constituents. In some cases, other methods can be used to lyse cells (see e.g., Brown and Audet (2008) Journal of The Royal Society Interface 5: S131-S138, incorporated by reference herein). Methods can include use of a hypotonic solution, one or more detergents (e.g. SDS, NP40, Tween, Triton X-100) at one or more different concentrations, low or high pH (e.g., pH below 6, 5, 4, 3, or 2, or pH above 8, 9, 10, 11, 12, 13), other lysis-inducing chemicals (e.g., chaotropic salts such as guanidinium isothiocyanate), enzymes (e.g., proteinase K), freeze-thaw cycles, heat (e.g., exogenous heat from a conductor, heated solution or laser), mechanical disruption (e.g., contact with sharp object or sonication), electroporation or any combination of the aforementioned approaches.

V. Amplification

Figure 1B:
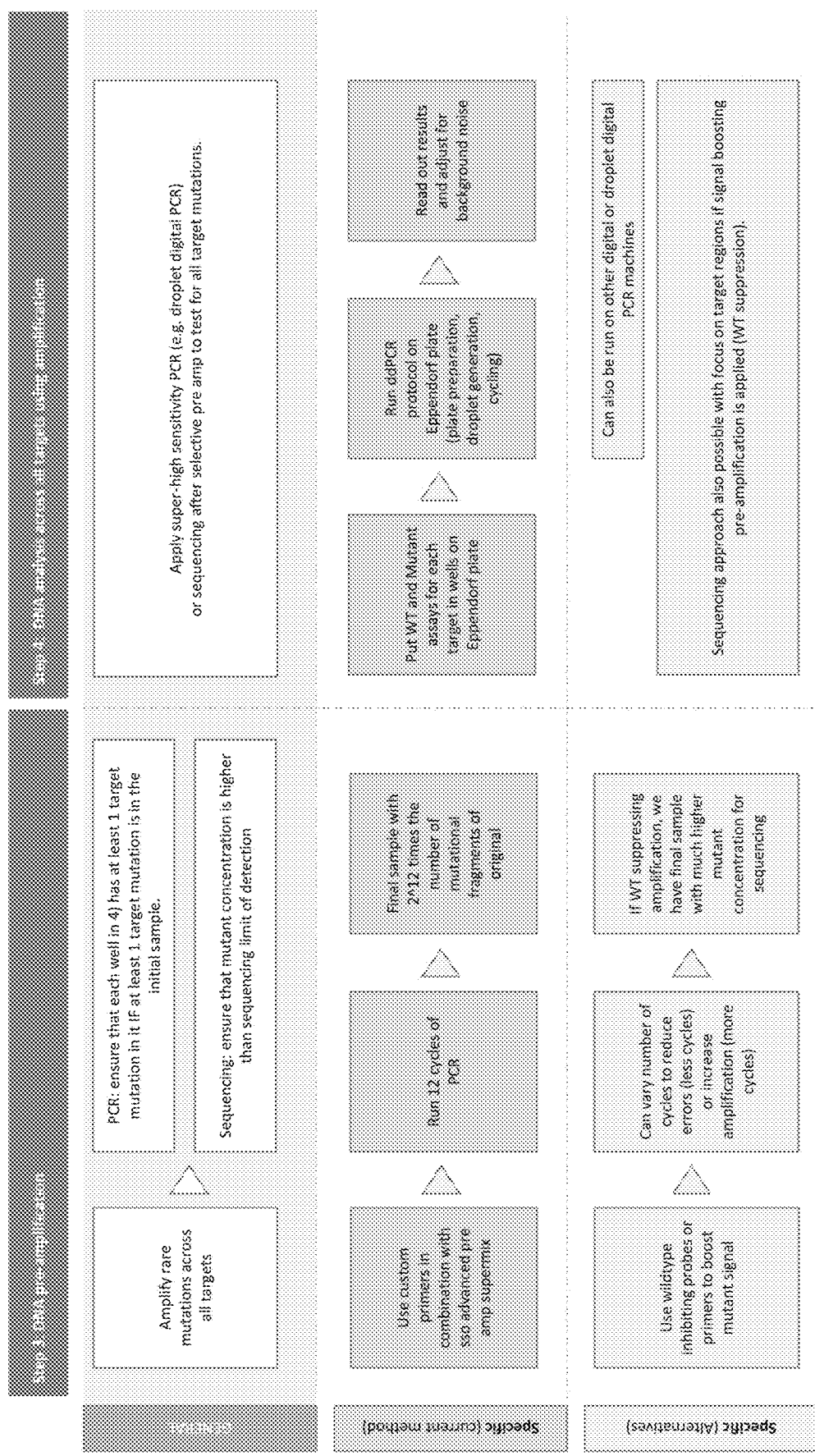

As shown in step 3 of FIG. 1B, following extraction, the nucleic acid to be analyzed in the current invention can be subjected to an amplification reaction. In one embodiment, the amplification reaction shown in step 3 of FIG. 1B is a pre-amplification step that is performed prior to a subsequent amplification step (e.g., step 4 of FIG. 1B). In certain embodiments, the pre-amplification step is performed prior to the subsequent amplification step to enhance the number of target sequences that can be assayed and/or to introduce tags or other additional sequence including a universal primer sight and/or barcode on the products of the pre-amplification step. In some cases, the pre-amplification method can be PCR. For a review of PCR methods, protocols, and principles in designing primers, see, e.g., Innis, et al, PCR Protocols: A Guide to Methods and Applications, Academic Press, Inc. N.Y., 1990.

In some cases, pre-amplification is performed using PCR for a limited number of thermal cycles to provide quantitative amplification of the nucleic acids in the reaction mixture. In certain embodiments, the number of thermal cycles during pre-amplification can be about 3, 4, 5, 6, 7, 8, 9, 10, 11, 12, 13, 14, 15, or more than 15. In some embodiments, reagents useful for the pre-amplification reaction are configured to reduce amplification errors and/or bias. The reagents used in the pre-amplification reaction can be custom buffers and/or enzymes. In some cases, the reagents used for the pre-amplification reaction are commercially available and are designed to reduce and/or eliminate amplification errors and/or bias. Pre-amplification can be alternatively be performed using any applicable amplification assay including ligase chain reaction, branched DNA signal amplification, isothermal nucleic acid sequence based amplification (NASBA), other self-sustained sequence replication assays, transcription-based amplification, Q-beta replication, boomerang DNA amplification, strand-displacement activation, cycling probe technology, and combinations of such amplification methods.

Primers useful in the pre-amplification step described herein can comprise sequence complementary to one or more target genes as listed in Tables 1a-c, 2a-b, 3a-b, 4a-b, 5a-b, 6a-b, 7a-b, 8a-b, 9a-b, 10a-b, 11, 12a-b, 13 and 14a-b. The one or more target genes can contain one or more mutations. The mutations that can be detected by the invention can include single nucleotide variations (SNVs), deletions, or insertions. The one or more mutations can be any mutation shown in Tables 1a-c, 2a-b, 3a-b, 4a-b, 5a-b, 6a-b, 7a-b, 8a-b, 9a-b, 10a-b, 11, 12a-b, 13 and 14a-b. As will be understood by those skilled in the art, primers directed to a target gene such as those provided herein come in pairs, wherein a first primer in the pair comprises sequence complementary to the target gene, while a second primer in the pair comprises sequence complementary to the extension product produced from polymerase mediated extension of the first primer following hybridization of the first primer to the target gene. Primers can be validated empirically to determine amplification efficiency prior to use. In some cases, a set of primers is provided, wherein the set of primers comprises a plurality of primer pairs, wherein each primer pair in the plurality of primer pairs is directed to a target gene described herein. The target gene can be any target gene listed in Tables 1a-c, 2a-b, 3a-b, 4a-b, 5a-b, 6a-b, 7a-b, 8a-b, 9a-b, 10a-b, II, 12a-b, 13 and 14a-b. In one embodiment, the target gene harbors a mutation and each primer in the primer pair comprises sequence complementary to target gene sequence that flanks or does not include the mutation. In this case, detection of the mutation for the target gene is detected by coupling the use of each primer pair in the plurality of primer pairs with a probe that is directed to the mutation as described herein. Thus, in this case a plurality of probes is used in conjunction with the plurality of primer pairs. In this embodiment, the primer pair is designed to amplify a wild-type form of the target gene, while the probe is designed to detect the mutation.

In another embodiment, the target gene harbors a mutation and one or both primers in the primer pair comprise sequence complementary to one or more nucleotides of the mutation in the target gene sequence. In this case, only the mutant form of the target gene will be amplified in the pre-amplification reaction. Subsequent detection of the mutation for the target gene can be accomplished using any of the methods provided herein. In some cases, detection is performed by a subsequent amplification reaction as described herein. In some cases, detection is performed by subsequent sequencing of the pre-amplification products.

As described herein, one or more primers in a primer pair for use in the invention can be used to introduce one or more tags/additional sequences onto one or both ends of the pre-amplification product. The introduction of the tags/additional sequences can be accomplished by using primers comprising tails as described herein. The tails can comprise universal sequence. The universal sequence can be targeted by primers in a subsequent amplification reaction (e.g. Step 4 of FIG. 1B) as described herein.

In some cases, the pre-amplification reaction is used to specifically amplify a form of a target gene harboring a mutation. In some cases, the reaction mixture used for the pre-amplification comprises a primer pair directed against a target gene as described herein as well as a wildtype inhibiting probe. The wildtype inhibiting probe can comprise sequence complementary to the wildtype form of the target gene and can serve to suppress amplification of the wildtype form of the target gene during the pre-amplification reaction. Suppression can be due to the wildtype inhibiting probe possessing a melting temperature much higher than the melting temperatures of the primer pairs used in the pre-amplification reaction. In some cases, the pre-amplification reaction is conducted using a set of primers comprising primer pairs, wherein at least one primer within each primer pair is directed specifically against a mutant form of a target gene as described herein. In this case, the set of primers comprises mutant specific primers.

As shown in Step 4 of FIG. 1B, a preferred embodiment of the invention is conducting an amplification reaction on the products of the pre-amplification reaction produced in Step 3 of FIG. 1B. There are at least two general amplification-based approaches that can be used to following pre-amplification: qualitative amplification and quantitative amplification. In a preferred embodiment, the qualitative amplification is digital amplification. In some cases, the amplification reaction (e.g., quantitative or qualitative) is conducted with the same primer pair or the same set of primers comprising a plurality of primer pairs as was described for the pre-amplification reaction. In some cases, the amplification reaction (e.g., quantitative or qualitative) is conducted with a primer pair or set of primers comprising a plurality of primer pairs wherein each primer in a primer pair comprise the same sequence that is complementary to the target gene as was used in the preceding pre-amplification step. In some cases, the amplification reaction (e.g., quantitative or qualitative) is conducted with a set of primers comprising a plurality of primer pairs wherein each primer in the set of primers comprises sequence complementary to a universal sequence introduced during the pre-amplification step.

Qualitative Amplification

In a preferred embodiment, digital amplification is performed on the products of the pre-amplification reaction(s) described herein. In this case, the products of the pre-amplification reactions serves as a sample, wherein aliquots of the sample can be distributed to separate amplification reactions such that each individual amplification reaction can be expected to include one or fewer amplifiable nucleic acids. In some cases, a set of serial dilutions of the targets can be tested. In some cases, a limiting dilution of the sample can be made across a large number of separate amplification reactions such that most of the reactions can have no template molecules and can give a negative amplification result. In counting the number of positive amplification results, e.g., at the reaction endpoint, the individual template molecules (mutant target gene) present in the original sample can be counted one-by-one. In digital amplification, quantitation can be independent of variations in the amplification efficiency since successful amplifications can be counted as one molecule, independent of the actual amount of product. For discussions of "digital PCR" see, for example, Vogelstein and Kinzler (1999) Proceedings of the National Academy of Sciences of the United States of America 96: 9236-9241; McBride et al., U.S Patent Application Publication No. 20050252773, incorporated herein by reference.

In some cases, identical (or substantially similar) amplification reaction conditions can be run for all of the assays. In other cases, a variety of amplification conditions optimized for each individual reaction can be performed. In a preferred embodiment, each reaction employs the same set of primers, wherein the set of primers comprises primer pairs directed against all the desired mutations in a target matrix as described herein. In some cases, the set of primers is directed against the mutations for a specific type of cancer (e.g., colorectal cancer (Table 1a-1c); pancreatic cancer (Table 2a-2b); adrenocortical cancer (Table 3a-b), melanoma (Table 4a-b), cutaneous melanoma (Table 5a-b), stomach adenocarcinoma (Table 6a-b), bladder cancer (Table 7a-b), lung adenocarcinoma (Table 8a-b), lung squamous cell carcinoma (Table 9a-b), cervical cancer (Table 10a-b), ovarian cancer (Table 11), breast cancer (Table 12a-b), leukemia (Table 13) and liver cancer (Table 14a-b). In another embodiment, each reaction employs the same set of primers, wherein the set of primers comprises primer pairs directed against universal sequences that were appended to the pre-amplification products during the pre-amplification reaction as described herein. Any amplification method can be employed, e.g., PCR, real-time PCR or endpoint PCR. Amplification products can be detected, for example, using a universal probe, such as SYBR Green, or target- and reference-specific probes, which can be included in digital amplification mixtures. In one embodiment, a plurality of target gene specific probes is included in the digital amplification mixtures. In some cases, each target gene specific probe in the plurality comprises sequence complementary to a mutation in the target gene. In this embodiment, the primers used in the pre-amplification reaction were directed to sequence that flanked the mutation in the target gene. The target specific probes can further comprise a quencher and a reporter fluorophores that are designed to fluoresce upon separation of the quencher and reporter during polymerase mediated extension.

A variety of approaches and devices can be used to perform these multiplexed reactions. Digital amplification methods can make use of certain-high-throughput devices suitable for digital PCR, such as microfluidic devices typically containing a large number of small-volume reaction sites (e.g., nano-volume reactions, wells, or chambers). These reaction mixtures can be performed in a reaction/assay platform or microfluidic device or can exist as separate droplets, e.g., as in emulsion PCR. Illustrative Digital Array™ microfluidic devices are described in U.S. application Ser. No. 12/170,414, incorporated herein by reference. Methods for creating droplets having reaction component(s) and/or conducting reactions therein are described in U.S. Pat. No. 7,294,503, U.S. Patent Publication No. 20100022414, U.S. Patent Publication No. 20100092973, incorporated herein by reference. In some cases, a droplet comprising target nucleic acids and a droplet comprising reaction reagents (e.g., nucleotides, polymerase, etc.) can be merged into a single droplet. Any technology that allows for high throughput means to set up, perform and monitor amplification reactions can be used. In a preferred embodiment, droplet digital PCR (ddPCR) is utilized in the methods of the invention.

Quantitative Amplification

Quantitative amplification can be used to determine the amount of template based on the number of cycles of amplification to cross a threshold of detection. In some cases, this type of quantitation can be performed using PCR as the method of amplification. A guideline of steps for experimental design and data analysis for quantitative PCR (qPCR) analyses is outlined by Bustin, et al. ((2009) Clinical Chemistry 55: 611-622, incorporated herein by reference). In some cases, qPCR comprises monitoring the amount of amplification product in real time. In some cases, fluorescence-based technologies can be used, e.g.,(z) probe sequences that fluoresce upon nuclease-catalyzed hydrolysis (TaqMan; Applied Biosystems, Foster City, Calif., USA) or hybridization (LightCycler; Roche, Indianapolis, Ind., USA); fluorescent hairpins; or intercalating dyes (SYBR Green).

Fluorogenic nuclease assays are one example of a real-time quantification method that can be used successfully in the methods described herein. This method of monitoring the formation of amplification product can involve the continuous measurement of PCR product accumulation using a dual-labeled fluorogenic oligonucleotide probe ("TaqMan®") (see e.g., U.S. Pat. No. 5,723,591; Heid et al, 1996, Heid, et al. (1996) Genome Research 6: 986-994, incorporated herein by reference). Other detection/quantification methods that can be employed in this disclosure include (1) FRET and template extension reactions (see e.g., U.S. Pat. No. 5,945,283 and PCT Publication WO 97/22719), (2) molecular beacon detection (see e.g., Piatek et al., 1998, Nat. Biotechnol. 16:359-63; Tyagi and Kramer, 1996, Nat. Biotechnology 14:303-308; and Tyagi, et al, 1998, Nat. Biotechnol. 16:49-53), (3) Scorpion detection (see e.g., Thelwell et al. 2000, Nucleic Acids Research, 28:3752-3761 and Solinas et al., 2001, Nucleic Acids Research 29:20), (4) Invader detection (see e.g., Neri, B. P., et al, 2000, Advances in Nucleic Acid and Protein Analysis 3826: 1 17-125 and U.S. Pat. No. 6,706,471) and (5) padlock probe detection (see e.g., Landegren et al., 2003, Comparative and Functional Genomics 4:525-30; Nilsson et al, 2006, Trends Biotechnol. 24:83-8; Nilsson et al., 1994, Science 265:2085-8), each reference hereby incorporated in its entirety.

In some embodiments, fluorophores can be used as detectable labels for probes including, e.g., rhodamine, cyanine 3 (Cy 3), cyanine 5 (Cy 5), fluorescein, Vic™, Liz™, Tamra™, 5-Fam™, 6-Fam™, and Texas Red (Molecular Probes). Vic™, Liz™, Tamra™, 5-Fam™, 6-Fam™ are all available from Applied Biosystems, Foster City, Calif.

Devices can perform a thermal cycling reaction with compositions that can contain a fluorescent indicator, a source that emits a light beam of a specified wavelength, a detection system that can quantify the fluorescence emitted and a system to display the intensity of fluorescence after each cycle. Devices comprising a thermal cycler, light beam emitter, and a fluorescent signal detector, are described, e.g., in U.S. Pat. Nos. 5,928,907; 6,015,674; and 6, 174,670, incorporated herein by reference.

In some cases, combined thermal cycling and fluorescence detecting devices can be used for precise quantification of target nucleic acids. In some cases, fluorescent signals can be detected and displayed during and/or after one or more thermal cycles, thus permitting monitoring of amplification products as the reactions occur in "real-time." In certain embodiments, one can use the amount of amplification product and number of amplification cycles to calculate how much of the target nucleic acid sequence was in the sample prior to amplification.

According to some cases, the amount of amplification product can be monitored after a predetermined number of cycles sufficient to indicate a presence of the target nucleic acid sequence in a sample. For any given sample type, primer sequence, and reaction condition, how many cycles are sufficient to determine the presence of a given target nucleic acid can be determined. By acquiring fluorescence over different temperatures, the extent of hybridization can be followed. The temperature-dependence of PCR product hybridization can be used for the identification and/or quantification of PCR products. Accordingly, the methods described herein encompass the use of melting curve analysis in detecting and/or quantifying amplicons. Melting curve analysis is well known and is described, for example, in U.S. Pat. Nos. 6,174,670; 6,472,156; and 6,569,627, each of which is hereby incorporated by reference. In illustrative embodiments, melting curve analysis can be carried out using a double-stranded DNA dye, such as SYBR Green, Eva Green, Pico Green (Molecular Probes, Inc., Eugene, Oreg.), ethidium bromide, and the like (see Zhu et al., 1994, Anal. Chem. 66: 1941-48, incorporated herein by reference).

In one embodiment, subjecting nucleic acids extracted from a bodily fluid of subject to a pre-amplification reaction and subsequent amplification reaction as described herein facilitates the detection of one or more mutations of one or more target genes with a specificity of greater than or equal to 55%, 60%, 65%, 70%, 75%, 80%, 85%, 90%, 95%, 99%, or 99.9%. In one embodiment, subjecting nucleic acids extracted from a bodily fluid of subject to a pre-amplification reaction and subsequent amplification reaction as described herein facilitates the detection of one or more mutations of one or more target genes with a sensitivity of greater than or equal to 20%, 25%, 30%, 35%, 40%, 45%, 50%, 55%, 60%, 65%, 70%, 75%, 80%, 85%, 90%, 95%, 99%, or 99.9%. In some cases, subjecting nucleic acids extracted from a bodily fluid of subject to a pre-amplification reaction and subsequent amplification reaction as described herein facilitates the detection of one or more mutations of one or more target genes with a limit of detection (LOD) of about 1, 2, 3, 4, 5, 6, 7, 8, 9, 10, 12, 14, 16, 18, or 20 copies per ml of bodily fluid (e.g., blood). In some cases, subjecting nucleic acids extracted from a bodily fluid of subject to a pre-amplification reaction and subsequent amplification reaction as described herein facilitates the detection of one or more mutations of one or more target genes as provided herein (e.g., Tables 1a-c, 2a-b, 3a-b, 4a-b, 5a-b, 6a-b, 7a-b, 8a-b, 9a-b, 10a-b, 11, 12a-b13 and 14a-b) with a limit of detection (LOD) of about 1 copy in 100, about 1 copy in 500, about 1 copy in 1000, about 1 copy in 2500, about 1 copy in 5000, about 1 copy in 7500, about 1 copy in 10000, about 1 copy in 15,000 or about 1 copy in 20,000 copies of DNA (e.g., ctDNA). In some cases, detection of the one or more mutations of the one or more target genes detects the presence of one or more types of cancer with a specificity of greater than or equal to 55%, 60%, 65%, 70%, 75%, 80%, 85%, 90%, 95%, 99%, or 99.9%. In some cases, detection of the one or more mutations of the one or more target genes detects the presence of one or more types of cancer with a sensitivity of greater than or equal to 20%, 25%, 30%, 35%, 40%, 45%, 50%, 55%, 60%, 65%, 70%, 75%, 80%, 85%, 90%, 95%, 99%, or 99.9%.

VI. Alternate Detection Methods

In one embodiment, detection of the one or more target gene mutations of the one or more targets genes extracted and amplified by the methods provided herein are detected by sequencing the amplification products. Sequencing of the amplification products can occur after the pre-amplification (Step 3 of FIG. 1B) or following a subsequent amplification (Step 4 of FIG. 1B). In one embodiment, the pre-amplification reaction is conducted in the presence of one or more wildtype inhibiting probes as described herein and is followed by a sequencing reaction. The sequencing reaction can be performed using next generation sequencing (NGS). The NGS system used can be any NGS system known in the art.

For example, the methods described herein can be useful for sequencing by the method commercialized by Illumina, as described U.S. Pat. Nos. 5,750,341; 6,306,597; and 5,969,119. Amplified DNA products are prepared using the methods, compositions, kits and reaction mixtures described herein, and can then be denatured and can be randomly attached to the inside surface of flow-cell channels. Unlabeled nucleotides can be added to initiate solid-phase bridge amplification to produce dense clusters of double-stranded DNA. To initiate the first base sequencing cycle, four labeled reversible terminators, primers, and DNA polymerase can be added. After laser excitation, fluorescence from each cluster on the flow cell can be imaged. The identity of the first base for each cluster can then be recorded. Cycles of sequencing are performed to determine the fragment sequence one base at a time.

In some embodiments, the methods described herein are useful for preparing target polynucleotides for sequencing by the sequencing by ligation methods commercialized by Applied Biosystems (e.g., SOLiD sequencing). In other embodiments, the methods are useful for preparing target polynucleotides for sequencing by synthesis using the methods commercialized by 454/Roche Life Sciences, including but not limited to the methods and apparatus described in Margulies et al., *Nature*(2005) 437:376-380 (2005); and U.S. Pat. Nos. 7,244,559; 7,335,762; 7,211,390; 7,244,567; 7,264,929; and 7,323,305. In other embodiments, the methods are useful for preparing target polynucleotide(s) for sequencing by the methods commercialized by Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058. In other embodiments, the methods are useful for preparing target polynucleotide(s) for sequencing by the methods commercialized by Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764.

Another example of a sequencing technique that can be used in the methods described herein is nanopore sequencing (see e.g. Soni G V and Meller A. (2007) *Clin Chem* 53: 1996-2001). A nanopore can be a small hole of the order of 1 nanometer in diameter. Immersion of a nanopore in a conducting fluid and application of a potential across it can result in a slight electrical current due to conduction of ions through the nanopore. The amount of current that flows can be sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore can represent a reading of the DNA sequence.

Another example of a sequencing technique that can be used in the methods described herein is semiconductor sequencing provided by Ion Torrent (e.g., using the Ion Personal Genome Machine (PGM)). Ion Torrent technology can use a semiconductor chip with multiple layers, e.g., a layer with micro-machined wells, an ion-sensitive layer, and an ion sensor layer. Nucleic acids can be introduced into the wells, e.g., a clonal population of single nucleic can be attached to a single bead, and the bead can be introduced into a well. To initiate sequencing of the nucleic acids on the beads, one type of deoxyribonucleotide (e.g., dATP, dCTP, dGTP, or dTTP) can be introduced into the wells. When one or more nucleotides are incorporated by DNA polymerase, protons (hydrogen ions) are released in the well, which can be detected by the ion sensor. The semiconductor chip can then be washed and the process can be repeated with a different deoxyribonucleotide. A plurality of nucleic acids can be sequenced in the wells of a semiconductor chip. The semiconductor chip can comprise chemical-sensitive field effect transistor (chemFET) arrays to sequence DNA (for example, as described in U.S. Patent Application Publication No. 20090026082). Incorporation of one or more triphosphates into a new nucleic acid strand at the 3' end of the sequencing primer can be detected by a change in current by a chemFET. An array can have multiple chemFET sensors.

Another example of a sequencing technique that can be used in the methods described herein is DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 bp. Adapters (Ad1) can be attached to the ends of the fragments. For example, DNA can be fragmented with MspI and size selected to a mean length of about 500 bp. Adapters (Ad1) can be attached to the ends of the fragments. The adapters can be used to hybridize to anchors for sequencing reactions. DNA with adapters bound to each end can be PCR amplified. The adapter sequences can be modified so that complementary single strand ends bind to each other forming circular DNA. The DNA can be methylated to protect it from cleavage by a type IIS restriction enzyme used in a subsequent step. An adapter (e.g., the right adapter) can have a restriction recognition site, and the restriction recognition site can remain non-methylated. The non-methylated restriction recognition site in the adapter can be recognized by a restriction enzyme (e.g., AcuI), and the DNA can be cleaved by AcuI 13 bp to the right of the right adapter to form linear double stranded DNA. A second round of right and left adapters (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Ad1 adapter. A restriction enzyme (e.g., AcuI) can be applied, and the DNA can be cleaved 13 bp to the left of the Ad1 to form a linear DNA fragment. A third round of right and left adapter (Ad3) can be ligated to the right and left flank of the linear DNA, and the resulting fragment can be PCR amplified. The adapters can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adapters (Ad4) can be ligated to the DNA, the DNA can be amplified (e.g., by PCR), and modified so that they bind each other and form the completed circular DNA template. Rolling circle replication (e.g., using Phi 29 DNA polymerase) can be used to amplify small fragments of DNA. The four adapter sequences can contain palindromic sequences that can hybridize and a single strand can fold onto itself to form a DNA nanoball (DNB™) which can be approximately 200-300 nanometers in diameter on average.

A DNA nanoball can be attached (e.g., by adsorption) to a microarray (sequencing flowcell). The flow cell can be a silicon wafer coated with silicon dioxide, titanium and hexamehtyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adapter sequences can be determined.

In some cases, the sequencing technique can comprise paired-end sequencing in which both the forward and reverse template strand can be sequenced. In some cases, the sequencing technique can comprise mate pair library sequencing. In mate pair library sequencing, DNA can be fragments, and 2-5 kb fragments can be end-repaired (e.g., with biotin labeled dNTPs). The DNA fragments can be circularized, and non-circularized DNA can be removed by digestion. Circular DNA can be fragmented and purified (e.g., using the biotin labels). Purified fragments can be end-repaired and ligated to sequencing adapters.

In some cases, a sequence read is about, more than about, less than about, or at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2800, 2900, or 3000 bases. In some cases, a sequence read is about 10 to about 50 bases, about 10 to about 100 bases, about 10 to about 200 bases, about 10 to about 300 bases, about 10 to about 400 bases, about 10 to about 500 bases, about 10 to about 600 bases, about 10 to about 700 bases, about 10 to about 800 bases, about 10 to about 900 bases, about 10 to about 1000 bases, about 10 to about 1500 bases, about 10 to about 2000 bases, about 50 to about 100 bases, about 50 to about 150 bases, about 50 to about 200 bases, about 50 to about 500 bases, about 50 to about 1000 bases, about 100 to about 200 bases, about 100 to about 300 bases, about 100 to about 400 bases, about 100 to about 500 bases, about 100 to about 600 bases, about 100 to about 700 bases, about 100 to about 800 bases, about 100 to about 900 bases, or about 100 to about 1000 bases.

The number of sequence reads from a sample can be about, more than about, less than about, or at least about 100, 1000, 5,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, or 10,000,000.

The depth of sequencing of a sample can be about, more than about, less than about, or at least about 1×, 2×, 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, 46×, 47×, 48×, 49×, 50×, 51×, 52×, 53×, 54×, 55×, 56×, 57×, 58×, 59×, 60×, 61×, 62×, 63×, 64×, 65×, 66×, 67×, 68×, 69×, 70×, 71×, 72×, 73×, 74×, 75×, 76×, 77×, 78×, 79×, 80×, 81×, 82×, 83×, 84×, 85×, 86×, 87×, 88×, 89×, 90×, 91×, 92×, 93×, 94×, 95×, 96×, 97×, 98×, 99×, 100×, 110×, 120×, 130×, 140×, 150×, 160×, 170×, 180×, 190×, 200×, 300×, 400×, 500×, 600×, 700×, 800×, 900×, 1000×, 1500×, 2000×, 2500×, 3000×, 3500×, 4000×, 4500×, 5000×, 5500×, 6000×, 6500×, 7000×, 7500×, 8000×, 8500×, 9000×, 9500×, 10,000×, 15,000×, 20,000×, 25,000×, 30,000×, or 35,000×. The depth of sequencing of a sample can about 1× to about 5×, about 1× to about 10×, about 1× to about 20×, about 5× to about 10×, about 5× to about 20×, about 5× to about 30×, about 10× to about 20×, about 10× to about 25×, about 10× to about 30×, about 10× to about 40×, about 30× to about 100×, about 100× to about 200×, about 100× to about 500×, about 500× to about 1000×, about 1000×, to about 2000×, about 1000× to about 5000×, or about 5000× to about 10,000×. Depth of sequencing can be the number of times a sequence (e.g., a genome) is sequenced. In some cases, the Lander/Waterman equation is used for computing coverage. The general equation can be: C=LN/G, where C=coverage; G=haploid genome length; L=read length; and N=number of reads.

In a separate embodiment, amplified DNA product is detected from step four of FIG. 1B using gel electrophoresis. In this embodiment, the amplified DNA products can be transferred from the gel to a membrane by blotting techniques such as Southern blot analysis and subsequently be detected with a labeled probe directed against the mutant form of the target gene.

An alternative method which may be used to detect the amplified DNA product is ELISA detection. In this embodiment, the primer pairs used in the pre-amplification and/or subsequent amplification reaction are directed against the mutated form of the target gene as described herein. Depending upon the ELISA detection method used, it may be necessary to biotinylate or otherwise modify the primers used in the amplification reaction. For example, one ELISA detection method which may be used is the method described by Landgraf et al. (1991, Anal. Biochem. 198: 86-91) as follows: Primers are modified with biotinylamidocaproate-N-hydroxysuccinimidester (Sigma) and fluorescein isothiocyanate (FITC) (Sigma), by the method of Landgraf et al. (1991, Anal. Biochem. 193: 231-235). Following amplification, the ELISA is carried out in microtiter plates coated with 1 microgram/mL affinity-purified avidin (13 U/mg, Sigma). One uL of the final amplification product (or post-digestion product) is diluted with 50 uL of PBS-Tween, and then incubated at room temperature for 30 minutes in the microtiter plate well. Non-incorporated primers are removed by washing with PBS-Tween. The plates are then incubated at room temperature for 30 minutes after adding 50 uL per well of anti-FITC antibody-HRPO conjugate (Dakopatts) which is at a 1:500 dilution with PBS-Tween. Following this, 80 uL of an ELISA solution made from one milligram 3,3',5,5'tetramethylbenzidine (Sigma) dissolved in one mL dimethyl sulfoxide, and diluted 1:10 with 50 millimol sodium acetate:citric acid, pH 4.9, with 3 uL of 30% (vol/vol) $H_2O_2$ added, is added to each well. After 2-5 minutes, the reaction is stopped by adding 80 uL of 2M $H_2SO_4$. The optical density is then read at 450 nm.

Alternative methods of ELISA detection which may be used include, but are not limited to, immunological detection methods using monoclonal antibody specific for RNA/DNA hybrids, such as by adapting methods described by Coutlee et al. (1989, Anal. Biochem. 181: 96-105), or by Bobo et al. (1990, J. Clin. Microbial. 28: 1968-1973). Additional, alternative methods of ELISA detection which may be used include, but are not limited to, commercial detection systems such as the SHARP signal system (Digene Diagnostics, Inc.), and the DNA enzyme immunoassay (DEIA), (GEN-ETI-K DEIA, Sorin Biomedica).

Alternative methods by which amplified product may be detected include but are not limited to all methods of electrochemiluminescence detection, such as by adapting the method described by Blackburn et al. (1991, Clin. Chem. 37: 1534-1539), or by DiCesare et al. (1993, Biotechniques 15: 152-157), all methods utilizing reverse dot blot detection technology and all methods utilizing high-performance liquid chromatography.

Alternative methods by which amplified product may be detected include the use of microarrays. In this embodiment, probes comprising sequence complementary to at least a portion of the amplification products can be used. The probes can be attached to a solid substrate. The solid substrate can be a bead or a planar surface. The planar surface can be a glass slide. Each of the probes can be directed against any specific target gene mutation described herein. Following capture of the amplification products using the probes attached to a solid substrate as described herein, the amplification products can be detected using any microarray analysis known in the art.

VII. Kits, Compositions and Reaction Mixtures

Also provided herein are kits, compositions, and reaction mixtures for use in the methods provided herein. Any combination of the mutations listed in Tables 1a-c, 2a-b, 3a-b, 4a-b, 5a-b, 6a-b, 7a-b, 8a-b, 9a-b, 10a-b, 11, 12a-b, 13 and 14a-b can be detected using a suitable kit, composition or reaction mixture provided herein, such as for use in performing the methods disclosed herein.

In one aspect, the invention provides kits, compositions or reaction mixtures for the detection of one or more mutations of one or more target genes associated with one or more types of cancer in a bodily fluid obtained from a subject. The one or more mutations or one or more target genes can be any, all, or combinations of those listed in Tables 1a-c, 2a-b, 3a-b, 4a-b, 5a-b, 6a-b, 7a-b, 8a-b, 9a-b, 10a-b, 11, 12a-b, 13 and 14a-b. The one or more types of cancer can be any cancer known in the art and/or provided herein. In some cases, the one or more cancers are colorectal cancer, pancreatic cancer, and/or liver cancer. In some cases, the kits, compositions, or reaction mixtures provided herein detect one or more mutations of one or more target genes associated with 2, 3, 4, 5, 6, 7, 8, 9, 10, 15, or 20 types of cancer.

In one embodiment, a kit, composition or reaction mixture of the invention comprises a first set of primers, wherein the first set of primers comprises a plurality of primer pairs, wherein each primer pair is directed against a target gene. The target gene can be any target gene listed in Tables 1a-c, 2a-b, 3a-b, 4a-b, 5a-b, 6a-b, 7a-b, 8a-b, 9a-b, 10a-b, 11, 12a-b, 13 and 14a-b. In some cases, at least one primer in each primer pair in the first set of primers comprises sequence complementary to a mutation in the one or more target genes such that said primer pair specifically amplifies the mutated form of the one or more target genes. The mutation can be any mutation listed in Tables 1a-c, 2a-b, 3a-b, 4a-b, 5a-b, 6a-b, 7a-b, 8a-b, 9a-b, 10a-b, 11, 12a-b, 13 and 14a-b. In cases where the mutation is a SNV, a first primer in the primer pair can comprise a 3' terminal nucleotide that is complementary to the SNV of the target gene, while a second primer comprises sequence complementary to a separate portion of the target gene. In a separate embodiment, each primer pair in the first set of primers comprises sequence complementary to portions of a target gene (e.g., any gene listed in Tables 1a-c, 2a-b, 3a-b, 4a-b, 5a-b, 6a-b, 7a-b, 8a-b, 9a-b, 10a-b, 11, 12a-b, 13 and 14a-b) that flank a mutation in the target gene. The mutation can be any mutation listed in Tables 1a-c, 2a-b, 3a-b, 4a-b, 5a-b, 6a-b, 7a-b, 8a-b, 9a-b, 10a-b, 11, 12a-b, 13 and 14a-*b*.

In some cases, each primer in the first set of primers further comprises a tail at the primer's 5' end, wherein the 5' tail comprises sequence non-complementary to the target gene. As described herein, the non-complementary sequence in the tail can be a barcode, tag, adaptor sequence, sequencing primer sequence, and/or universal sequence. The adaptor sequence can be adaptor sequence designed to be used in a downstream NGS sequencing reaction (e.g., TruSeq adaptor sequence for use in Illumina based NGS platforms). The universal sequence can be targeted by primers in downstream amplification reactions, whereby any nucleic acid comprising said universal sequences can be amplified.

In one embodiment, in addition to comprising the first set of primers as described herein, a kit, composition, or reaction mixture of the invention further comprises a second set of primers. The second set of primers can comprise a plurality of primer pairs, wherein each primer pair is directed against a target gene. The target gene can be any target gene listed in Tables 1a-c, 2a-b, 3a-b, 4a-b, 5a-b, 6a-b, 7a-b, 8a-b, 9a-b, 10a-b, 11, 12a-b, 13 and 14a-b. In some cases, at least one primer in each primer pair in the second set of primers comprises sequence complementary to a mutation in the one or more target genes such that said primer pair specifically amplifies the mutated form of the one or more target genes. The mutation can be any mutation listed in Tables 1a-c, 2a-b, 3a-b, 4a-b, 5a-b, 6a-b, 7a-b, 8a-b, 9a-b, 10a-b, 11, 12a-b, 13 and 14a-b. In cases where the mutation is a SNV, a first primer in the primer pair can comprise a 3' terminal nucleotide that is complementary to the SNV of the target gene, while a second primer comprises sequence complementary to a separate portion of the target gene. In a separate embodiment, each primer pair in the second set of primers comprises sequence complementary to portions of a target gene (e.g., any gene listed in Tables 1a-c, 2a-b, 3a-b, 4a-b, 5a-b, 6a-b, 7a-b, 8a-b, 9a-b, 10a-b, 11, 12a-b, 13 and 14a-b) that flank a mutation in the target gene. The mutation can be any mutation listed in Tables 1a-c, 2a-b, 3a-b, 4a-b, 5a-b, 6a-b, 7a-b, 8a-b, 9a-b, 10a-b, 11, 12a-b, 13 and 14a-b. In some cases, a kit, composition or reaction mixture provided herein comprises a second set of primers, wherein each primer pair in the second set of primers is identical or the same as a primer pair present in the first set of primers. In some cases, a kit, composition or reaction mixture provided herein comprises a second set of primers, wherein each primer pair in the second set of primers is identical or the same as a primer pair present in the first set of primers, except that each primer pair in the second set of primers further comprises a 5' tail sequence as described herein, wherein the 5' tail sequence comprises adaptor sequence. The adaptor sequence can be adaptor sequence designed to be used in a downstream NGS sequencing reaction (e.g., TruSeq adaptor sequence for use in Illumina based NGS platforms). In some cases, a kit, composition or reaction mixture provided herein comprises a second set of primers, wherein each primer pair in the second set of primers is directed against universal sequence introduced onto the ends of amplification products during a pre-amplification reaction via a first set of primers, wherein each primer pair in the first set comprises 5' tail sequence comprising said universal sequence as described herein.

In one embodiment, in addition to comprising the first set of primers and second set of primers as described herein, a kit, composition, or reaction mixture of the invention further comprises a set of oligonucleotide probes. Each oligonucleotide probe in the set of oligonucleotide probes can comprise sequence complementary to a mutation of a target gene. The target gene and/or mutation can be any mutation listed in Tables 1a-c, 2a-b, 3a-b, 4a-b, 5a-b, 6a-b, 7a-b, 8a-b, 9a-b, 10a-b, 11, 12a-b, 13 and 14a-b. Each oligonucleotide probe in the set of oligonucleotide probes can further comprise a label, which can be detected by any device known in the art configured to detect said label. The label can be any label provided herein. In some cases, each oligonucleotide probe in the set of oligonucleotide probes comprises a reporter and a quencher as described herein such that separation of the reporter and quencher generates a detectable signal. The signal can be detected by any device known in the art configured to detect said signal. Separation of the reporter and the quencher can occur when the oligonucleotide probe comprising said reporter and quencher hybridizes to the target of the oligonucleotide probe and is subsequently displaced during a polymerase catalyzed amplification reaction as described herein. Detection of the detectable signal can serve to indicate the presence of the target (e.g., target gene mutation) of the oligonucleotide probe. In one embodiment, a kit, composition or reaction mixture of the invention further comprises a set of oligonucleotide probes directed against mutations in one or more target genes when the kit, composition or reaction mixture comprises a first set of primers and a second set of primers, wherein both first and second set of primers are identical. In this embodiment, both the first and second set of primers are directed against sequence that flanks a mutation in a target gene as described herein.

The kits, compositions or reaction mixtures can also contain one or more reagents (e.g., solubilization buffers, detergents, washes, enzymes or buffers) for processing a liquid biological sample (e.g., extracting cfDNA or nucleic acid from circulating tumor cells, microvesicles and/or exosomes). Any of the kits, compositions or reaction mixture described herein can also include, e.g., buffers, blocking agents, mass spectrometry matrix materials, antibody capture agents, positive control samples, negative control samples, software and information such as protocols, guidance and reference data. The kits, compositions, or reaction mixtures may include reagents for real-time PCR (e.g., TaqMan probes and/or primers, and enzymes). Additionally, the kits, compositions, or reaction mixtures may include reagents for digital PCR such as ddPCR (e.g., oil, droplet generator, etc.).

Any kit provided herein can further comprise instructions for using the devices and reagents necessary to perform the methods provided herein, handling the sample, and analyzing the data. Further, any kit may be used with a computer system or software to analyze and report the result of the analysis of the liquid biological sample. Additionally, any kit provided herein can further comprise one or more algorithms or computer programs for performing the steps of generating target matrices for one or more type of cancer from datasets obtained from databases as described herein. Alternatively, rather than one or more algorithms or computer programs for generating said target matrices, one or more instructions for manually performing the above steps by a human can be provided. Optionally, any kit provided herein can further comprise one or more software or computer program products for classifying the subject from whom the liquid biological sample was obtained as either having or not having one or more types cancer or for determining the likelihood that the individual has one or more types cancer based on the results of the methods provided herein. Alternatively, rather than one or more computer program products, one or more instructions for manually performing the above steps by a human can be provided.

VIII. Therapeutic Applications

The amplification of tumor-associated or derived DNA using the methods, compositions, reaction mixture or kits provided herein (e.g., DNA derived from circulating tumor cells and/or extracellular DNA from bodily fluid) to detectable levels, can permit additional analysis or other manipulation of that DNA. In some cases, clinical utility is realized from the additional analysis. In this optional step of the invention, amplified DNA can be analyzed to define the characteristics or composition of the tumor from which the DNA originated. Any of several methods can be used, dependent upon the desired information, including nucleic acid sequencing, spectroscopy including proton NMR spectroscopy, biochemical analysis, and immunologic analysis. In some embodiments, amplified DNA is isolated (for example by excising mutant DNA bands from an agarose gel) and sequenced using next-generation sequencing. Prior to sequencing, the amplified DNA can be reamplified, cloned into a plasmid vector, for example the pGEM-T vector plasmid (Promega) or any other vector associated with a specific NGS system (e.g., Illumina). Analysis to define the characteristics or composition of the extracted DNA, and thus the tumor of origin, affords a wide array of clinical utility, including the description, characterization, or classification of the tumor, whether known or occult, such as by tissue of origin, by type (such as premalignant or malignant), phenotype, and genotype, and by description or characterization of tumor behavior, physiology and biochemistry, as to gain understanding of tumor invasiveness, propensity to metastasize, and sensitivity or resistance to various therapies, thereby allowing the prediction of response to either ongoing or planned therapy and, further, allowing evaluation of prognosis. Comparison of the characteristics of the extracted DNA to previous biopsy or surgical specimens can permit further evaluation of tumor heterogeneity or similarity in comparison to that specimen, and thus evaluation of tumor recurrence.

Following extraction of DNA as described herein, complimentary ribonucleic acid (RNA) can be transcribed or manufactured from the DNA. In one embodiment, transcription of RNA is performed by employing a primer with an RNA polymerase promoter region joined to a primer sequence provided herein for the gene mutation of interest in the pre-amplification reaction or amplification reaction. RNA complimentary to the DNA can then be transcribed from the attached promoter region. In another embodiment, amplified DNA is cloned into an expression vector, and RNA complimentary to the DNA is transcribed. Furthermore, as in an optional embodiment, the complimentary RNA can be used in an in vitro translation reaction to manufacture tumor-associated or tumor-specific protein. The tumor-associated or tumor-specific protein can then be detected and/or analyzed.

Extraction of DNA (e.g., extracellular DNA), amplification of tumor-derived or tumor-associated DNA, and characterization, transcription of complimentary RNA, and translation to tumor-associated or tumor-specific protein, can provide significant utility, both in the assignment of therapy and in the development of tumor-specific therapies. Sequencing of amplified DNA or transcription of complementary RNA can allow for assignment or development of antisense compounds, including synthetic oligonucleotides and other antisense constructs appropriately specific to the amplified DNA, such as by construction of an expression plasmid such as by adapting the method of Aoki et al. (1995, Cancer Res. 55: 3810-3816). Similarly, defining tumor characteristics can allow for assignment of specific monoclonal antibody or vaccine therapies appropriately specific to the amplified DNA. Production of corresponding immunologic protein can be used in the development of tumor-specific monoclonal antibodies. Similarly, translated protein can be used in tumor-specific vaccine development. Furthermore, the extracellular DNA can permit a means of defining or allowing the construction of a DNA construct which may be used in vaccine therapy.

The methods provided herein can allow the development and application of tumor-specific therapies even when only premalignant tumors, early cancers, or occult cancers are present. Thus, the methods provided herein can permit the early detection of one or more cancers which can facilitate therapeutic intervention when tumor burden is low, immunologic function is relatively intact, and the patient is not compromised, all increasing the potential for cure.

Additional methods for using the peptide and proteins as antigens for producing antibodies specific for the peptides and proteins encoded by the nucleic acids detected by the methods, compositions, reaction mixtures, and kits described herein are also provided. The isolated extracellular nucleic acids of the invention are also used in methods for producing antisense oligonucleotides, either synthetically or using recombinant genetic methods, and the use thereof for affecting gene expression in a cell will be appreciated by one having ordinary skill in the art in view of the methods for isolating and identifying the target gene mutations provided herein. Vaccine production, as is understood by one with skill in the art, is also enabled using the methods provided herein.

All publications, patents, and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

It should also be noted that there are alternative ways of implementing the present invention. Accordingly, the present embodiments are to be considered as illustrative and not restrictive, and the invention is not to be limited to the details given herein, but may be modified within the scope and equivalents of the appended claims.

EXAMPLES

The present invention is further illustrated by reference to the following Examples. However, it should be noted that these Examples, like the embodiments described above, are illustrative and are not to be construed as restricting the scope of the invention in any way.

Example 1. Use of an Algorithm to Select Tumor Somatic Mutation Datasets for Use in Detecting Somatic Mutations in Peripheral Blood Sample An algorithm was applied to tumor datasets in the Cancer Genome Atlas (TCGA) and the International Cancer Genome Consortium (ICGC) in order to identify mutations for colorectal, pancreatic and liver cancer that were likely to be most relevant for an early detection of cancer approach using a liquid biological sample (e.g., blood).

The algorithm resulted in the detection of overall 144,000 mutations for colorectal cancer. 44 of these mutations were show to cover over 95% of the tumor variations in the databases for colorectal cancer.

Example 2. Validation Study for Detecting Somatic Mutations in Blood

A genomic diagnostics platform was assembled including hardware and chemistry components to enable the parallel analysis of all target previously identified mutations in patient blood samples, whereby the target previously identified mutations will be selected with the algorithm described in the previous example. The genomic diagnostics platform was validated in this example using cfDNA isolated from a blood sample obtained from a healthy individual, wherein the cfDNA samples were spiked with specific mutant or wildtype (wt) nucleic acid sequences. The wt sequences used were TP53 and B-Raf proto-oncogene, serine/threonine kinase (BRAF), while the mutant sequence used was TP53 R175H COSM 10648 (c.524G>A).

To conduct the validation study, DNA was extracted from blood obtained from a healthy individual. More specifically, a 10 ml blood sample from the individual was collected in STRECK cell free DNA BCT tube and separated into plasma and buffy coats using centrifugation at 1500×, 10 min, followed by centrifugation at 12,000× 10 min.

Plasma was then processed using the standard protocol for the circulating free nucleic acid extraction kit by Qiagen.

Elution liquid was evaporated using a 2 hour speed vacuum process at 45 degrees Celsius and the dried, extracted DNA was dissolved in water in preparation for the pre-amplification reaction.

Prior to pre-amplification, the target mutation sequence TP53 R175H COSM 10648 (c.524G>A) was spiked into to the dissolved extracted DNA at a dilution of 10 copies per sample, while the wt sequences for BRAF and TP53 were spiked at a dilution of about 20,000 copies per sample.

The sample containing the TP53 mutant and spiked TP53 and BRAF wt sequences at the concentrations described above was then divided into 5 aliquots and each aliquot was subjected to a separate pre-amplification reaction. Each of the (5) aliquots contained forward primers, reverse primers, and probes (wt & mutant specific probes for BRAF, TP53, KRAS or Adenomatous polyposis coli (APC)) plus SsoAdvanced supermix in a total reaction volume of 25 ul and was subjected to a pre-amplification reaction according to the Bio-Rad Ssoadvanced supermix protocol. In summary, the 5 pre-amplification reactions were (1) TP53 (wt TP53 primers, wt TP53 probe and TP53 R175H COSM 10648 (c.524G>A) mutant specific probe), (2) BRAF (wt BRAF primers, wt BRAF probe and BRAF V600 COSM 476 (c.1799T>A) mutant specific probe), (3) KRAS (wt KRAS primers, wt KRAS probe and KRAS 12D (c.35G>A) mutant specific probe), (4) KRAS (wt KRAS primers, wt KRAS probe and KRAS 13D (c.38G>A) mutant specific probe), and (5) APC (wt APC primers, wt APC probe and APC 1450 mutant specific probe).

Each of the pre-amplification reactions containing the spiked DNA and their specific primer pairs and probes was then amplified using a 13-step cycling protocol as follows:

| BioRad SSoAdvanced Pre Amp PCR protocol custom | | | BIORAD Primers | |
|---|---|---|---|---|
| | Step | Temp in C. | Time | Ramp rate |
| | Polymerase activation and DNA denaturation | 95 | 3 min | — |
| 13 cycles | Denaturation | 95 | 15 sec | — |
| | Annealing | 50 | 1 min | 0.5 c/s |
| | Extension | 58 | 3 min | — |
| | Hold | 4 | forever | — |

Pre-amplification products were subsequently diluted 1:5 to 125 ul.

An Eppendorf plate was prepared to conduct subsequent amplification reactions for each of the (5) pre-amplification reactions. Each of the pre-amplification reactions was split into two wells (i.e., to serve as duplicates) on the Eppendorf plate where each of the two wells received additional amounts of the primer pair used in the pre-amplification reaction as well as a probe directed against the wt sequence of the target gene that the primer pair is directed towards and a probe directed against a specific mutation of the target gene that the primer pair is directed towards as described above. Again, the mutant specific probes used in the amplification reaction were directed against TP53 R175H COSM 10648 (c.524G>A), BRAF V600 COSM 476 (c.1799T>A), KRAS 12D (c.35G>A), KRAS 13D (c.38G>A), or APC 1450 mutations. In summary, the 5 amplification reactions done in duplicate on the Eppendorf plate were (1) TP53, (2) BRAF, (3) KRAS, (4) KRAS, and (5) APC, where reaction (1) had wt TP53 primer pair, wt TP53 probe and TP53 R175H COSM 10648 (c.524G>A) probe, reaction (2) had wt BRAF primer pair, wt BRAF probe and BRAF V600 COSM 476 (c.1799T>A) probe, reaction (3) had wt KRAS primer pair, wt KRAS probe and KRAS 12D (c.35G>A) probe, reaction (4) had wt KRAS primer pair, wt KRAS probe and KRAS 13D (c.38G>A) probe, and reaction (5) had wt APC primer pair, wt APC probe and APC 1450 probe. Each probe contained a reporter and quencher to allow for detection of amplification products.

In each well, 2 ul of pre-amplification product, 12.5 ul of BioRad noUTP ddPCR supermix and 8.5 ul of PCR grade water was added.

The wells were then processed following the BioRad QX200 ddPCR protocol, including droplet generation, 40 cycle amplification as shown in Table 16 and droplet readout.

TABLE 16

Thermal Cycling Protocol* Use a heated lid set to 105° C. and set the sample volume to 40 µl.

| Cycling Step | Temperature | Time | Ramp Rate | # Cycles |
|---|---|---|---|---|
| Enzyme activation | 95° C. | 10 min | ~2° C./sec | 1 |
| Denaturation | 94° C. | 30 sec | | 40 |
| Annealing/extension | 55° C. | 1 min | | |
| Enzyme deactivation | 98° C. | 10 min | | 1 |
| Hold (optional) | 4° C. | infinite | ~1° C./sec | 1 |

Figure 2A:
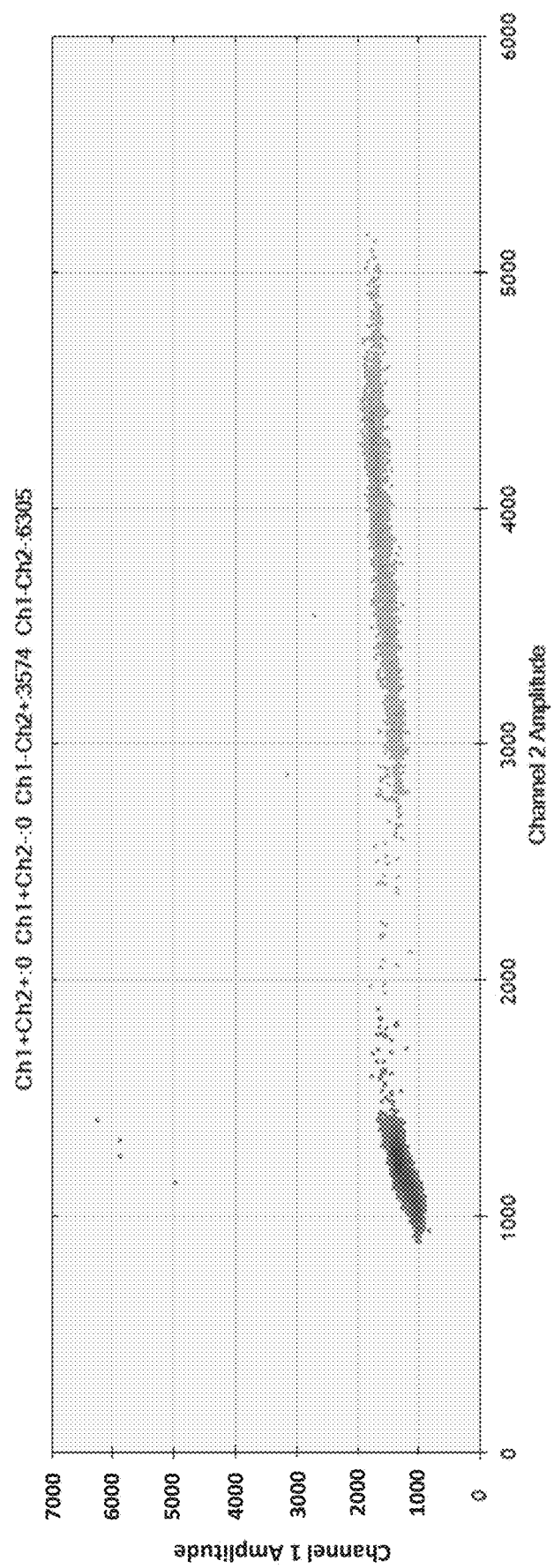
FIG. 2A-E illustrates results from validation studies conducted using methods described herein to detect a target mutation in a background of wildtype nucleic acid.
Figure 2B:
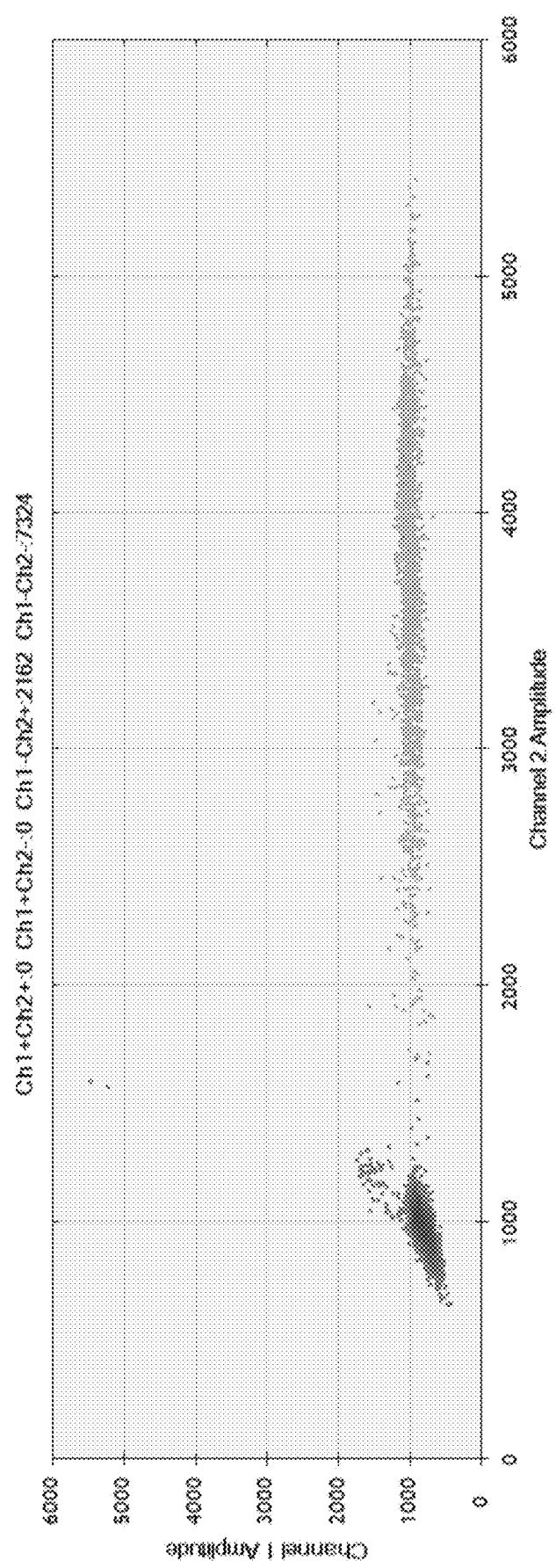
Figure 2C:
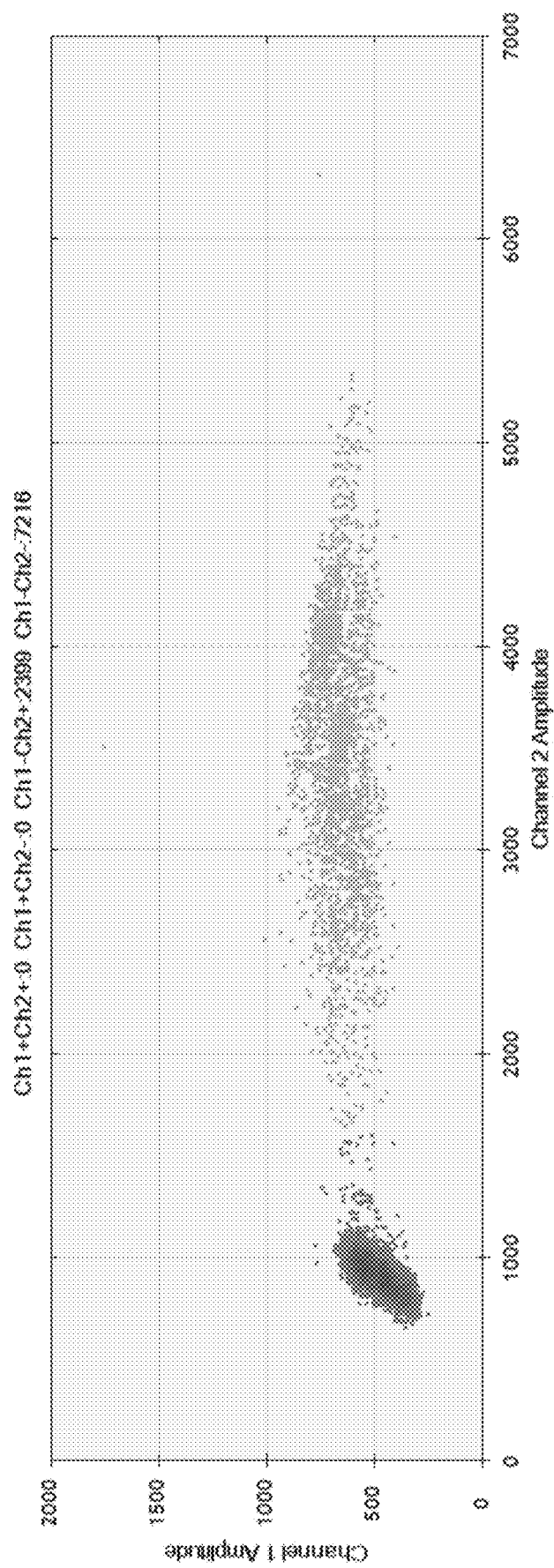
Figure 2D:
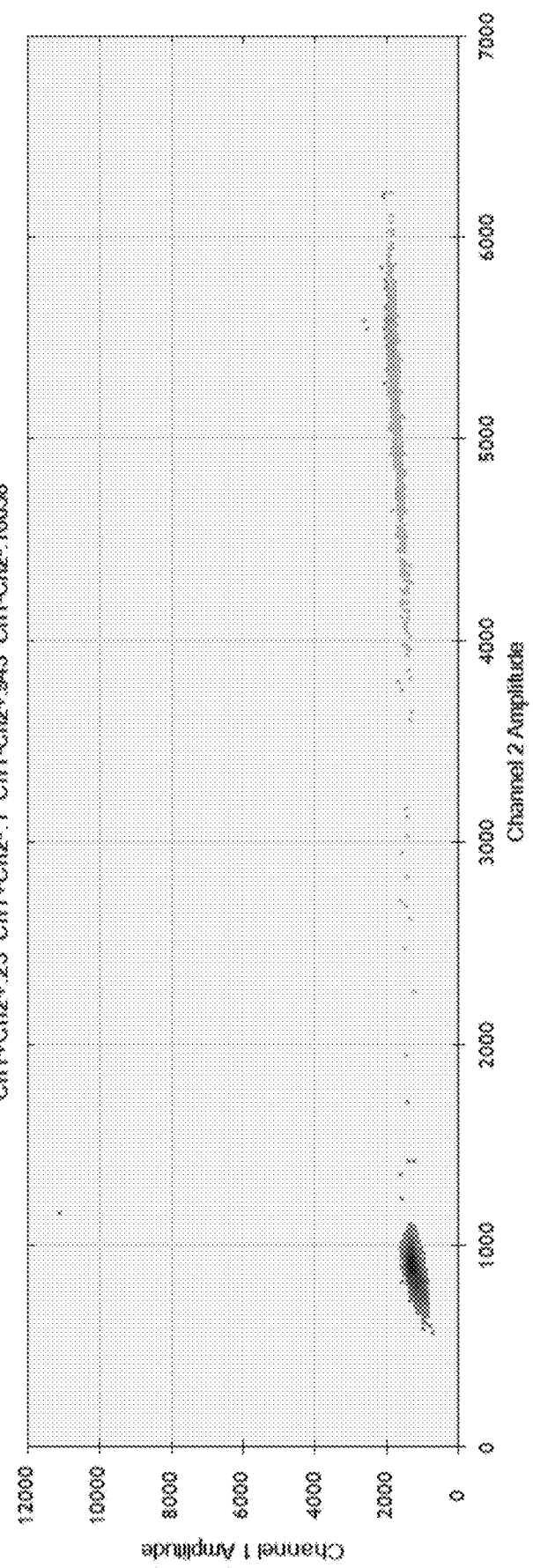
Figure 2E:
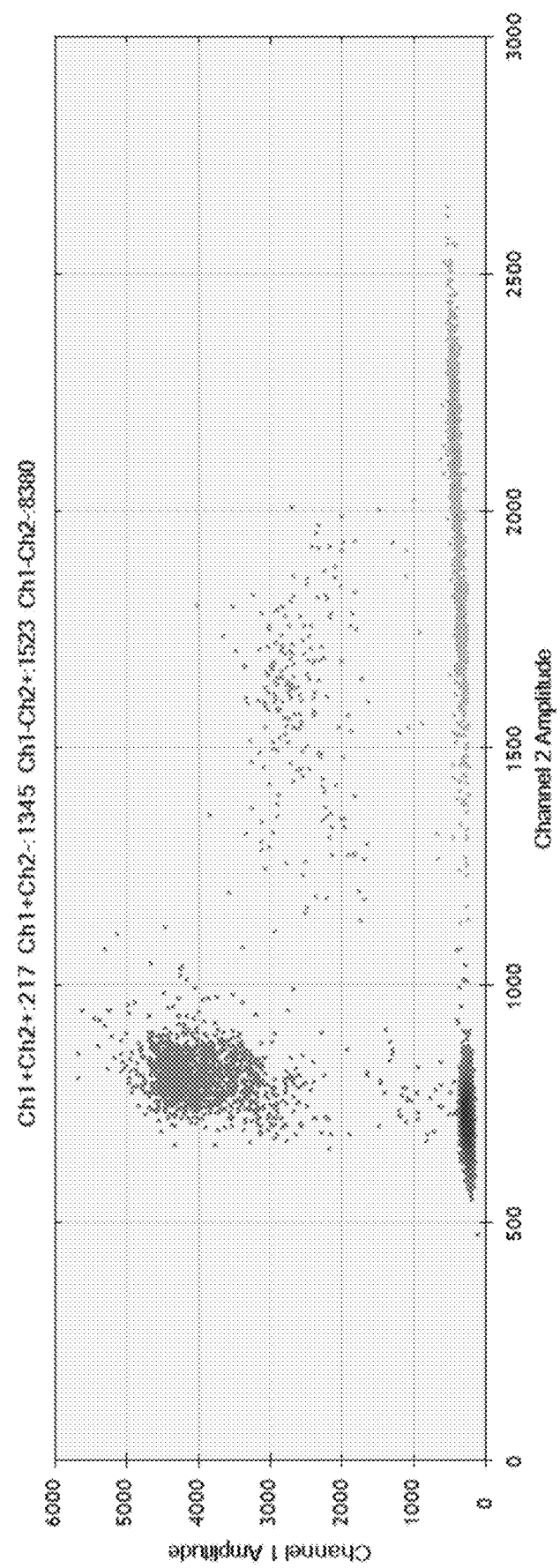

The results were analyzed using Quantasoft software in a 2D plot and are shown in FIGS. 2A-E. The vertical axis shows the intensity of the frequency emitted that is correlated with mutant targets. The horizontal axis shows the intensity of the frequency emitted that is correlated with wildtype targets. Each dot represents one droplet. Between the duplexed wells, no significant differences were observed. For simplification, only one well per target sequence is shown. FIGS. 2A, 2B, 2C and 2D were spiked with BRAF and TP53 wildtype sequences and amplification and detection of specific mutations for BRAF V600E (FIG. 2A), KRAS 12D (FIG. 2B), KRAS 13D (FIG. 2C) or APC 1450 (FIG. 2D) did not show any mutants present, while FIG. 2E showed the presence of the spiked TP53 mutant at a limit of detection of 10 copies per sample. As such, analysis of spiked probes resulted in the validation of the process at a limit of detection of ten copies of mutant DNA at 100% specificity.

Example 3. Circulating Tumor DNA Exposure in Peripheral Blood

Peripheral blood specimens are collected and data are collected and entered from a total of up to 200 subjects. The data to be collected and entered includes: demographics (age, gender, disease, disease specific risk factor, cancer screening status, mode of diagnosis), tumor characteristics (tumor stage, tumor markers), treatment (type of treatment, intent of treatment), specimen assessment (detection of ctDNA, tissue sample DNA analysis (if possible after surgical removal and pathological assessment)), postoperative assessment (if applicable, postoperative staging will be recorded).

Technology and Process Description ctDNA is detected in peripheral blood using:

1.) A blood collection and plasma isolation protocol that ensures higher plasma purity and less contamination by intracellular DNA compared to collection in conventional EDTA tubes and one-step plasma separation by centrifuging.

2.) A DNA extraction process based on the Qiagen circulating nucleic acid extraction kit (Qiagen, Limburg, Germany) with changes to incubation times, buffer volumes and other variables that increases the circulating free DNA yield from samples compared to the Qiagen standard protocol.

3.) A primer-based diagnostics array platform using components from Bio-Rad Laboratories, Inc. (Hercules, Calif., USA) and Integrated DNA Technologies (Coralville, Iowa, USA) that allows for the detection of a wide range of somatic cancer mutations with a much higher sensitivity than current sequencing, PCR and qPCR approaches.

4.) A data processing logic that identifies cancer and mutation classes based on the data generated by the primer-based diagnostics platform.

Specifically, 20 ml of peripheral venous of blood is sampled using STRECK cell free DNA tubes (STRECK, Omaha, Nebr., USA) and labeled with a study identifier. In addition, a case report form with the same study identifier is filled for each patient. The blood collection tubes are shipped within 48 hours of collection to University of Berkeley core facility in Berkeley, Calif., USA for plasma isolation and DNA extraction. In the laboratory, plasma is isolated from each blood sample using the above described plasma isolation protocol. The separated plasma is further processed at Berkeley core facility to extract the cfDNA. The extracted DNA is then transported to a laboratory at Berkeley University Barker Hall where the array platform is applied to the extracted DNA samples. The final data analytics and interpretation using the data processing logic.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for detecting a gene mutation in three or more target genes in a subject, the method comprising: (a) pre-amplifying DNA extracted from a liquid biological sample obtained from the subject using a pre-amplification reaction with a first set of primers directed against the gene mutations mucin 4, cell surface associated (MUC4) T>A rs75263205 found on chromosome 3 at position 195518112, B-Raf proto-oncogene, serine/threonine kinase (BRAF) A>T rs113488022 found on chromosome 7 at position 140453136 and tumor protein p53 (TP53) C>T rs28934578 found on chromosome 17 at position 7578406 alone or in combination with at least one additional gene mutation in a target gene, wherein the at least one additional gene mutation is selected from Transmembrane Protease, Serine 13 (TMPRSS13) CGGGCTGGAGATGCCT (SEQ ID NO: 1)>C rs201746372 found on chromosome 11 starting at position 117789312, TATA Box Binding Protein (TBP) A>ACAG rs201732168 found on chromosome 6 starting at position 170871013, Kirsten rat sarcoma viral oncogene homolog (KRAS) C>T rs121913529 found on chromosome 12 at position 25398284, KRAS C>T rs112445441 found on chromosome 12 at position 25398281, Interferon Regulatory Factor 5 (IRF5) G>A rs113806178 found on chromosome 7 at position 128587374, TP53 C>T rs11540652 found on chromosome 17 at position 7577538, KRAS C>A rs121913529 found on chromosome 12 at position 25398284, glutamate rich 6B (ERICH6B) T>C rs45625342 found on chromosome 13 at position 46170728, Neurofilament, Heavy Polypeptide (NEFH) A>C rs75808076 found on chromosome 22 at position 29885567, APC, WNT signaling pathway regulator (APC) C>T rs121913332 found on chromosome 5 at position 112175639, Mastermind-Like Transcriptional Coactivator 2 (MAML2) TTGCTGCTGC (SEQ ID NO: 2) >T rs141671766 found on chromosome 11 starting at position 95825374, phosphatidylinositol-4,5-bisphosphate 3-kinase catalytic subunit alpha (PIK3CA) G>A rs104886003 found on chromosome 3 at position 178936091, APC C>T found on chromosome 5 at position 112116592, ring finger protein 43, TSPO associated protein 1 (RNF43, BZRAP1-AS1) AC>A found on chromosome 17 starting at position 56435160, tetrapeptide repeat homeobox 1 (TPRX1) G>A rs112842028 found on chromosome 19 at position 48305646, Protein Phosphatase, Mg2+/Mn2+ Dependent, 1E (PPM1E) G>GGAACCC rs201186780 found on chromosome 17 starting at 56833457, adenosine deaminase domain containing 2 (ADAD2) G>A rs8044695 found on chromosome 16 at position 84224967, PHD finger protein 2 (PHF2) T>TACCACCCCTGCCTCC (SEQ ID NO: 3) found on chromosome 9 starting at position 96438998, APC C>T rs121913328 found on chromosome 5 at position 112175390, KRAS C>G rs121913529 found on chromosome 12 at position 25398284, keratin associated protein 10-2 (KRTAP10-2) G>A rs76536096 found on chromosome 21 at position 45970774, zinc finger protein 732 (ZNF732) C>A found on chromosome 4 at position 265837, AT-rich interaction domain 1B (ARID1B) C>T found on chromosome 6 at position 157527948, myomesin 1

(MYOM1) C>T rs200770047 found on chromosome 18 at position 3188882, APC G>T on chromosome at position 112175480, NRDC T>A rs62648104 found on chromosome 1 at position 52306079, KRAS C>T rs121913530 found on chromosome 12 at position 25398285, APC C>T rs121913329 found on chromosome 5 at position 112175423, MAML2 C>T rs61901862 found on chromosome 11 at position 95825407, TP53 G>A found on chromosome 17 at position 7577094, APC TAAAAG>T found on chromosome 5 starting at position 112175211, coiled-coil domain containing 185 (CCDC185) G>A found on chromosome 1 at position 223567909, solute carrier family 6 member 20 (SLC6A20) G>A found on chromosome 3 at position 45801358, collapsin response mediator protein 1 (CRMP1) C>T found on chromosome 4 at position 5838495, protocadherin alpha 5 (PCDHA5) CT>C found on chromosome 5 starting at position 140203782, HECT domain and ankyrin repeat containing E3 ubiquitin protein ligase 1 (HACE1) G>A rs374813736 found on chromosome 6 at position 105198346, teneurin transmembrane protein 4 (TENM4) G>A found on chromosome 11 at position 78383150, neuronal differentiation 4 (NEUROD4) G>A rs139282092 found on chromosome 12 at position 55420513, DNA polymerase epsilon, catalytic subunit (POLE) G>A rs112358554 found on chromosome 12 at position 133218935, potassium calcium-activated channel subfamily N member 3 (KCNN3) G>GGCTGCTGCTGCTGCT (SEQ ID NO: 4) found on chromosome 1 starting at position 154842199, dentin sialophosphoprotein (DSPP) C>T rs141946550 found on chromosome 4 at position 88536451, NEFH A>G rs202065964 found on chromosome 22 at position 29885564, ZNF787 CTCG>C rs5828672 found on chromosome 19 starting at position 56599437, NEFH G>A rs370929798 found on chromosome 22 starting at position 29885562, Protocadherin Alpha 7 (PCDHA7) C>A found on chromosome at position 140215022, DSPP C>T rs142168734 found on chromosome 4 at position 88536448, TMPRSS13 G>C rs61900347 found on chromosome 11 at position 117789345, and ERICH6B T>C rs117004691 found on chromosome 13 at position 46170737 or any combination thereof, (b) amplifying the pre-amplified DNA obtain in step (a) in an amplification reaction using a second set of primers directed against the plurality of target gene mutations pre-amplified in step (a); and (c) detecting one or more amplification products from the amplification reaction in step (b).

2. The method of claim 1, wherein the pre-amplification reaction is a polymerase chain reaction, wherein the PCR is conducted for 10-14 cycles.

3. The method of claim 1, wherein the liquid biological sample is blood, serum, plasma, urine, saliva, sputum, cerebrospinal fluid, lymph, stool, or ejaculate.

4. The method of claim 1, wherein the DNA is genomic DNA (gDNA) or complementary DNA (cDNA), wherein the gDNA is derived from circulating tumor cells or microvesicles, wherein the cDNA is reverse transcribed from extracellular RNA derived from exosomes.

5. The method of claim 1, wherein the detecting comprises high throughput sequencing.

6. The method of claim 1, wherein the gene mutations are detected in 5 or more target genes.

7. The method of claim 1, wherein the gene mutations comprise a minimum number of target gene mutations needed to detect one or more types of cancer in the subject, wherein the one or more types of cancer are selected from colorectal, pancreatic, adrenocortical, melanoma, cutaneous melanoma, stomach adenocarcinoma, bladder cancer, lung adenocarcinoma, lung squamous cell carcinoma, cervical cancer, ovarian cancer, breast cancer, leukemia, liver cancer or any combination thereof.

8. The method of claim 7, wherein the minimum number of target gene mutations comprises all of the target gene mutations selected from TMPRSS13 CGGGCTGGAGATGCCT (SEQ ID NO: 1) >C rs201746372 found on chromosome 11 starting at position 117789312, TBP A>ACAG rs201732168 found on chromosome 6 starting at position 170871013, BRAF A>T rs113488022 found on chromosome 7 starting at position 140453136, KRAS C>T rs121913529 found on chromosome 12 at position 25398284, KRAS C>T rs112445441 found on chromosome 12 at position 25398281, IRF5 G>A rs113806178 found on chromosome 7 at position 128587374, TP53 C>T rs11540652 found on chromosome 17 at position 7577538, KRAS C>A rs121913529 found on chromosome 12 at position 25398284, ERICH6B T>C rs45625342 found on chromosome 13 at position 46170728, NEFH A>C rs75808076 found on chromosome 22 at position 29885567, APC C>T rs121913332 found on chromosome 5 at position 112175639, MAML2 TTGCTGCTGC (SEQ ID NO: 2)>T rs141671766 found on chromosome 11 starting at position 95825374, PIK3CA G>A rs104886003 found on chromosome 3 at position 178936091, APC C>T found on chromosome 5 at position 112116592, RNF43, BZRAP1-AS1 AC>A found on chromosome 17 starting at position 56435160, TPRX1 G>A rs112842028 found on chromosome 19 at position 48305646, PPM1E G>GGAACCC rs201186780 found on chromosome 17 starting at 56833457, ADAD2 G>A rs8044695 found on chromosome 16 at position 84224967, PHF2 T>TACCACCCCTGCCTCC (SEQ ID NO: 3) found on chromosome 9 starting at position 96438998, APC C>T rs121913328 found on chromosome 5 at position 112175390, KRAS C>G rs121913529 found on chromosome 12 at position 25398284, KRTAP10-2 G>A rs76536096 found on chromosome 21 at position 45970774, ZNF732 C>A found on chromosome 4 at position 265837, ARID1B C>T found on chromosome 6 at position 157527948, MYOM1 C>T rs200770047 found on chromosome 18 at position 3188882, APC G>T on chromosome at position 112175480, NRDC T>A rs62648104 found on chromosome 1 at position 52306079, KRAS C>T rs121913530 found on chromosome 12 at position 25398285, APC C>T rs121913329 found on chromosome 5 at position 112175423, MAML2 C>T rs61901862 found on chromosome 11 at position 95825407, TP53 G>A found on chromosome 17 at position 7577094, APC TAAAAG>T found on chromosome 5 starting at position 112175211, CCDC185 G>A found on chromosome 1 at position 223567909, SLC6A20 G>A found on chromosome 3 at position 45801358, CRMP1 C>T found on chromosome 4 at position 5838495, PCDHA5 CT>C found on chromosome 5 starting at position 140203782, HACE1 G>A rs374813736 found on chromosome 6 at position 105198346, TENM4 G>A found on chromosome 11 at position 78383150, NEUROD4 G>A rs139282092 found on chromosome 12 at position 55420513, POLE G>A rs112358554 found on chromosome 12 at position 133218935, KCNN3 G>GGCTGCTGCTGCTGCT (SEQ ID NO: 4) found on chromosome 1 starting at position 154842199, DSPP C>T rs141946550 found on chromosome 4 at position 88536451, NEFH A>G rs202065964 found on chromosome 22 at position 29885564, ZNF787 CTCG>C rs5828672 found on chromosome 19 starting at position 56599437, TP53 C>T rs28934578 found on chromosome 17 at position 7578406, NEFH G>A rs370929798 found on chromosome 22 at position 29885562, MUC4 T>A rs75263205 found on chromosome 3 at position 195518112, PCDHA7 C>A found on chromosome at position 140215022, DSPP C>T rs142168734 found on chromosome 4 at position 88536448, TMPRSS13 G>C rs61900347 found on chromosome 11 at position 117789345, and ERICH6B T>C rs117004691 found on chromosome 13 at position 46170737.

9. The method of claim 7, wherein the minimum number of target gene mutations is 10 to 25.

* * * * *

UNITED STATES PATENT AND TRADEMARK OFFICE
CERTIFICATE OF CORRECTION

PATENT NO. : 10,907,211 B1
APPLICATION NO. : 15/434799
DATED : February 2, 2021
INVENTOR(S) : Johannes Bhakdi Page 1 of 1

It is certified that error appears in the above-identified patent and that said Letters Patent is hereby corrected as shown below:

In the Claims

Claim 1, Column 75, Line 42, replace "thereof, (b)" with --thereof; (b)--.

Signed and Sealed this
Ninth Day of March, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 13

<210> SEQ ID NO 1
<211> LENGTH: 16
<212> TYPE: DNA
<213> ORGANISM: Homo sapiens

<400> SEQUENCE: 1
cgggctggag atgcct        16

```
<210> SEQ ID NO 2
<211> LENGTH: 10
<212> TYPE: DNA
<213> ORGANISM: Homo sapiens

<400> SEQUENCE: 2
ttgctgctgc                                                              10

<210> SEQ ID NO 3
<211> LENGTH: 16
<212> TYPE: DNA
<213> ORGANISM: Homo sapiens

<400> SEQUENCE: 3
taccacccct gcctcc                                                       16

<210> SEQ ID NO 4
<211> LENGTH: 16
<212> TYPE: DNA
<213> ORGANISM: Homo sapiens

<400> SEQUENCE: 4
ggctgctgct gctgct                                                       16

<210> SEQ ID NO 5
<211> LENGTH: 10
<212> TYPE: DNA
<213> ORGANISM: Homo sapiens

<400> SEQUENCE: 5
gagcctctgg                                                              10

<210> SEQ ID NO 6
<211> LENGTH: 10
<212> TYPE: DNA
<213> ORGANISM: Homo sapiens

<400> SEQUENCE: 6
cggcccccca                                                              10

<210> SEQ ID NO 7
<211> LENGTH: 16
<212> TYPE: DNA
<213> ORGANISM: Homo sapiens

<400> SEQUENCE: 7
accgccgaag tcgccg                                                       16

<210> SEQ ID NO 8
<211> LENGTH: 15
<212> TYPE: DNA
<213> ORGANISM: Homo sapiens

<400> SEQUENCE: 8
atcctcgagg cagcc                                                        15

<210> SEQ ID NO 9
<211> LENGTH: 17
<212> TYPE: DNA
<213> ORGANISM: Homo sapiens

<400> SEQUENCE: 9
gccagtgatg gtcacct                                                      17
```

```
<210> SEQ ID NO 10
<211> LENGTH: 25
<212> TYPE: DNA
<213> ORGANISM: Homo sapiens

<400> SEQUENCE: 10
gaccaaggaa gggcatcccg actgt                                           25

<210> SEQ ID NO 11
<211> LENGTH: 26
<212> TYPE: DNA
<213> ORGANISM: Homo sapiens

<400> SEQUENCE: 11
ggaccaagga agggcatccc gactgt                                          26

<210> SEQ ID NO 12
<211> LENGTH: 60
<212> TYPE: DNA
<213> ORGANISM: Homo sapiens

<400> SEQUENCE: 12
tgttgtcctg tttttatttc tctgtgttgt ttttttctta tttcttagag gagcaaaaag     60

<210> SEQ ID NO 13
<211> LENGTH: 61
<212> TYPE: DNA
<213> ORGANISM: Homo sapiens

<400> SEQUENCE: 13
ttgttgtcct gtttttattt ctctgtgttg tttttttctt atttcttaga ggagcaaaaa     60
g                                                                     61
```